US009045796B2

(12) United States Patent
Gunderson et al.

(10) Patent No.: US 9,045,796 B2
(45) Date of Patent: Jun. 2, 2015

(54) METHODS AND COMPOSITIONS FOR WHOLE GENOME AMPLIFICATION AND GENOTYPING

(75) Inventors: Kevin Gunderson, Encinitas, CA (US); Frank Steemers, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 10/871,513

(22) Filed: Jun. 17, 2004

(65) Prior Publication Data

US 2005/0037393 A1 Feb. 17, 2005

Related U.S. Application Data

(63) Continuation-in-part of application No. 10/681,800, filed on Oct. 8, 2003, now abandoned, which is a continuation of application No. 10/600,634, filed on Jun. 20, 2003, now abandoned.

(51) Int. Cl.
*C12Q 1/68* (2006.01)

(52) U.S. Cl.
CPC ............ *C12Q 1/6827* (2013.01); *C12Q 1/6816* (2013.01); *C12Q 1/682* (2013.01); *C12Q 1/6848* (2013.01)

(58) Field of Classification Search
None
See application file for complete search history.

(56) References Cited

U.S. PATENT DOCUMENTS

| 4,851,331 A | 7/1989 | Vary et al. |
| 4,988,617 A | 1/1991 | Landegren et al. |
| 5,043,272 A | 8/1991 | Hartley |
| 5,130,238 A | 7/1992 | Malek |
| 5,137,806 A | 8/1992 | LeMaistre |
| 5,455,166 A | 10/1995 | Walker |
| 5,503,980 A | 4/1996 | Cantor |
| 5,545,531 A | 8/1996 | Rava et al. |
| 5,561,044 A | 10/1996 | Walker |
| 5,595,890 A | 1/1997 | Newton et al. |
| 5,616,464 A | 4/1997 | Albagli |
| 5,624,825 A | 4/1997 | Walker |
| 5,639,611 A | 6/1997 | Wallace et al. |
| 5,648,211 A | 7/1997 | Fraiser |
| 5,679,524 A | 10/1997 | Nikiforov et al. |
| 5,712,124 A | 1/1998 | Walker |
| 5,731,171 A | 3/1998 | Bohlander |
| 5,767,259 A | 6/1998 | Albagli |

(Continued)

FOREIGN PATENT DOCUMENTS

| WO | WO 93/17126 | 9/1993 |
| WO | WO-95/00669 A1 | 1/1995 |

(Continued)

OTHER PUBLICATIONS

Brenner et.al (2000) Nature Biotechnol. vol. 18, pp. 630-634.*

(Continued)

*Primary Examiner* — Suchira Pande
(74) *Attorney, Agent, or Firm* — Jones Day

(57) ABSTRACT

This invention provides methods of amplifying genomic DNA to obtain an amplified representative population of genome fragments. Methods are further provided for obtaining amplified genomic DNA representations of a desired complexity. The invention further provides methods for simultaneously detecting large numbers of typable loci for an amplified representative population of genome fragments. Accordingly the methods can be used to genotype individuals on a genome-wide scale.

30 Claims, 18 Drawing Sheets

(56) References Cited

U.S. PATENT DOCUMENTS

| | | | |
|---|---|---|---|
| 5,773,257 A | 6/1998 | Nielson | |
| 5,846,710 A | 12/1998 | Bajaj | |
| 5,856,092 A | 1/1999 | Dale et al. | |
| 5,888,819 A | 3/1999 | Goelet | |
| 5,955,268 A | 9/1999 | Granados | |
| 5,968,740 A | 10/1999 | Fodor | |
| 6,004,744 A | 12/1999 | Goelet | |
| 6,013,431 A | 1/2000 | Soderlund | |
| 6,023,540 A | 2/2000 | Walt | |
| 6,045,994 A | 4/2000 | Zabeau et al. | |
| 6,087,095 A | 7/2000 | Rosenthal et al. | |
| 6,100,030 A | 8/2000 | McCasky-Feazel et al. | |
| 6,107,023 A | 8/2000 | Reyes et al. | |
| 6,124,120 A | 9/2000 | Lizardi | |
| 6,150,095 A | 11/2000 | Southern | |
| 6,153,379 A | 11/2000 | Caskey | |
| 6,180,408 B1 | 1/2001 | Kwok et al. | |
| 6,191,267 B1 | 2/2001 | Kong | |
| 6,200,737 B1 | 3/2001 | Walt | |
| 6,203,989 B1 | 3/2001 | Goldberg | |
| 6,214,587 B1 | 4/2001 | Dattagupta | |
| 6,225,056 B1 | 5/2001 | Abe et al. | |
| 6,268,152 B1 | 7/2001 | Fodor | |
| 6,277,606 B1 | 8/2001 | Wigler et al. | |
| 6,280,954 B1 | 8/2001 | Ulfendahl | |
| 6,287,768 B1 | 9/2001 | Chenchik | |
| 6,287,776 B1 | 9/2001 | Hefti | |
| 6,288,220 B1 | 9/2001 | Kambara | |
| 6,291,187 B1 | 9/2001 | Kingsmore | |
| 6,291,193 B1 | 9/2001 | Khodadoust | |
| 6,297,006 B1 | 10/2001 | Drmanac | |
| 6,327,410 B1 | 12/2001 | Walt | |
| 6,355,431 B1 * | 3/2002 | Chee et al. | 435/6 |
| 6,355,433 B1 | 3/2002 | Xu | |
| 6,361,947 B1 | 3/2002 | Dong et al. | |
| 6,429,027 B1 | 8/2002 | Chee | |
| 6,448,010 B1 | 9/2002 | Zhao | |
| 6,524,793 B1 | 2/2003 | Chandler | |
| 6,531,283 B1 | 3/2003 | Kingsmore | |
| 6,537,748 B1 | 3/2003 | Goelet | |
| 6,573,051 B2 * | 6/2003 | Alsmadi et al. | 435/6 |
| 6,607,888 B2 | 8/2003 | Schwartz | |
| 6,617,137 B2 * | 9/2003 | Dean et al. | 435/91.1 |
| 6,703,228 B1 | 3/2004 | Landers et al. | |
| 7,670,810 B2 | 3/2010 | Gunderson et al. | |
| 2001/0053334 A1 | 12/2001 | Chen et al. | |
| 2002/0001801 A1 | 1/2002 | Fan | |
| 2002/0006622 A1 | 1/2002 | Bradley et al. | |
| 2002/0039728 A1 | 4/2002 | Kain et al. | |
| 2002/0049682 A1 | 4/2002 | Yamamoto et al. | |
| 2002/0094525 A1 | 7/2002 | McIntosh et al. | |
| 2002/0102578 A1 | 8/2002 | Dickinson | |
| 2003/0082590 A1 | 5/2003 | Van Ness | |
| 2003/0087298 A1 | 5/2003 | Green | |
| 2003/0096235 A1 | 5/2003 | Dong | |
| 2003/0096986 A1 | 5/2003 | Mei | |
| 2003/0104431 A1 | 6/2003 | Van Ness | |
| 2003/0108870 A1 | 6/2003 | Ji et al. | |
| 2003/0118998 A1 | 6/2003 | Dean | |
| 2003/0138800 A1 | 7/2003 | Van Ness et al. | |
| 2003/0143587 A1 | 7/2003 | Dean | |
| 2003/0162210 A1 | 8/2003 | Chetverin et al. | |
| 2004/0005614 A1 | 1/2004 | Kurn et al. | |
| 2004/0018512 A1 | 1/2004 | Sorge et al. | |
| 2004/0067493 A1 | 4/2004 | Matsuzaki et al. | |
| 2004/0137473 A1 | 7/2004 | Wigler et al. | |
| 2004/0185475 A1 | 9/2004 | Cao et al. | |
| 2004/0248144 A1 | 12/2004 | Mir | |
| 2005/0019793 A1 | 1/2005 | Kurn et al. | |
| 2005/0123914 A1 * | 6/2005 | Katz et al. | 435/6 |
| 2006/0029267 A1 * | 2/2006 | Frost et al. | 382/129 |
| 2007/0003938 A1 | 1/2007 | Fu et al. | |

FOREIGN PATENT DOCUMENTS

| | | | | |
|---|---|---|---|---|
| WO | WO96/31622 | * | 10/1996 | C12Q 1/68 |
| WO | WO-98/40726 A1 | | 9/1998 | |
| WO | WO-98/50782 A2 | | 11/1998 | |
| WO | WO 99/23256 | * | 5/1999 | 435/91.1 |
| WO | WO 99/23256 A1 | | 5/1999 | |
| WO | WO 99/23256 A1 | | 5/1999 | |
| WO | WO-00/17390 A1 | | 3/2000 | |
| WO | WO 00/18962 | | 4/2000 | |
| WO | WO-00/18962 | | 4/2000 | |
| WO | WO-00/61800 A2 | | 10/2000 | |
| WO | WO-00/63437 A2 | | 10/2000 | |
| WO | WO 01/57269 A2 | | 8/2001 | |
| WO | WO 01/57269 A3 | | 8/2001 | |
| WO | WO-01/83822 A2 | | 11/2001 | |
| WO | WO-02/101022 | | 12/2002 | |
| WO | WO 02/101022 | | 12/2002 | |
| WO | WO 02/101022 A2 | | 12/2002 | |
| WO | WO-02/103054 A1 | | 12/2002 | |
| WO | WO-03/008624 A2 | | 1/2003 | |
| WO | WO 03/012042 A2 | | 2/2003 | |
| WO | WO 03/033724 A2 | | 4/2003 | |

OTHER PUBLICATIONS

Lage et al. (Feb. 2003) Genome research vol. 13 (2): pp. 294-307.*
Luppa et al. (2001) Clinica Chimica Acta 314: 1-26.*
Packard BioScience, Application Note PBT-002, Jan. 2001.*
Brenner et al. (2000) Nature Biotechnology vol. 18 pp. 630-634.*
Barker et al. (May 2004) Genome Research vol. 14: pp. 901-907.*
Baner, J. et al., "Signal amplification of padlock probes by rolling circle replication," Nucleic Acids Research, 26:5073-5078 (1998).
Barany, F., "Genetic disease detection and DNA amplification using cloned thermostable ligase," Proceedings of the National Academy of Sciences USA, 88:189-193 (1991).
Barrett, M. et al., "Genotypic analysis of multiple loci in somatic cells by whole genome amplification," Nucleic Acids Research, 23:3488-3492 (1995).
Bassam, B. et al., "DNA Fingerprinting using Arbitrary Primer Technology (APT): A Tool or a Torment," Australasian Biotechnology, 4:232-236 (1994).
Bobrow, M. et al., "Catalyzed reporter deposition, a novel method of signal amplification. Application to Immunoassays," Journal of Immunological Methods, 125:279-285 (1989).
Brady, G., "Expression profiling of single mammalian cells—small is beautiful," Yeast, 17:211-217 (2000).
Breen, G., "Novel and alternate SNP and genetic technologies," Psychiatric Genetics, 12:83-88 (2002).
Butte, A., "The Use and Analysis of Microarray Data," Nature Reviews Drug Discovery, 1:951-960 (2002).
Cai, W. et al., "Genome-wide detection of chromosomal imbalances in tumors using BAC microarrays," Nature Biotechnology, 20:393-396 (2002).
Carter, N. P. et al., "Comparative Analysis of Comparative Genomic Hybridization Microarray Technologies: Report of a Workshop Sponsored by the Wellcome Trust," Cytometry, 49:43-48 (2002).
Casas, E. et al., "Evaluation of Different Amplification Protocols for Use in Primer-Extension Preamplification," Biotechniques, 20:219-225 (1996).
Cheung, V. et al., "Whole genome amplification using a degenerate oligonucleotide primer allows hundreds of genotypes to be performed on less than one nanogram of genomic DNA," Proceedings of the National Academy of Sciences USA, 93:14676-14679 (1996).
Cunin, F. et al., "Biomolecular screening with encoded porous-silicon photonic crystals," Nature Materials, 1:39-41 (2002).
Dean, F. et al., "Comprehensive human genome amplification using multiple displacement amplification," Proceedings of the National Academy of Sciences USA, 99:5261-5266 (2002).
Feinberg, A. et al., "A Technique for Radiolabeling DNA Restriction Endonuclease Fragments to High Specific Activity," Analytical Biochemistry, 132:6-13 (1983).
Fiegler, H. et al., "DNA Microarrays for Comparative Genomic Hybridization Based on DOP-PCR Amplification of BAC and PAC Clones," Genes Chromosomes & Cancer, 36:361-374 (2003).

(56) References Cited

OTHER PUBLICATIONS

Gabriel, S. et al., "The Structure of Haplotype Blocks in the Human Genome," Science, 296:2225-2229 (2002).
Grothues, D. et al., "PCR amplification of megabase DNA with tagged random primers (T-PCR)," Nucleic Acids Research, 21:1321-1322 (1993).
Guilfoyle, R. et al., "Ligation-mediated pcr amplification of specific fragments from a Class-II restriction endonuclease total digest," Nucleic Acids Research, 25:1854-1858 (1997).
Hawkins, T. et al., "Whole genome amplification—applications and advances," Current Opinion in Biotechnology, 13:65-67 (2002).
Kittler, R. et al., "A Whole Genome Amplification Method to Generate Long Fragments from Low Quantities of Genomic DNA," Analytical Biochemistry, 300:237-244 (2002).
Klein, C. et al., "Comparative genomic hybridization, loss of heterozygosity, and DNA sequence analysis of single cells," Proceedings of the National Academy of Sciences USA, 96:4494-4499 (1999).
Lage, J. et al., "Whole Genome Analysis of Genetic Alterations in Small DNA Samples Using Hyperbranched Strand Displacement Amplification and Array-CGH," Genome Research, 13:294-307 (2003).
Lizardi, P. et al., "Mutation detection and single-molecule counting using isothermal rolling-circle amplification," Nature Genetics, 19:225-232 (1998).
Lucito, R. et al., "Genetic analysis using genomic representations," Proceedings of the National Academy of Sciences USA, 95:4487-4492 (1998).
Lucito, R. et al., "Detecting Gene Copy Number Fluctuations in Tumor Cells by Microarray Analysis of Genomic Representations," Genome Research, 10:1726-1736 (2000).
Mackey, J. et al., "Use of Random Primer Extension for Concurrent Amplification and Nonradioactive Labeling of Nucleic Acids," Analytical Biochemistry, 212:428-435 (1993).
O'Meara, D. et al., "SNP typing by apyrase-mediated allele-specific primer extension on DNA microarrays," Nucleic Acids Research, 30:1-8 (2002).
Pastinen, T. et al., "Minisequencing: A specific Tool for DNA Analysis and Diagnostics on Oligonucleotide Arrays," Genome Research, 7:606-614 (1997).
Pastinen, T. et al., "A System for Specific, High-throughput Genotyping by Allele-specific Primer Extension on Microarrays," Genome Research, 10:1031-1042 (2000).
Peterson, D. et al., "Integration of Cot Analysis, DNA Cloning, and High-Throughput Sequencing Facilitates Genome Characterization and Gene Discovery," Genome Research, 12:795-807 (2002).
Pinkel, D. et al., "High resolution analysis of DNA copy number variation using comparative genomic hybridization to microarrays," Nature Genetics, 20:207-211 (1998).
Pollack, J. et al., "Genome-wide analysis of DNA copy-number changes using cDNA microarrays," Nature Genetics, 23:41-46 (1999).
Schmidt, B. et al., "Signal Amplification in the Detection of Single-copy DNA and RNA by Enzyme-catalyzed Deposition (CARD) of the Novel Fluorescent Reporter Substrate Cy3.29-tyramide," Journal of Histochemistry and Cytochemistry, 45:365-373 (1997).
Singer, B. et al., "Libraries for genomic SELEX," Nucleic Acids Research, 25:781-786 (1997).
Snabes, M. et al., "Preimplantation single-cell analysis of multiple genetic loci by whole-genome amplification," Proceedings of the National Academy of Sciences USA, 91:6181-6185 (1994).
Speel, E. et al., "Amplification Methods to Increase the Sensitivity of In Situ Hybridization: Play CARD(s)," Journal of Histochemistry and Cytochemistry, 47:281-288 (1999).
Speel, E. et al., "Sensitive Multicolor Fluorescence In Situ Hybridization Using Catalyzed Reporter Deposition (CARD) Amplification," Journal of Histochemistry and Cytochemistry, 45:1439-1446 (1997).

Speel, E. et al., "A Novel Fluorescence Detection Method for In Situ Hybridization, Based on the Alkaline Phosphatase-Fast Red Reaction," Journal of Histochemistry and Cytochemistry, 40:1299-1308 (1992).
Syvanen, A. et al., "A Primer-Guided Nucleotide Incorporation Assay in the Genotyping of Apolipoprotein E," Genomics, 8:684-692 (1990).
Syvanen, A. et al., "Detection of Point Mutations by Solid-Phase Methods," Human Mutation 3:172-179 (1994).
Telenius, H. et al., "Degenerate Oligonucleotide-Primed PCR: General Amplification of Target DNA by a Single Degenerate Primer," Genomics, 13:718-725 (1992).
Unrau, P. et al., "Non-cloning amplification of specific DNA fragments from whole genomic DNA digests using DNA 'indexers'," Gene, 145:163-169 (1994).
Walker, G.T et al., "Strand displacement amplification—an isothermal, in vitro DNA amplification technique," Nucleic Acids Research, 20:1691-1696 (1992).
Walker, G. T. et al., "Isothermal in vitro amplification of DNA by a restriction enzyme/DNA polymerase system," Proceedings of the National Academy of Sciences USA, 89:392-396 (1992).
Weber, J. et al., "Genotyping for Human Whole-Genome Scans: Past, Present, and Future," Advances in Genetics, 42:77-96 (2001).
Zhang, L. et al., "Whole genome amplification from a single cell: Implications for genetic analysis," Proceedings of the National Academy of Sciences USA, 89:5847-5851 (1992).
Kinzler, K. et al., "Whole genome PCR: application to the identification of sequences bound by gene regulatory proteins," Nucleic Acids Research, 17(10):3645-3653 (1989).
Nikiforov, T. et al., "Genetic Bit Analysis: a solid phase method for typing single nucleotide polymorphisms," Nucleic Acids Research, 22(20):4167-4175 (1994).
Shumaker, J. et al, "Primer Extension Mutation Detection Method: A Non-Gel Based Method for Rapid Mutation Identification," The Fifth International Symposium on Human Identification, 147-151 (1994).
Shumaker, J. et al., "Mutation Detection by Solid Phase Primer Extension," Human Mutation, 7:346-354 (1996).
Syvanen, A.-C., "Detection of point mutations in human genes by the solid-phase minisequencing method," Clinica Chimica Acta, 226:225-236 (1994).
Twyman, R. et al., "Techniques patents for SNP genotyping," Pharmacogenomics, 4(1):67-79 (2003).
Brutlag, D. et al., "Enzymatic Synthesis of Deoxyribonucleic Acid," The Journal of Biological Chemistry, 247(1):241-248 (1972).
Chetverin, A. et al., "Oligonudeotide Arrays: New Concepts and Possibilities," Bio/Technology,12:1093-1099 (1994).
Huang, M. et al., "Extension of base mispairs by Taq DNA polymerase: implications for single nucleotide discrimination in PCR," Nucleic Acids Research, 20(17):4567-4573 (1992).
Kurg, A. et al., "Arrayed Primer Extension: Solid-Phase Four-Color DNA Resequencing and Mutation Detection Technology," Genetic Testing, 4(1):1-7 (2000).
Landegren, U., "Detection of Mutations in Human DNA," GATA, 9(1):3-8 (1992).
Noonan, K. et al., "mRNA phenotyping by enzymatic amplification of randomly primed cDNA," Nucleic Acids Research, 16(21):10368 (1988).
Petruska, J. et al., "Comparison between DNA melting thermodynamics and DNA polymerase fidelity," Proc. Natl. Acad. Sci. USA, 85:6252-6256 (1988).
Wu, D., et al., "Allele-specific enzymatic amplification of B-globin genomic DNA for diagnosis of sickle cell anemia," Proc. Natl. Acad. Sci. USA, 88:2757-2760 (1989).
Gunderson, K. et al., "Whole Genome Genotyping on Arrays," presented at The Biology of Genomes, Cold Spring Harbor Laboratory (2004).
Illumina Press Release, Illumina Announces 100,000 SNPs on a Single BeadChip, Apr. 21, 2004, [online], [retrieved on Jul. 22, 2004] Retrieved from the Illumina website <URL: http://www.shareholder.com/illumina/ReleaseDetail.cfm?ReleaseID=133388>.
Kennedy, G. et al., "Large-scale genotyping of complex DNA," Nature Biotechnology, 21:1233-1237 (2003).

(56) References Cited

OTHER PUBLICATIONS

Matsuzaki, "Parallel Genotyping of Over 10,000 SNPs Using a One-Primer Assay on a High-Density Oligonucleotide Array," Genome Research, 14:414-425 (2004).
MIDAScan AT Mutation Detection Kit Instructions, 2000, [online], [retrieved on Jul. 22, 2004] Retrieved from the Internet –URL: http://www.interchim.com/interchim/bio/midascan1.pdf>.
Dong, S. et al., "Flexible Use of High-Density Oligonucleotide Arrays for Single-Nucleotide Polymorphism Discovery and Validation," Genome Research, 11:1418-1424 (2001).
Syvanen, A. C., "Accessing Genetic Variation: Genotyping Single Nucleotide Polymorphisms," Nature Reviews: Genetics, 2:930-942 (2001).
Landegren, U. et al., "A Ligase-Mediated Gene Detection Technique," Science, 241:1077-1080 (1988).
Packard Bioscience Application Note, "SNP Genotyping (Zip Code or Apex Methods), Protein Arrays and Gene Expression," ScanArray Application Note PBT-002 (2001).
Sun, F. et al., "Whole genome amplification of single cells: mathematical analysis of PEP and tagged PCR," Nucleic Acids Research, 23(15):3034-3040 (1995).
Chung, J. et al., "Repair activities of 8-oxoguanine DNA glycosylase from Archaeoglobus fulgidus, a hyperthermophilic archaeon," Mutation Research, 486: 99-111 (2001).
Graves, D., "Powerful tools for genetic analysis come of age," Trends in Biotechnology, 17: 127-134 (1999).
Irie et al., "Automated DNA fragment collection by capillary array gel electrophoresis in search of differentially espressed genes," Electrophoresis 21(2):367-374 (2000).
Krokan, H. et al., "DNA glycosylases in the base excision repair of DNA," Biochem. J., 325(1): 1-16 (1997).
Lindblad-Toh, K. et al., "Loss of heterozygosity analysis of small-cell lung carcinomas using single-nucleotide polymorphism arrays," Nature Biotechnology, 18: 1001-1005 (2000).
Lipshutz, R. et al., "High density synthetic oligonucleotide arrays," Nature Genetics, 21: 20-24 (1999).
Maldonado-Rodriguez, R. et al., "Hybridization of Glass-Tethered Oligonucleotide Probes to Target Strands Preannealed with Labeled Auxiliary Oligonucleotides," Molecular Biotechnology, 11: 1-12 (1999).
Schubert, E. et al., "Single nucleotide polymorphism array analysis of flow-sorted epithelial cells from frozen versus fixed tissues for whole genome analysis of allelic loss in breast cancer," American Journal of Pathology, 160(1): 73-79 (2002).

Vaughan, P. et al., "Glycosylase mediated polymorphism detection (GMPD)—a novel process for genetic analysis," Genetic Analysis: Biomolecular Engineering, 14: 169-175 (1999).
"Common PCR enzymes," Roche Molecular Biochemicals PCR Application Manual, 2nd Edition, Chapter 2, 1 page (1999).
Chan, Vincent, et al. "Adsorption and Surface Diffusion of DNA Oligonucleotides at Liquid/Solid Interfaces," Langmuir (1997) 13:320-329.
Halperin, A., et al. "Sensitivity, Specificity, and the Hybridization Isotherms of DNA Chips," Biophysical Journal (2006) 86-718-730.
Bowtell, David et al., "DNA Microarrays: A Molecular Cloning Manual," Cold Spring Harbor Laboratory Press, New York (2003).
Yue, Huibin et al., "An evaluation of the performance of cDNA microarrays for detecting changes in global mRNA expression," Nucleic Acids Research (2001) 29(8):e41.
Hardiman, Gary, "Microarrays Methods and Applications: Nuts & Bolts," DNA Press, United States (2003).
Hardiman, Gary, "Microarray platforms—comparisons and contrasts," Pharmacogenomics, 5(5), 487-502 (2004).
Australian Examiner's Report dated Sep. 10, 2008, on Patent Application No. 2004253882, 4 pages.
Canadian Office Action dated Sep. 15, 2009, for Patent Application No. 2528577, 3 pages.
Notice of Allowance dated Dec. 16, 2009, issued for U.S. Appl. No. 10/872,141, 23 pages.
Japanese Notice of Reasons for Rejection dated Februrary 9, 2010, for Patent Application No. 2006-517406, 3 pages and translation of same (5 pages).
Response to Australian Examiner's Report dated May 21, 2010 for Application No. 2004263882, 22 pages.
Australian Notice of Acceptance dated May 31, 2010, for Patent Application No. 2004253882, 3 pages.
File Wrapper for European Application No. 04776759.5, 254 pages.
Response to Canadian Office Action for Patent Application No. 2528577, dated Mar. 15, 2010, 11 pages.
Notice of Final Rejection mailed May 2, 2011, in Japanese Application 2006-517406 (JP nat. ph. of PCT/US04/19545, which is international counterpart of this application).
Hosono, et al., "Unbiased whole-genome amplification directly from clinical samples", *Genome Research*, 13(5) 2003, 954-964.
Syvanen, Ann-Christine, "Form gels to chip: 'Minisequencing' Primer Extension for Analysis of Point Mutations and Single Nucleotide Polymorphisms", *Human Mutation*, 13 1999, 1-10.
Zhao, et al., "Immobilization of oligodeoxyribonucleotides with multiple anchors to mcrochips", *Nucleic Acids Research 29* 2001, 955-959.

* cited by examiner

| Condition | dNTPs (mM) | Primer (uM) | Yield (ug) | Amplification |
|---|---|---|---|---|
| 1 | 1 | 50 | 49.5 | 4950 |
| 2 | 1 | 10 | 28.5 | 2850 |
| 3 | 1 | 2 | 12.0 | 1200 |
| 4 | 1 | 0 | 6.0 | 600 |
| 5 | 2 | 50 | 79.5 | 7950 |
| 6 | 2 | 10 | 42.0 | 4200 |
| 7 | 2 | 2 | 21.0 | 2100 |
| 8 | 2 | 0 | 6.0 | 600 |

A.

| Genotyping Accuracy: | | | |
|---|---|---|---|
| Call Rate | Accuracy | Calls | Correct Calls |
| 100% | 99.95% | 4092 | 4090 |
| 99.70% | 100% | 4078 | 4078 |

METHODS AND COMPOSITIONS FOR WHOLE GENOME AMPLIFICATION AND GENOTYPING

This application is a continuation-in-part of application Ser. No. 10/681,800, filed on Oct. 8, 2003, now abandoned, which is a continuation of application Ser. No. 10/600,634, filed on Jun. 20, 2003, now abandoned, both of which are incorporated herein in their entirety.

FIELD OF THE INVENTION

The present invention relates generally to genetic analysis and more specifically to amplification of whole genomes and genotyping based on pluralities of genetic markers spanning genomes.

BACKGROUND OF THE INVENTION

Most of any one person's DNA, some 99.9 percent, is exactly the same as any other person's DNA. The roughly 0.1% difference in the genome sequence accounts for a wide variety of the differences among people, such as eye color and blood group. Genetic variation also plays a role in whether a person is at risk for getting particular diseases or whether a person is likely to have a favorable or adverse response to a particular drug. Single gene differences in individuals have been associated with elevated risk for acquiring a variety of diseases, such as cystic fibrosis and sickle cell disease. More complex interrelationships among multiple genes and the environment are responsible for many traits like risk for some common diseases, such as diabetes, cancer, stroke, Alzheimer's disease, Parkinson's disease, depression, alcoholism, heart disease, arthritis and asthma.

Genetic-based diagnostic tests are available for several highly penetrant diseases caused by single genes, such as cystic fibrosis. Such tests can be performed by probing for particular mutations or polymorphisms in the respective genes. Accordingly, risk for contracting a particular disease can be determined well before symptoms appear and, if desired, preventative measures can be taken. However, it is believed that the majority of diseases, including many common diseases such as diabetes, heart disease, cancers, and psychiatric disorders, are affected by multiple genes as well as environmental conditions. Thus, diagnosis of such diseases based on genetics is considerably more complex as the number of genes to be interrogated increases.

Recently, through a variety of genotyping efforts, a large number of polymorphic DNA markers have been identified, many of which are believed to be associated with the probability of developing particular traits such as risk of acquiring known diseases. Exemplary polymorphic DNA markers that are available include single nucleotide polymorphisms (SNPs) which occur at an average frequency of more than 1 per kilobase in human genomic DNA. Many of these SNPs are likely to be therapeutically relevant genetic variants and/or involved in genetic predisposition to disease. However, current methods for genome-wide interrogation of SNPs and other markers are inefficient, thereby rendering the identification of useful diagnostic marker sets impractical.

The ability to simultaneously genotype large numbers of SNP markers across a DNA sample is becoming increasingly important for genetic linkage and association studies. A major limitation to whole genome association studies is the lack of a technology to perform highly-multiplexed SNP genotyping. The generation of the complete haplotype map of the human genome across major ethnic groups will provide the SNP content for whole genome association studies (estimated at about 200,000-300,000 SNPs). However, currently available genotyping methods are cumbersome and inefficient for scoring the large numbers of SNPs needed to generate a haplotype map.

Thus there is a need in the art for methods of simultaneously interrogating large numbers of gene loci on a whole genome scale. Such benefits will affect the genomic discovery process and the genetic analysis of diseases, as well as the genetic analysis of individuals. This invention satisfies this need and provides other advantages as well. This invention describes and demonstrates a method to perform large scale multiplexing reactions enabling a new era in genomics.

SUMMARY OF THE INVENTION

In one aspect, the present invention features a method of detecting one or several typable loci contained within a given genome, where the method includes the steps of providing an amplified representative population of genome fragments having such typable loci, contacting the genome fragments with a plurality of nucleic acid probes having sequences corresponding to the typable loci under conditions wherein probe-fragment hybrids are formed; and detecting typable loci of the probe-fragment hybrids. In particular embodiments these nucleic acid probes are at most 125 nucleotides in length. However, probes having any of a variety of lengths or sequences can be used as set forth in more detail below.

In another aspect, the present invention features a method of detecting typable loci of a genome including the steps of providing an amplified representative population of genome fragments that has such typable loci, contacting the genome fragments with a plurality of nucleic acid probes having sequences corresponding to the typable loci under conditions wherein probe-fragment hybrids are formed; and directly detecting typable loci of the probe-fragment hybrids.

In a further aspect, the present invention features a method of detecting typable loci of a genome including the steps of providing an amplified representative population of genome fragments having the typable loci; contacting the genome fragments with a plurality of immobilized nucleic acid probes having sequences corresponding to the typable loci under conditions wherein immobilized probe-fragment hybrids are formed; modifying the immobilized probe-fragment hybrids; and detecting a probe or fragment that has been modified, thereby detecting the typable loci of the genome.

The invention also provides a method, including the steps of (a) providing a plurality of genome fragments, wherein the plurality of genome fragments has at least 100 ug of DNA having a complexity of at least 1 Gigabases; (b) contacting the plurality of genome fragments with a plurality of different immobilized nucleic acid probes, wherein at least 500 of the different nucleic acid probes hybridize with genome fragments to form probe-fragment hybrids; and (c) detecting typable loci of the probe-fragment hybrids.

A method of the invention can also include the steps of (a) providing a plurality of genome fragments, wherein the plurality of genome fragments has a concentration of at least 1 ug/ul of DNA having a complexity of at least 1 Gigabases; (b) contacting the plurality of genome fragments with a plurality of different immobilized nucleic acid probes, wherein at least 500 of the different nucleic acid probes hybridize with genome fragments to form probe-fragment hybrids; and (c) detecting typable loci of the probe-fragment hybrids.

In an additional aspect, the present invention features a method of amplifying genomic DNA, including the steps of providing isolated double stranded genomic DNA, producing nicked DNA by contacting the double stranded genomic DNA with a nicking agent, contacting this nicked DNA with a strand displacing polymerase and a plurality of primers, so as to amplify the genomic DNA.

The invention further provides a method for detecting typable loci of a genome. The method includes the steps of (a) in vitro transcribing a plurality of amplified gDNA fragments, thereby obtaining genomic RNA (gRNA) fragments; (b) hybridizing the gRNA fragments with a plurality of nucleic acid probes having sequences corresponding to the typable loci; and (c) detecting typable loci of the gRNA fragments that hybridize to the probes.

The invention further provides a method of producing a reduced complexity, locus-specific, amplified representative population of genome fragments. The method includes the steps of (a) replicating a native genome with a plurality of random primers, thereby producing an amplified representative population of genome fragments; (b) replicating a sub-population of the amplified representative population of genome fragments with a plurality of different locus-specific primers, thereby producing a locus-specific, amplified representative population of genome fragments; and (c) isolating the sub-population, thereby producing a reduced complexity, locus-specific, amplified representative population of genome fragments.

The invention also provides a method for inhibiting ectopic extension of probes in a primer extension assay. The method includes the steps of (a) contacting a plurality of probe nucleic acids with a plurality of target nucleic acids under conditions wherein probe-target hybrids are formed; (b) contacting the plurality of probe nucleic acids with an ectopic extension inhibitor under conditions wherein probe-ectopic extension inhibitor hybrids are formed; and (c) selectively modifying probes in the probe-target hybrids compared to probes in the probe-ectopic extension inhibitor hybrids.

Further provided is a method including the steps of (a) contacting a plurality of genome fragments with a plurality of different immobilized nucleic acid probes under conditions wherein immobilized probe-fragment hybrids are formed; (b) modifying the immobilized probes while hybridized to the genome fragments, thereby forming modified immobilized probes; (c) removing said genome fragments from said probe-fragment hybrids; and (d) detecting the modified immobilized probes after removing the genome fragments, thereby detecting typable loci of the genome fragments.

The invention also provides a method including the steps of (a) representationally amplifying a native genome, wherein an amplified representative population of genome fragments having the typable loci is produced under isothermal conditions; (b) contacting the genome fragments with a plurality of nucleic acid probes having sequences corresponding to the typable loci under conditions wherein probe-fragment hybrids are formed; and (c) detecting typable loci of the probe-fragment hybrids.

DEFINITIONS

Figure 1:
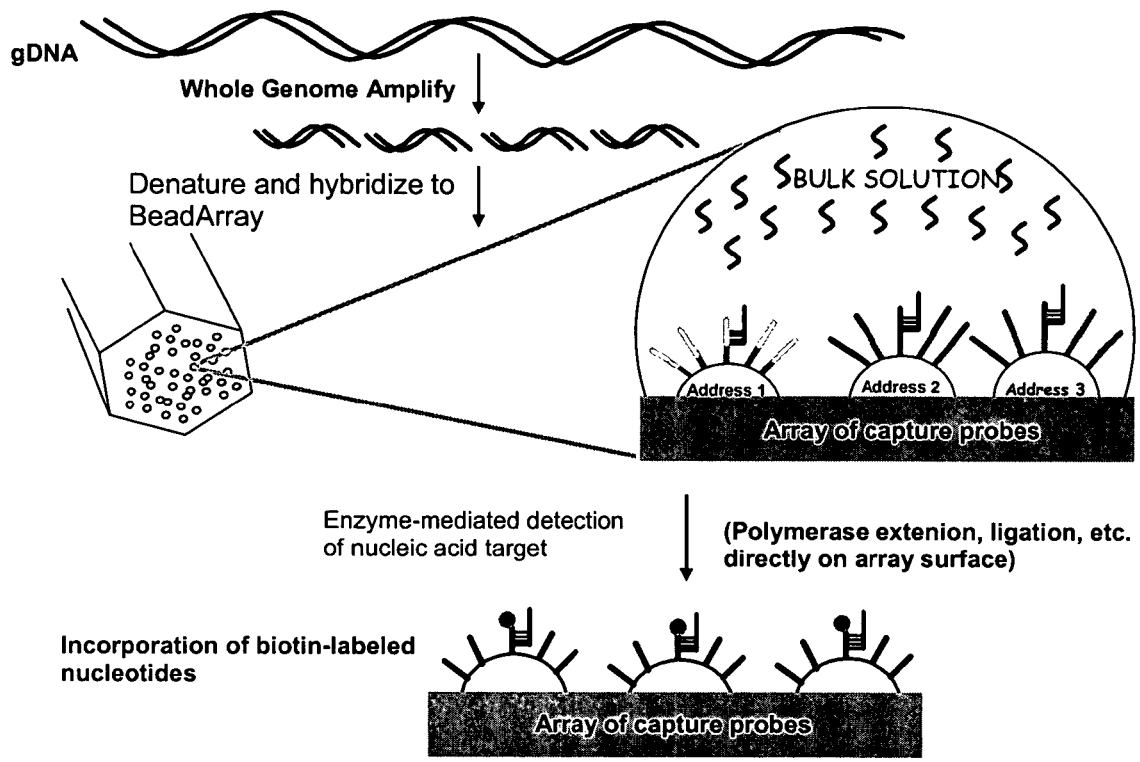
FIG. 1 shows a diagram of a whole genome genotyping (WGG) method of the invention.

As used herein, the term "genome" is intended to mean the full complement of chromosomal DNA found within the nucleus of a eukaryotic cell. The term can also be used to refer to the entire genetic complement of a prokaryote, virus, mitochondrion or chloroplast or to the haploid nuclear genetic complement of a eukaryotic species.

As used herein, the term "genomic DNA" or "gDNA" is intended to mean one or more chromosomal polymeric deoxyribonucleotide molecules occurring naturally in the nucleus of a eukaryotic cell or in a prokaryote, virus, mitochondrion or chloroplast and containing sequences that are naturally transcribed into RNA as well as sequences that are not naturally transcribed into RNA by the cell. A gDNA of a eukaryotic cell contains at least one centromere, two telomeres, one origin of replication, and one sequence that is not transcribed into RNA by the eukaryotic cell including, for example, an intron or transcription promoter. A gDNA of a prokaryotic cell contains at least one origin of replication and one sequence that is not transcribed into RNA by the prokaryotic cell including, for example, a transcription promoter. A eukaryotic genomic DNA can be distinguished from prokaryotic, viral or organellar genomic DNA, for example, according to the presence of introns in eukaryotic genomic DNA and absence of introns in the gDNA of the others.

As used herein, the term "detecting" is intended to mean any method of determining the presence of a particular molecule such as a nucleic acid having a specific nucleotide sequence. Techniques used to detect a nucleic acid include, for example, hybridization to the sequence to be detected. However, particular embodiments of this invention need not require hybridization directly to the sequence to be detected, but rather the hybridization can occur near the sequence to be detected, or adjacent to the sequence to be detected. Use of the term "near" is meant to imply within about 150 bases from the sequence to be detected. Other distances along a nucleic acid that are within about 150 bases and therefore near include, for example, about 100, 50 40, 30, 20, 19, 18, 17, 16, 15, 14, 13, 12, 11, 10, 9, 8, 7, 6, 5, 4, 3, 2, or 1 bases from the sequence to be detected. Hybridization can occur at sequences that are further distances from a locus or sequence to be detected including, for example, a distance of about 250 bases, 500 bases, 1 kilobase or more up to and including the length of the target nucleic acids or genome fragments being detected.

Examples of reagents which are useful for detection include, but are not limited to, radiolabeled probes, fluorophore-labeled probes, quantum dot-labeled probes, chromophore-labeled probes, enzyme-labeled probes, affinity ligand-labeled probes, electromagnetic spin labeled probes, heavy atom labeled probes, probes labeled with nanoparticle light scattering labels or other nanoparticles or spherical shells, and probes labeled with any other signal generating label known to those of skill in the art. Non-limiting examples of label moieties useful for detection in the invention include, without limitation, suitable enzymes such as horseradish peroxidase, alkaline phosphatase, β-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue™, Texas Red, dichlorotriazinylamine fluorescein, dansyl chloride, phycoerythrin, fluorescent lanthanide complexes such as those including Europium and Terbium, Cy3, Cy5, molecular beacons and fluorescent derivatives thereof, as well as others known in the art as described, for example, in *Principles of Fluorescence Spectroscopy*, Joseph R. Lakowicz (Editor), Plenum Pub Corp, 2nd edition (July 1999) and the 6th Edition of the *Molecular Probes Handbook* by Richard P. Hoagland; a luminescent material such as luminol; light scattering or plasmon resonant materials such as gold or silver particles or quantum dots; or radioactive material include $^{14}C$, $^{123}I$, $^{124}I$, $^{125}I$, $^{131}I$, Tc99m, $^{35}S$ or $^3H$.

As used herein, the term "typable loci" is intended to mean sequence-specific locations in a nucleic acid. The term can include pre-determined or predicted nucleic acid sequences expected to be present in isolated nucleic acid molecules. The term typable loci is meant to encompass single nucleotide polymorphisms (SNPs), mutations, variable number of tandem repeats (VNTRs) and single tandem repeats (STRs), other polymorphisms, insertions, deletions, splice variants or any other known genetic markers. Exemplary resources that provide known SNPs and other genetic variations include, but are not limited to, the dbSNP administered by the NCBI and available online at ncbi.nlm.nih.gov/SNP/ and the HCV-BASE database described in Fredman et al. *Nucleic Acids Research,* 30:387-91, (2002) and available online at hgv-base.cgb.ki.se/.

As used herein, the term "representationally amplifying" is intended to mean replicating a nucleic acid template to produce a nucleic acid copy in which the proportion of each sequence in the copy relative to all other sequences in the copy is substantially the same as the proportions in the nucleic acid template. A nucleic acid template included in the term can be a single molecule such as a chromosome or a plurality of molecules such as a collection of chromosomes making up a genome or portion of a genome. Similarly, a nucleic acid copy can be a single molecule or plurality of molecules. The nucleic acids can be DNA or RNA or mimetics or derivatives thereof. A copy nucleic acid can be a plurality of fragments that are smaller than the template DNA. Accordingly, the term can include replicating a genome, or portion thereof, such that the proportion of each resulting genome fragment to all other genome fragments in the population is substantially the same as the proportion of its sequence to other genome fragment sequences in the genome. The DNA being replicated can be isolated from a tissue or blood sample, from a forensic sample, from a formalin-fixed cell, or from other sources. A genomic DNA used in the invention can be intact, largely intact or fragmented. A nucleic acid molecule, such as a template or a copy thereof can be any of a variety of sizes including, without limitation, at most about 1 mb, 0.5 mb, 0.1 mb, 50 kb, 10 kb, 5 kb, 3 kb, 2 kb, 1 kb, 0.5 kb, 0.25, 0.1.0.05 or 0.02 kb.

Accordingly, the term "amplified representative" is intended to mean a nucleic acid copy in which the proportion of each sequence in the copy relative to all other sequences in the copy is substantially the same as the proportions in the nucleic acid template. When used in reference to a population of genome fragments, for example, the term is intended to mean a population of genome fragments in which the proportion of each genome fragment to all other genome fragments in the population is substantially the same as the proportion of its sequence to the other genome fragment sequences in the genome. Substantial similarity between the proportion of sequences in an amplified representation and a template genomic DNA means that at least 60% of the loci in the representation are no more than 5 fold over-represented or under-represented. In such representations at least 70%, 80%, 90%, 95% or 99% of the loci can be, for example, no more than 5, 4, 3 or 2 fold over-represented or under-represented. A nucleic acid included in the term can be DNA, RNA or an analog thereof. The number of copies of each nucleic acid sequence in an amplified representative population can be, for example, at least 2, 5, 10, 25, 50, 100, 1000, $1\times10^4$, $1\times10^5$, $1\times10^6$, $1\times10^7$, $1\times10^8$ or $1\times10^{10}$ fold more than the template or more.

Exemplary populations of genome fragments that include sequences identical to a portion of a genome include, for example, high complexity representations or low complexity representations. As used herein, the term "high complexity representation" is intended to mean a nucleic acid copy having at least about 50% of the sequence of its template. Thus a high complexity representation of a genomic DNA can include, without limitation at least about 60%, 70%, 75%, 80%, 85%, 90%, 95% or 99% of the template genome sequence. As used herein, the term "low complexity representation" is intended to mean a nucleic acid copy having at most about 49% of the sequence of its template. Thus, a low complexity representation of a genomic DNA can include, without limitation, at most about 49%, 40%, 30%, 20%, 10%, 5% or 1% of the genome sequence. In particular embodiments, a population of genome fragments of the invention can have a complexity representing at least about 5%, 10%, 20%, 30%, or 40% of the genome sequence.

As used herein, the term "directly detecting," when used in reference to a nucleic acid, is intended to mean perceiving or discerning a property of the nucleic acid in a sample based on the level of the nucleic acid in the sample. The term can include, for example, perceiving or discerning a property of a nucleic acid in a sample without amplifying the nucleic acid in the sample, or detection without amplification. An exemplary property that can be perceived or discerned includes, without limitation, a nucleotide sequence, the presence of a particular nucleotide such as a polymorphism or mutation at a particular site in a sequence, or the like. One non-limiting example of a direct detection method is the detection of a nucleic acid by hybridizing a labeled probe to the nucleic acid and determining the presence of the nucleic acid based on presence of the hybridized label. Other examples of direct detection are described herein and include, for example, single base extension (SBE) and allele-specific primer extension (ASPE). Those skilled in the art will understand that following detection, a sample of unamplified nucleic acid, such as a sample of unamplified genomic DNA fragments, can be amplified.

In particular embodiments, direct detection can include generating a double-stranded nucleic acid complex between a typable locus and its complementary sequence and perceiving the complex without generating additional copies of the typable locus. In some embodiments, direct detection of a typable locus can involve formation of a single hybridization complex thereby excluding repeated hybridization to a particular nucleic acid molecule having the typable locus.

A method of detecting a detectable position, such as a typable locus or sequence genetically linked to a typable locus can include, for example, hybridization by an oligonucleotide to the interrogation position, or hybridization by an oligonucleotide nearby or adjacent to the interrogation position, followed by extension of the hybridized oligonucleotide across the interrogation position.

Several direct detection methods useful in the invention and described herein, including, without limitation, SBE and ASPE, employ probes that both capture a genome fragment and produce a signal indicative of the presence of a particular SNP locus on the fragment. In particular, a method of the invention can be carried out under conditions in which detection of a SNP or other feature of a captured oligonucleotide, such as a genome fragment, does not require an exogenously added query oligonucleotide. However, if desired, exogenously added query oligonucleotides can be used. Exemplary methods employing exogenously added query oligonucleotides are set forth below such as oligo ligation assay (OLA), extension ligation (GOLDENGATE®), rolling circle-based detection methods, allele-specific oligonucleotide (ASO) hybridization and others.

As used herein, the term "amplify," when used in reference to a single stranded nucleic acid, is intended to mean producing one or more copies of the single stranded nucleic acid, or a portion thereof.

As used herein, the term "genome fragment" is intended to mean an isolated nucleic acid molecule having a sequence that is substantially identical to a portion of a chromosome. A chromosome is understood to be a linear or sometimes circular DNA-containing body of a virus, prokaryotic organism, or eukaryotic nucleus that contains most or all of the replicated genes. A population of genome fragments can include sequences identical to substantially an entire genome or a portion thereof. A genome fragment can have, for example, a sequence that is substantially identical to at least about 25, 50, 70, 100, 200, 300, 400, 500, 600, 700, 800, 900 or 1000 or more nucleotides of a chromosome. A genome fragment can be DNA, RNA, or an analog thereof. It will be understood by those skilled in the art that an RNA sequence and DNA chromosome sequence that differ by the presence of uracils in place of thymines are substantially identical in sequence.

As used herein, the term "native," when used in reference to a genome, is intended to mean produced by isolation from a cell or other host. The term is intended to exclude genomes that are produced by in vitro synthesis, replication or amplification.

As used herein, the term "corresponding to," when used in reference to a typable locus, is intended to mean having a nucleotide sequence that is identical or complimentary to the sequence of the typable locus, or a diagnostic portion thereof. Exemplary diagnostic portions include, for example, nucleic acid sequences adjacent or near to the typable locus of interest.

As used herein, the term "multiplex" is intended to mean simultaneously conducting a plurality of assays on one or more sample. Multiplexing can further include simultaneously conducting a plurality of assays in each of a plurality of separate samples. For example, the number of reaction mixtures analyzed can be based on the number of wells in a multi-well plate and the number of assays conducted in each well can be based on the number of probes that contact the contents of each well. Thus, 96 well, 384 well or 1536 well microtiter plates will utilize composite arrays comprising 96, 384 and 1536 individual arrays, although as will be appreciated by those in the art, not each microtiter well need contain an individual array. Depending on the size of the microtiter plate and the size of the individual array, very high numbers of assays can be run simultaneously; for example, using individual arrays of 2,000 and a 96 well microtiter plate, 192,000 experiments can be done at once; the same arrays in a 384 microtiter plate yields 768,000 simultaneous experiments, and a 1536 microtiter plate gives 3,072,000 experiments. Although multiplexing has been exemplified with respect to microtiter plates, it will be understood that other formats can be used for multiplexing including, for example, those described in US 2002/0102578 A1.

As used herein, the term "polymerase" is intended to mean an enzyme that produces a complementary replicate of a nucleic acid molecule using the nucleic acid as a template strand. DNA polymerases bind to the template strand and then move down the template strand adding nucleotides to the free hydroxyl group at the 3' end of a growing chain of nucleic acid. DNA polymerases synthesize complementary DNA molecules from DNA or RNA templates and RNA polymerases synthesize RNA molecules from DNA templates (transcription). DNA polymerases generally use a short, preexisting RNA or DNA strand, called a primer, to begin chain growth. Some DNA polymerases can only replicate single-stranded templates, while other DNA polymerases displace the strand upstream of the site where they are adding bases to a chain. As used herein, the term "strand displacing," when used in reference to a polymerase, is intended to mean having an activity that removes a complementary strand from a template strand being read by the polymerase. Exemplary polymerases having strand displacing activity include, without limitation the large fragment of Bst (*Bacillus stearothermophilus*) polymerase, exo⁻ Klenow polymerase or sequencing grade T7 exo-polymerase.

Further, some DNA polymerases degrade the strand in front of them, effectively replacing it with the growing chain behind. This is known as an exonuclease activity. Some DNA polymerases in use commercially or in the lab have been modified, either by mutation or otherwise, to reduce or eliminate exonuclease activity. Further mutations or modification are also frequently performed to improve the ability of the DNA polymerase to use non-natural nucleotides as substrates.

As used herein, the term "processivity" refers to the number of bases, on average, added to a nucleic acid being synthesized by a polymerase prior to the polymerase detaching from the template nucleic acid being replicated. Polymerases of low processivity, on average, synthesize shorter nucleic acid chains compared to polymerases of high processivity. A polymerase of low processivity will synthesize, on the average, a nucleic acid that is less than about 100 bases in length prior to detaching from the template nucleic acid being replicated. Further exemplary average lengths for a nucleic acid synthesized by a low processivity polymerase prior to detaching from the template nucleic acid being replicated include, without limitation, less than about 80, 50, 25, 10 or 5 bases.

As used herein, the term "nicked," when used in reference to a double-stranded nucleic acid, is intended to mean lacking at least one covalent bond of the backbone connecting adjacent sequences in a first strand and having a complimentary second strand hybridized to both of the adjacent sequences in the first strand.

As used herein, the term "nicking agent" is intended to mean a physical, chemical, or biochemical entity that cleaves a covalent bond connecting adjacent sequences in a first nucleic acid strand, thereby producing a product in which the adjacent sequences are hybridized to the same complementary strand. Exemplary nicking agents include, without limitation, single strand nicking restriction endonucleases that recognize a specific sequence such as N.BstNBI, MutH or geneII protein of bacteriophage f1; DNAse I; chemical reagents such as free radicals; or ultrasound.

As used herein, the term "isolated," when used in reference to a biological substance, is intended to mean removed from at least a portion of the molecules associated with or occurring with the substance in its native environment. Accordingly, the term "isolating," when used in reference to a biological substance, is intended to mean removing the substance from its native environment or removing at least a portion of the molecules associated with or occurring with the nucleic acid or substance in its native environment. Exemplary substances that can be isolated include, without limitation, nucleic acids, proteins, chromosomes, cells, tissues or the like. An isolated biological substance, such as a nucleic acid, can be essentially free of other biological substances. For example, an isolated nucleic acid can be at least about 90%, 95%, 99% or 100% free of non-nucleotide material naturally associated with it. An isolated nucleic acid can, for example, be essentially free of other nucleic acids such that its sequence is increased to a significantly higher fraction of the total nucleic acid present in the solution of interest than in the cells from which the sequence was taken. For example, an isolated nucleic acid can be present at a 2, 5, 10, 50, 100 or 1000 fold or higher level than other nucleic acids in vitro relative to the levels in the cells from which it was taken. This could be caused by preferential reduction in the amount of other DNA or RNA present, or by a preferential increase in the amount of the specific DNA or RNA sequence, or by a combination of the two.

As used herein, the term "complexity," when used in reference to a nucleic acid sequence, is intended to mean the total length of unique sequence in a genome. The complexity of a genome can be equivalent to or less than the length of a single copy of the genome (i.e. the haploid sequence). Estimates of genome complexity can be less than the total length if adjusted for the presence of repeated sequences. The length of repeated sequences used for such estimates can be adjusted to suit a particular analysis. For example, complexity can be the sum of the number of unique sequence words in a haploid genome sequence plus the length of the sequence word. A sequence word is a continuous sequence of a defined length of at least 10 nucleotides. The number of repeat sequences, and thus, the length of unique sequence, in a genome will depend upon the length of the sequence word. More specifically, as the length of the sequence word is increased to, for example, 15, 20, 25, 30, 50, 100 or more nucleotides, the complexity estimate will generally increase approaching the upper limit of the length of the haplotype genome.

DETAILED DESCRIPTION OF THE INVENTION

One object of the invention is to provide a sensitive and accurate method for simultaneously interrogating a plurality of gene loci in a DNA sample. In particular, a method of the invention can be used to determine the genotype of an individual by direct detection of a plurality of single nucleotide polymorphisms in a sample of the individual's genomic DNA or cDNA. An advantage of the invention is that a small amount of genomic DNA can be obtained from an individual, and amplified to obtain an amplified representative population of genome fragments that can be interrogated in the methods of the invention. Thus, the methods are particularly useful for genotyping genomic DNA obtained from relatively small tissue samples such as a biopsy or archived sample. Generally, the methods will be used to amplify a relatively small number of template genome copies. In particular embodiments, a genomic DNA sample can be obtained from a single cell and genotyped.

A further advantage of direct detection of genetic loci in the methods of the invention is that a target genomic DNA fragment need not be amplified once it has been captured by an appropriate probe. Thus, the methods can provide the advantage of reducing or obviating the need for elaborate and expensive means for detection following capture. If sufficient DNA is present, the detection of typable loci can be conducted by a technique that does not require amplification of a captured target such as single base extension (SBE) or allele specific primer extension (ASPE). Other methods of direct detection include ligation, extension-ligation, invader assay, hybridization with a labeled complementary sequence, or the like. Such direct detection techniques can be carried out, for example, directly on a captured probe-target complex as set forth below. Although target amplification-based detection methods are not required in the methods of the invention, the methods are compatible with a variety of amplification based detection methods such as Invader, PCR-based, or oligonucleotide ligation assay-based (OLA-based) technologies which can be used, if desired.

The invention provides methods of whole genome amplification that can be used to amplify genomic DNA prior to genetic evaluation such as detection of typable loci in the genome. Whole genome amplification methods of the invention can be used to increase the quantity of genomic DNA without compromising the quality or the representation of any given sequence. Thus, the methods can be used to amplify a relatively small quantity of genomic DNA in a sequence independent fashion to provide levels of the genomic DNA that can be genotyped. Surprisingly, a complex genome can be amplified with a low processivity polymerase to obtain a population of genome fragments that is representative of the genome, has high complexity and contains fragments that have a convenient size for hybridization to a typical nucleic acid array.

As set forth in further detail below, a complex representative population of genome fragments can be incubated with a plurality of probes and a relatively small fraction of these fragments, having loci of interest, specifically detected despite the presence substantially large amount of other genomic sequences present in the population of fragments. Moreover, specific detection can occur for such complex representations even if probe hybridization is carried out with large amounts and high concentrations of the genome fragment populations. Thus, an advantage of the invention is that whole genome genotyping can be carried out in the presence of a high complexity genomic DNA background.

Furthermore, amplification of genomic DNA in the methods disclosed herein does not require the polymerase chain reaction. Specifically, amplification can be carried out such that sequences are amplified several fold under isothermal conditions. Thus, although an elevated temperature step can be used, for example, to initially denature a genomic DNA template, temperature cycling need not be used. Accordingly, repeated increases in temperature, normally used to denature hybrids, and repeated return to hybridization temperatures need not be used.

After capture and separation of the typable loci on an array, the individual typable loci can be scored in positus (in place) via a subsequent detection assay such as ASPE or SBE. Thus, a population of genome fragments obtained by whole genome amplification with a low processivity polymerase can be captured by an array of probes and the genotype of the genome determined based on the typable loci detected individually at each probe as set forth below and demonstrated in the Examples. An in positus genotyping approach has remarkable advantages in that it allows extensive multiplexing of the assay where desired.

The use of high density DNA array technology for detection of typable loci in a whole genome or complex DNA sample, such as a cDNA sample, can be facilitated by the amplification methods of the invention because the method can produce a number of copies of typable loci, or sequences complementary to typable loci to scale in relative proportion to their representation in the template sample. Maintaining relatively uniform representation is advantageous in many applications because if some areas of the genome containing specific genetic markers are not faithfully replicated, they will not be detected in an assay adjusted for the average amplification.

The invention can by scaled to detect a desired number of typable loci simultaneously or sequentially as desired. The methods can be used to simultaneously detect at least 10 typable loci, at least 100, 1000, $1 \times 10^4$, $1 \times 10^5$, $1 \times 10^6$, $1 \times 10^7$ typable loci or more. Similarly, these numbers of typable loci can be determined in a sequential format where desired. Thus, the invention can be used to genotype individuals on a genome-wide scale if desired.

The whole genome amplification methods of the invention and whole genome genotyping methods of the invention are useful, alone or in combination, in a number of applications including, for example, single cell sperm haplotype analysis, genotyping of large numbers of individuals in a high-throughput format, or identification of new haplotypes. Furthermore, the invention reduces the amount of DNA or RNA sample required in many current array assays. Further still, improved array sensitivity available with the invention can lead to reduced sample requirements, improved LOD scoring ability, and greater dynamic range.

The invention can be used to identify new markers or haplotypes that are diagnostic of traits such as those listed above. Such studies can be carried out by comparing genotypes for groups of individuals having a shared trait or set of traits with a control group lacking the trait based on the expectation that there will be higher frequencies of the contributing genetic components in a group of people with a shared trait, such as a particular disease or response to a drug, vaccine, pathogen, or environmental factor, than in a group of similar people without the disease or response. Accordingly the methods of the invention can be used to find chromosome regions that have different haplotype distributions in the two groups of people, those with a disease or response and those without. Each region can then be studied in more detail to discover which variants in which genes in the region contribute to the disease or response, leading to more effective interventions. This can also allow the development of tests to predict which drugs or vaccines are effective in individuals with particular genotypes for genes affecting drug metabolism. Thus, the invention can be used to determine the genotype of an individual based on identification of which genetic markers are found in the individual's genome. Knowledge of an individual's genotype can be used to determine a variety of traits such as response to environmental factors, susceptibility to infection, effectiveness of particular drugs or vaccines or risk of adverse responses to drugs or vaccines.

The invention is exemplified herein with respect to amplification and/or detection of typable loci for a whole genome. Those skilled in the art will recognize from the teaching herein that the methods can also be used with other complex nucleic acid samples including, for example, a fraction of a genome, such as a chromosome or subset of chromosomes; a sample having multiple different genomes, such as a biopsy sample having genomic DNA from a host as well as one or more parasite or an ecological sample having multiple organisms from a particular environment; or even cDNA or an amplified cDNA representation. Accordingly, the methods can be used to characterize typable loci found in a fraction of a genome or in a mixed genome sample. The invention provides a method of detecting one or several typable loci contained within a given genome. The method includes the steps of (a) providing an amplified representative population of genome fragments having such typable loci; (b) contacting the genome fragments with a plurality of nucleic acid probes having sequences corresponding to the typable loci under conditions wherein probe-fragment hybrids are formed; and (c) detecting typable loci of the probe-fragment hybrids. In particular embodiments these nucleic acid probes are at most 125 nucleotides in length. FIG. 1 shows a general overview of an exemplary method of detecting typable loci of a genome. As shown in FIG. 1, a population of genome fragments can be obtained from a genome, denatured and contacted with an array of nucleic acid probes each having a sequence that is complementary to a particular typable locus of the genome. Genome fragments having typable loci represented on the probes are captured as probe-fragment hybrids at discrete locations on the array while other fragments lacking loci of interest will remain in bulk solution. The probe-fragment hybrids can be detected by enzyme-mediated addition of a detection moiety (referred to as a signal moiety in FIG. 1) to the probe. In the exemplary embodiment of FIG. 1, a polymerase selectively adds a biotin labeled nucleotide to probes in probe-fragment hybrids. The biotinylated probes can then be detected, for example, by contacting a fluorescently labeled avidin to the array under conditions where biotinylated probes are selectively bound and detecting the locations in the array that fluoresce. Based on the known sequences for probes at each location, the presence of particular typable loci can be determined.

A method of the invention can be used to amplify genomic DNA (gDNA) or detect typable loci of a genome from any organism. The methods are ideally suited to the amplification and analysis of large genomes such as those typically found in eukaryotic unicellular and multicellular organisms. Exemplary eukaryotic gDNA that can be used in a method of the invention includes, without limitation, that from a mammal such as a rodent, mouse, rat, rabbit, guinea pig, ungulate, horse, sheep, pig, goat, cow, cat, dog, primate, human or non-human primate; a plant such as *Arabidopsis thaliana*, corn (*Zea mays*), sorghum, oat (*oryza sativa*), wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish (*Danio rerio*); a reptile; an amphibian such as a frog or *Xenopus laevis*; a *dictyostelium discoideum*; a fungi such as *pneumocystis carinii, Takifugu rubripes*, yeast, *Saccharamoyces cerevisiae* or *Schizosaccharomyces pombe*; or a *plasmodium falciparum*. A method of the invention can also be used to detect typable loci of smaller genomes such as those from a prokaryote such as a bacterium, *Escherichia coli*, staphylococci or *mycoplasma pneumoniae*; an archae; a virus such as Hepatitis C virus or human immunodeficiency virus; or a viroid.

A genomic DNA used in the invention can have one or more chromosomes. For example, a prokaryotic genomic DNA including one chromosome can be used. Alternatively, a eukaryotic genomic DNA including a plurality of chromosomes can be used in a method of the invention. Thus, the methods can be used, for example, to amplify or detect typable loci of a genomic DNA having n equal to 2 or more, 4 or more, 6 or more, 8 or more, 10 or more, 15 or more, 20 or more, 23 or more, 25 or more, 30 or more, or 35 or more chromosomes, where n is the haploid chromosome number and the diploid chromosome count is 2 n. The size of a genomic DNA used in a method of the invention can also be measured according to the number of base pairs or nucleotide length of the chromosome complement. Exemplary size estimates for some of the genomes that are useful in the invention are about 3.1 Gbp (human), 2.7 Gbp (mouse), 2.8 Gbp (rat), 1.7 Gbp (zebrafish), 165 Mbp (fruitfly), 13.5 Mbp (*S. cerevisiae*), 390 Mbp (fugu), 278 Mbp (mosquito) or 103 Mbp (*C. elegans*). Those skilled in the art will recognize that genomes having sizes other than those exemplified above including, for example, smaller or larger genomes, can be used in a method of the invention.

Genomic DNA can be isolated from one or more cells, bodily fluids or tissues. Known methods can be used to obtain a bodily fluid such as blood, sweat, tears, lymph, urine, saliva, semen, cerebrospinal fluid, feces or amniotic fluid. Similarly known biopsy methods can be used to obtain cells or tissues such as buccal swab, mouthwash, surgical removal, biopsy aspiration or the like. Genomic DNA can also be obtained from one or more cell or tissue in primary culture, in a propagated cell line, a fixed archival sample, forensic sample or archeological sample.

Exemplary cell types from which gDNA can be obtained in a method of the invention include, without limitation, a blood cell such as a B lymphocyte, T lymphocyte, leukocyte, erythrocyte, macrophage, or neutrophil; a muscle cell such as a skeletal cell, smooth muscle cell or cardiac muscle cell; germ cell such as a sperm or egg; epithelial cell; connective tissue cell such as an adipocyte, fibroblast or osteoblast; neuron; astrocyte; stromal cell; kidney cell; pancreatic cell; liver cell; or keratinocyte. A cell from which gDNA is obtained can be at a particular developmental level including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Other cells include a bone marrow stromal cell (mesenchymal stem cell) or a cell that develops therefrom such as a bone cell (osteocyte), cartilage cells (chondrocyte), fat cell (adipocyte), or other kinds of connective tissue cells such as one found in tendons; neural stem cell or a cell it gives rise to including, for example, a nerve cells (neuron), astrocyte or oligodendrocyte; epithelial stem cell or a cell that arises from an epithelial stem cell such as an absorptive cell, goblet cell, Paneth cell, or enteroendocrine cell; skin stem cell; epidermal stem cell; or follicular stem cell. Generally any type of stem cell can be used including, without limitation, an embryonic stem cell, adult stem cell, or pluripotent stem cell.

A cell from which a gDNA sample is obtained for use in the invention can be a normal cell or a cell displaying one or more symptom of a particular disease or condition. Thus, a gDNA used in a method of the invention can be obtained from a cancer cell, neoplastic cell, necrotic cell or the like. Those skilled in the art will know or be able to readily determine methods for isolating gDNA from a cell, fluid or tissue using methods known in the art such as those described in Sambrook et al., *Molecular Cloning: A Laboratory Manual,* 3rd edition, Cold Spring Harbor Laboratory, New York (2001) or in Ausubel et al., *Current Protocols in Molecular-Biology,* John Wiley and Sons, Baltimore, Md. (1998).

A method of the invention can further include steps of isolating a particular type of cell or tissue. Exemplary methods that can be used in a method of the invention to isolate a particular cell from other cells in a population include, but are not limited to, Fluorescent Activated Cell Sorting (FACS) as described, for example, in Shapiro, *Practical Flow Cytometry, 3rd edition* Wiley-Liss; (1995), density gradient centrifugation, or manual separation using micromanipulation methods with microscope assistance. Exemplary cell separation devices that are useful in the invention include, without limitation, a Beckman JE-6 centrifugal elutriation system, Beckman Coulter EPICS ALTRA computer-controlled Flow Cytometer-cell sorter, Modular Flow Cytometer from Cytomation, Inc., Coulter counter and channelyzer system, density gradient apparatus, cytocentrifuge, Beckman J-6 centrifuge, EPICS V dual laser cell sorter, or EPICS PROFILE flow cytometer. A tissue or population of cells can also be removed by surgical techniques. For example, a tumor or cells from a tumor can be removed from a tissue by surgical methods, or conversely non-cancerous cells can be removed from the vicinity of a tumor. Using methods such as those set forth in further detail below, the invention can be used to compare typable loci for different cells including, for example, cancerous and non-cancerous cells isolated from the same individual or from different individuals.

A gDNA can be prepared for use in a method of the invention by lysing a cell that contains the DNA. Typically, a cell is lysed under conditions that substantially preserve the integrity of the cell's gDNA. In particular, exposure of a cell to alkaline pH can be used to lyse a cell in a method of the invention while causing relatively little damage to gDNA. Any of a variety of basic compounds can be used for lysis including, for example, potassium hydroxide, sodium hydroxide, and the like. Additionally, relatively undamaged gDNA can be obtained from a cell lysed by an enzyme that degrades the cell wall. Cells lacking a cell wall either naturally or due to enzymatic removal can also be lysed by exposure to osmotic stress. Other conditions that can be used to lyse a cell include exposure to detergents, mechanical disruption, sonication heat, pressure differential such as in a French press device, or Dounce homogenization. Agents that stabilize gDNA can be included in a cell lysate or isolated gDNA sample including, for example, nuclease inhibitors, chelating agents, salts buffers and the like. Methods for lysing a cell to obtain gDNA can be carried out under conditions known in the art as described, for example, in Sambrook et al., supra (2001) or in Ausubel et al., supra, (1998).

In particular embodiments of the invention, a crude cell lysate containing gDNA can be directly amplified or detected without further isolation of the gDNA. Alternatively, a gDNA can be further isolated from other cellular components prior to amplification or detection. Accordingly, a detection or amplification method of the invention can be carried out on purified or partially purified gDNA. Genomic DNA can be isolated using known methods including, for example, liquid phase extraction, precipitation, solid phase extraction, chromatography and the like. Such methods are often referred to as minipreps and are described for example in Sambrook et al., supra, (2001) or in Ausubel et al., supra, (1998) or available from various commercial vendors including, for example, Qiagen (Valencia, Calif.) or Promega (Madison, Wis.).

An amplified representative population of genome fragments can be provided by amplifying a native genome under conditions that replicate a genomic DNA (gDNA) template to produce one or more copies in which the relative proportion of each copied sequence is substantially the same as its proportion in the original gDNA. Thus, a method of the invention can include a step of representationally amplifying a native genome. Any of a variety of methods that replicate genomic DNA in a sequence independent fashion can be used in the invention.

A method of the invention can be used to produce an amplified representative population of genome fragments from a small number of genome copies. Accordingly, small tissue samples or other samples having relatively few cells, for example, due to low abundance, biopsy constraints or high cost, can be genotyped or evaluated on a genome-wide scale. The invention can be used to produce an amplified representative population of genome fragments from a single native genome copy obtained, for example, from a single cell. In other exemplary embodiments of the invention, an amplified representative population of genome fragments can be produced from larger number of copies of a native genome including, but not limited to, about 1,000 copies (for a human genome, approximately 3 nanograms of DNA) or fewer, 10,000 copies or fewer, $1 \times 10^5$ copies (for a human genome, approximately 300 nanograms of DNA) or fewer, $5 \times 10^5$ copies or fewer, $1 \times 10^6$ copies or fewer, $1 \times 10^8$ copies or fewer, $1 \times 10^{10}$ copies or fewer, or $1 \times 10^{12}$ copies or fewer.

A DNA sample that is representationally amplified in the invention can be a genome such as those set forth above or other DNA templates such as mitochondrial DNA or some subset of genomic DNA. One non-limiting example of a subset of genomic DNA is one particular chromosome or one region of a particular chromosome. In general, an amplification method used in the invention can be carried out using at least one primer nucleic acid that hybridizes to a template nucleic acid to form a hybridization complex, nucleotide triphosphates (NTPs) and a polymerase which modifies the primer by reacting the NTPs with the 3' hydroxyl of the primer thereby replicating at least a portion of the template. For example, PCR based methods generally utilize a DNA template, two primers, dNTPs and a DNA polymerase. Thus, in a typical whole genome amplification method of the invention, a genomic DNA sample is incubated with a reaction mixture that includes amplification components such as those set forth above, and an amplified representative population of genome fragments is formed.

A primer used in a method of the invention can have any of a variety of compositions or sizes, so long as it has the ability to hybridize to a template nucleic acid with sequence specificity and can participate in replication of the template. For example, a primer can be a nucleic acid having a native structure or an analog thereof. A nucleic acid with a native structure generally has a backbone containing phosphodiester bonds and can be, for example, deoxyribonucleic acid or ribonucleic acid. An analog structure can have an alternate backbone including, without limitation, phosphoramide (see, for example, Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (see, for example, Mag et al., *Nucleic Acids Res.* 19:1437 (1991); and U.S. Pat. No. 5,644,048), phosphorodithioate (see, for example, Briu et al., *J. Am. Chem. Soc.* 11 1:2321 (1989), O-methylphophoroamidite linkages (see, for example, Eckstein, *Oligonucleotides and Analogues: A Practical Approach*, Oxford University Press), and peptide nucleic acid backbones and linkages (see, for example, Egholm, *J. Am. Chem. Soc.* 114: 1895 (1992); Meier et al., *Chem. Int. Ed. Engl.* 31:1008 (1992); Nielsen, *Nature*, 365:566 (1993); Carlsson et al., *Nature* 380:207 (1996)). Other analog structures include those with positive backbones (see, for example, Denpcy et al., *Proc. Natl. Acad. Sci. USA* 92:6097 (1995); non-ionic backbones (see, for example, U.S. Pat. Nos. 5,386,023, 5,637, 684, 5,602,240, 5,216,141 and 4,469,863; Kiedrowski et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Left.* 4:395 (1994); Jeffs et al., *J. Biomolecular NMR* 34:17 (1994); *Tetrahedron Lett.* 37:743 (1996)) and non-ribose backbones, including, for example, those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Analog structures containing one or more carbocyclic sugars are also useful in the methods and are described, for example, in Jenkins et al., *Chem. Soc. Rev.* (1995) pp 169-176. Several other analog structures that are useful in the invention are described in Rawls, *C & E News Jun.* 2, 1997 page 35.

A further example of a nucleic acid with an analog structure that is useful in the invention is a peptide nucleic acid (PNA). The backbone of a PNA is substantially non-ionic under neutral conditions, in contrast to the highly charged phosphodiester backbone of naturally occurring nucleic acids. This provides two non-limiting advantages. First, the PNA backbone exhibits improved hybridization kinetics. Secondly, PNAs have larger changes in the melting temperature ($T_m$) for mismatched versus perfectly matched base pairs. DNA and RNA typically exhibit a 2-4° C. drop in $T_m$ for an internal mismatch. With the non-ionic PNA backbone, the drop is closer to 7-9° C. This can provide for better sequence discrimination. Similarly, due to their non-ionic nature, hybridization of the bases attached to these backbones is relatively insensitive to salt concentration.

A nucleic acid useful in the invention can contain a non-natural sugar moiety in the backbone. Exemplary sugar modifications include but are not limited to 2' modifications such as addition of halogen, alkyl, substituted alkyl, allcaryl, arallcyl, O-allcaryl or O-aralkyl, SH, SCH3, OCN, Cl, Br, CN, CF3, OCF3, SOCH3, S02 CH3, ON02, $NO_2$, N3, NH2, heterocycloallcyl, heterocycloallcaryl, aminoallcylamino, polyallcylamino, substituted silyl, and the like. Similar modifications can also be made at other positions on the sugar, particularly the 3' position of the sugar on the 3' terminal nucleotide or in 2'-5' linked oligonucleotides and the 5' position of 5' terminal nucleotide.

A nucleic acid used in the invention can also include native or non-native bases. In this regard a native deoxyribonucleic acid can have one or more bases selected from the group consisting of adenine, thymine, cytosine or guanine and a ribonucleic acid can have one or more bases selected from the group consisting of uracil, adenine, cytosine or guanine. Exemplary non-native bases that can be included in a nucleic acid, whether having a native backbone or analog structure, include, without limitation, inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

A non-native base used in a nucleic acid of the invention can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine which base pairs with cytosine, adenine or uracil.

A nucleic acid having a modified or analog structure can be used in the invention, for example, to facilitate the addition of labels, or to increase the stability or half-life of the molecule under amplification conditions or other conditions used in accordance with the invention. As will be appreciated by those skilled in the art, one or more of the above-described nucleic acids can be used in the present invention, including, for example, as a mixture including molecules with native or analog structures. In addition, a nucleic acid primer used in the invention can have a structure desired for a particular amplification technique used in the invention such as those set forth below.

In particular embodiments a nucleic acid useful in the invention can include a detection moiety. A detection moiety can be used, for example, to detect one or more members of an amplified representative population of genome fragments using methods such as those set forth below. A detection moiety can be a primary label that is directly detectable or secondary label that can be indirectly detected, for example, via direct or indirect interaction with a primary label. Exemplary primary labels include, without limitation, an isotopic label such as a naturally non-abundant radioactive or heavy isotope; chromophore; luminophore; fluorophore; calorimetric agent; magnetic substance; electron-rich material such as a metal; electrochemiluminescent label such as $Ru(bpy)_3^{2+}$; or moiety that can be detected based on a nuclear magnetic, paramagnetic, electrical, charge to mass, or thermal characteristic. Fluorophores that are useful in the invention include, for example, fluorescent lanthanide complexes, including those of Europium and Terbium, fluorescein, rhodamine, tetramethylrhodamine, eosin, erythrosin, coumarin, methylcoumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, *Molecular Probes Handbook*, (Eugene, Oreg.) 6th Edition; The Synthegen catalog (Houston, Tex.), Lakowicz, *Principles of Fluorescence Spectroscopy*, 2nd Ed., Plenum Press New York (1999), or WO 98/59066. Labels can also include enzymes such as horseradish peroxidase or alkaline phosphatase or particles such as magnetic particles or optically encoded nanoparticles.

Exemplary secondary labels are binding moieties. A binding moiety can be attached to a nucleic acid to allow detection or isolation of the nucleic acid via specific affinity for a receptor. Specific affinity between two binding partners is understood to mean preferential binding of one partner to another compared to binding of the partner to other components or contaminants in the system. Binding partners that are specifically bound typically remain bound under the detection or separation conditions described herein, including wash steps to remove non-specific binding. Depending upon the particular binding conditions used, the dissociation constants of the pair can be, for example, less than about $10^{-4}$, $10^{-5}$, $10^{-6}$, $10^{-7}$, $10^{-8}$, $10^{-9}$, $10^{-10}$, $10^{-11}$, or $10^{-12}$ $M^{-1}$.

Exemplary pairs of binding moieties and receptors that can be used in the invention include, without limitation, antigen and immunoglobulin or active fragments thereof, such as FAbs; immunoglobulin and immunoglobulin (or active fragments, respectively); avidin and biotin, or analogs thereof having specificity for avidin such as imino-biotin; streptavidin and biotin, or analogs thereof having specificity for streptavidin such as imino-biotin; carbohydrates and lectins; and other known proteins and their ligands. It will be understood that either partner in the above-described pairs can be attached to a nucleic acid and detected or isolated based on binding to the respective partner. It will be further understood that several moieties that can be attached to a nucleic acid can function as both primary and secondary labels in a method of the invention. For example, strepatvidin-phycoerythrin can be detected as a primary label due to fluorescence from the phycoerythrin moiety or it can be detected as a secondary label due to its affinity for anti-streptavidin antibodies, as set forth in further detail below in regard to signal amplification methods.

In a particular embodiment, the secondary label can be a chemically modifiable moiety. In this embodiment, labels having reactive functional groups can be incorporated into a nucleic acid. The functional group can be subsequently covalently reacted with a primary label. Suitable functional groups include, but are not limited to, amino groups, carboxy groups, maleimide groups, oxo groups and thiol groups. Binding moieties can be particularly useful when attached to primers used for amplification of a gDNA because an amplified representative population of genome fragments produced with such primers can be attached to an array via said binding moieties. Furthermore, binding moieties can be useful for separating amplified fragments from other components of an amplification reaction, concentrating the amplified representative population of genome fragments, or detecting one or more members of an amplified representative population of genome fragments when bound to capture probes on an array. Exemplary separation and detection methods for nucleic acids having attached binding moieties are set forth below in further detail.

A binding moiety, detection moiety or any other useful moiety can be attached to a nucleic acid such as an amplified genome fragment using methods known in the art. For example, a primer used to amplify a nucleic acid can include the moiety attached to a base, ribose, phosphate, or analogous structure in a nucleic acid or analog thereof. In particular embodiments, a moiety can be incorporated using modified nucleosides that are added to a growing nucleotide strand, for example, during amplification or detection steps. Nucleosides can be modified, for example, at the base or the ribose, or analogous structures in a nucleic acid analog. Thus, a method of the invention can include a step of labeling genome fragments to produce an amplified representative population of genome fragments having one or more of the modifications set forth above.

A nucleic acid primer used to amplify a gDNA in a method of the invention can include a complementary sequence that is any length capable of binding to a template gDNA with sufficient stability and specificity to prime polymerase replication activity. The complementary sequence can include all or a portion of a primer used for amplification. The length of the complementary sequence of a primer used for amplification in a method of the invention will generally be inversely proportional to the distance between priming sites on a gDNA template. Thus, amplification can be carried out with primers having relatively short complementary sequences including, for example, at most 5, 6, 7, 8, 9, 10, 11, 12, 13, 14, 15, 16, 17, 18, 19, 20, 25, 30, 35, 40, 50, 60, 70, 80, 90, 100, 200, 300, 400, 500 nucleotides in length.

Those skilled in the art will recognize that specificity of hybridization is generally increased as the length of the nucleic acid primer is increased. Thus, a longer nucleic acid primer can be used, for example, to increase specificity or reproducibility of replication, if desired. Accordingly, a nucleic acid used in a method of the invention can be at least 5, 6, 7, 8, 9, 10, 11, 12, 13, 14, 15, 16, 17, 18, 19, 20, 25, 30, 35, 40, 50, 60, 70, 80, 90, 100, 200, 300, 400, 500 or more nucleotides long. Those skilled in the art will recognize that a nucleic acid probe used in the invention can also have any of the exemplary lengths set forth above.

Two general approaches to whole genome amplification that can be used in the invention include the use of some form of randomly-primed amplification or creation of a genomic representation amplifiable by universal PCR. Exemplary techniques for randomly-primed amplification include, without limitation, those based upon PCR, such as PEP-PCR or DOP-PCR or those based upon strand-displacement amplification such as random-primer amplification. An exemplary method of creating genomic representations amplifiable by universal PCR is described, for example, in Lucito et al., *Proc. Nat'l. Acad. Sci. USA* 95:4487-4492 (1998). One implementation of genomic representations is to create short genomic inserts (for example, 30-2000 bases) via restriction digestion of gDNA, and add universal PCR tails by adapter ligation. Typically, amplification or detection of gDNA is carried out with a population of nucleic acids that hybridizes to different portions of a gDNA template. A population of nucleic acids used in the invention can include members having a random or semi-random complement of sequences. Thus, a population of nucleic acids can have members with a fixed sequence length in which one or more positions along the sequence are randomized within the population. By way of example, a population of 12mer primers can have a sequence that is identical except at one particular position, say position 5, where any of the four native DNA nucleotides are incorporated, thereby producing a population having four different primer members. In a particular embodiment, multiple positions along the sequence can be combinatorially randomized. For example, a nucleic acid primer can have 2, 5, 10, 15, 20, 25, 30, 35, 40, 50, 60, 70, 80, 90, 100 or more positions that are randomized. For example a 12mer primer that is randomized at each position with 4 possible native DNA nucleotides will contain up to $4^{12}=1.7 \times 10^7$ members.

In particular embodiments, a population of nucleic acids used in the invention can include members with sequences that are designed based on rational algorithms or processes. Similarly, a population of nucleic acids can include members each having at least a portion of their sequence designed based on rational algorithms or processes. Rational design algorithms or processes can be used to direct synthesis of a nucleic acid product having a discrete sequence or to direct synthesis of a nucleic acid mixture that is biased to preferentially contain particular sequences.

Using rational design methods, sequences for nucleic acids in a population can be selected, for example, based on known sequences in the gDNA to be amplified or detected. The sequences can be selected such that the population preferentially includes sequences that hybridize to gDNA with a desired coverage. For example, a population of primers can be designed to preferentially include members that hybridize to a particular chromosome or portion of a gDNA such as coding regions or non coding regions. Other properties of a population of nucleic acids can also be selected to achieve preferential hybridization at positions along a gDNA sequence that are at a desired average, minimum or maximum length from each other. For example, primer length can be selected to hybridize and prime at least about every 64, 256, 1000, 4000, 16000 or more bases from each other along a gDNA sequence.

Nucleic acids useful in the invention can also be designed to preferentially omit or reduce sequences that hybridize to particular sequences in a gDNA to be amplified or detected such as known repeats or repetitive elements including, for example, Alu repeats. Accordingly, a single probe or primer such as one used in arbitrary-primer amplification can be designed to include or exclude a particular sequence. Similarly a population of probes or primers, such as a population of primers used for random primer amplification, can be synthesized to preferentially exclude or include particular sequences such as Alu repeats. A population of random primers can also be synthesized to preferentially include a higher content of G and/or C nucleotides compared to A and T nucleotides. The resulting random primer population will be GC rich and therefore have a higher probability of hybridizing to high GC regions of a genome such as gene coding regions of a human genome which typically have a higher GC content than non-coding gDNA regions. Conversely, AT rich primers can be synthesized to preferentially amplify or anneal to AT rich regions such as non-coding regions of a human genome. Other parameters that can be used to influence nucleic acid design include, for example, preferential removal of sequences that render primers self complementary, prone to formation of primer dimers or prone to hairpin formation or preferential selection of sequences that have a desired maximum, minimum or average $T_m$. Exemplary methods and algorithms that can be used in the invention for designing probes include those described in US 2003/0096986A1.

Primers in a population of random primers can have a region of identical sequence such as a universal tail. A universal tail can include a universal priming site for a subsequent amplification step or a site that anneals to a particular binding agent useful for isolating or detecting amplified sequences. Methods for making and using a population of random primers with universal tails are described, for example, in Singer et al., *Nucl. Acid. Res.* 25:781-786 (1997) or Grothues et al., *Nucl. Acids Res.* 21:1321-2 (1993).

Those skilled in the art will recognize that any of a variety of nucleic acids used in the invention such as probes can have one or more of the properties, or can be produced, as set forth above including in the examples provided with respect to primers.

A method of the invention for amplifying a genome can include a step of contacting a gDNA with a polymerase under conditions for representationally amplifying the genomic DNA. The type of polymerase and conditions used for amplification in a method of the invention can be chosen to obtain genome fragments having a desired length. In particular embodiments, relatively small fragments can be obtained in a method of the invention, for example, by amplifying gDNA with a polymerase of low processivity or by fragmenting a gDNA template or its amplification products with a nucleic acid cleaving agent such as an endonuclease or chemical agent. For example, a method of the invention can be used to obtain an amplified representative population of genome fragments that are, without limitation, at most about 10 kb, 5 kb, 4 kb, 3 kb, 2 kb, 1 kb, 0.8 kb, 0.6 kb, 0.5 kb, 0.4 kb, 0.2 kb, or 0.1 kb in length.

In alternative embodiments, a method of the invention can be used to amplify gDNA to form relatively large genomic DNA fragments. In accordance with such embodiments, a method of the invention can be used to obtain an amplified representative population of genome fragments that are at least about 10 kb, 15 kb, 20 kb, 25 kb, 30 kb or more in length.

An amplified representative population including genome fragments having relatively small size can be obtained, for example, by amplifying the gDNA with a polymerase of low processivity. A low processivity polymerase used in a method of the invention can synthesize less than 100 bases per polymerization event. Shorter fragments can be obtained if desired by using a polymerase that synthesizes less than 50, 40, 30, 20, 10 or 5 bases per polymerization event under the conditions of amplification. A non-limiting advantage of using a low processivity polymerase for amplification is that relatively small fragments are obtained, thereby allowing efficient hybridization to nucleic acid arrays. A low-processivity polymerase can be particularly useful for amplifying a fragmented genome sample. As set forth below, particularly useful methods of individual analysis can include, for example, capture of fragments at discrete locations in an array of probes.

In a particular embodiment, a denatured or single-stranded genomic DNA template can be amplified using a low processivity polymerase in a method of the invention. A gDNA template can be denatured, for example, by heat, enzymes such as helicase, chemical agents such as salt or detergents, pH or the like. Exemplary polymerases that are capable of low processivity and useful for amplifying gDNA in the invention include, without limitation, Taq polymerase, T4 polymerase, "monomeric" *E. coli* Pol III (lacking the beta subunit), or *E. coli* DNA Pol I or its 5' nuclease deficient fragment known as Klenow polymerase.

The invention further provides embodiments in which amplification occurs under conditions where the gDNA template is not denatured. An exemplary condition is a temperature at which an isolated genomic DNA remains substantially double stranded. Conditions in which high temperature denaturation of DNA is not required are typically referred to as isothermal conditions. Genomic DNA can be amplified under isothermal conditions in the invention using a polymerase having strand displacing activity. In particular embodiments, a polymerase having both low processivity and strand displacing activity can be used to obtain an amplified representative population of genome fragments. Exemplary polymerases that are capable of low processivity and strand displacement include, without limitation, *E. coli* Pol I, exo$^-$ Klenow polymerase or sequencing grade T7 exo-polymerase.

Generally, polymerase activity, including, for example, processivity and strand displacement activity, can be influenced by factors such as pH, temperature, ionic strength, and buffer composition. Those skilled in the art will know which types of polymerases and conditions can be used to obtain fragments having a desired length in view of that which is known regarding the activity of the polymerases as described, for example, in Eun, *Enzymology Primer for Recombinant DNA Technology*, Academic Press, San Diego (1996) or will be able to determine appropriate polymerases and conditions by systematic testing using known assays, such as gel electrophoresis or mass spectrometry, to measure the length of amplified fragments.

*E. coli* Pol I or its Klenow fragment can be used for isothermal amplification of a genome to produce small genomic DNA fragments, for example, in a low salt (I=0.085) reaction incubated at a temperature between about 5° C. and 37° C. Exemplary buffers and pH conditions that can be used to amplify gDNA with Klenow fragment include, for example, 50 mM Tris HCl (pH 7.5), 5 mM $MgCl_2$, 50 mM NaCl, 50 ug/ml bovine serum albumin (BSA), 0.2 mM of each dNTP, 2 ug (microgram) random primer (n=6), 10 ng gDNA template and 5 units of Klenow exo- incubated at 37° C. for 16 hours. Similar reaction conditions can be run where one or more reaction component is omitted or substituted. For example, the buffer can be replaced with 50 mM phosphate (pH 7.4) or other pH values in the range of about 7.0 to 7.8 can be used. A gDNA template to be amplified can be provided in any of a variety of amounts including, without limitation, those set forth previously herein. In an alternative embodiment, conditions for amplification can include, for example, 10 ng genomic DNA template, 2 mM dNTPs, 10 mM $MgCl_2$, 0.5 U/ul (microliter) polymerase, 50 uM (micromolar) random primer (n=6) and isothermal incubation at 37° C. for 16 hours.

In particular embodiments, an amplification reaction can be carried out in two steps including, for example, an initial annealing step followed by an extension step. For example, 10 ng gDNA can be annealed with 100 uM random primer (n=6) in 30 ul of 10 mM Tris-Cl (pH 7.5) by brief incubation at 95° C. The reaction can be cooled to room temperature and an annealing step carried out by adding an equal volume of 20 mM Tris-Cl (pH 7.5), 20 mM $MgCl_2$, 15 mM dithiothreitol, 4 mM dNTPs and 1 U/ul Klenow exo- and incubating at 37° C. for 16 hrs. Although exemplified for Klenow-based amplification, those skilled in the art will recognize that separate annealing and extension steps can be used for amplification reactions carried out with other polymerases such as those set forth below.

In particular embodiments, primers having random annealing regions of different lengths (n) can be substituted in the Klenow-based amplification methods. For example, the n=6 random primers in the above exemplary conditions can be replaced with primers having other random sequence lengths including, without limitation, n=7, 8, 9, 10, 11 or 12 nucleotides. Again, although exemplified for Klenow-based amplification, those skilled in the art will recognize that random primers having different random sequence lengths (n) can be used for amplification reactions carried out with other polymerases such as those set forth below.

T4 DNA polymerase can be used for amplification of single stranded or denatured gDNA, for example, in 50 mM HEPES pH 7.5, 50 mM Tris-HCl pH 8.6, or 50 mM glycinate pH 9.7. A typical reaction mixture can also contain 50 mM KCl, 5 mM $MgCl_2$, 5 mM dithiothreitol (DTT), 40 ug/ml gDNA, 0.2 mM of each dNTP, 50 ug/ml BSA, 100 uM random primer (n=6) and 10 units of T4 polymerase incubated at 37° C. for at least one hour. Temperature cycling can be used to displace replicate strands for multiple rounds of amplification.

T7 polymerase is typically highly processive allowing polymerization of thousands of nucleotides before dissociating from a template DNA. Typical reaction conditions under which T7 polymerase is highly processive are 40 mM Tris-HCl pH 7.5, 15 mM $MgCl_2$, 25 mM NaCl, 5 mM DTT, 0.25 mM of each dNTP, 50 ug/ml single stranded gDNA, 100 uM random primer (n=6) and 0.5 to 1 unit of T7 polymerase. However, at temperatures below 37° C. processivity of T7 polymerase is greatly reduced. Processivity of T7 polymerase can also be reduced at high ionic strengths, for example above 100 mM NaCl. Form II T7 polymerase is not typically capable of amplifying double stranded DNA. However, Form I T7 polymerase and modified T7 polymerase (SEQUENASE™ version 2.0 which lacks the 28 amino acid region Lys 118 to Arg 145) can catalyze strand displacement replication. Accordingly, small genome fragments can be amplified in a method of the invention using a modified T7 polymerase or modified conditions such as those set forth above. In particular embodiments, SEQUENASE™ can be used in the presence of *E. coli* single stranded binding protein (SSB) for increased strand displacement. SSB can also be used to increase processivity of SEQUENASE™, if desired.

Taq polymerase is highly processive at temperatures around 70° C. when reacted with a 10 fold molar excess of template and random primer (n=6). An amplification reaction run under these conditions can further include a buffer such as Tris-HCl at about 20 mM, pH of about 7, about 1 to 2 mM $MgCl_2$, and 0.2 mM of each dNTP. Additionally a stabilizing agent can be added such as glycerol, gelatin, BSA or a non-ionic detergent. Taq polymerase has low processivity at temperatures below 70° C. Accordingly, small fragments of gDNA can be obtained by using Taq polymerase at a low temperature in a method of the invention, or in another condition in which Taq has low processivity. In another embodiment, the Stoffel Fragment, which lacks the N-terminal 289 amino acid residues of Taq polymerase and has low processivity at 70° C., can be used to generate relatively small gDNA fragments in a method of the invention. Taq can be used to amplify single stranded or denatured DNA templates in a method of the invention. Temperature cycling can be used to displace replicate strands for multiple rounds of amplification.

Those skilled in the art will recognize that the conditions for amplification with the various polymerases as set forth above are exemplary. Thus, minor changes that do not substantially alter activity can be made. Furthermore, the conditions can be substantively changed to achieve a desired amplification activity or to suit a particular application of the invention.

The invention can also be carried out with variants of the above-described polymerases, so long as they retain polymerase activity. Exemplary variants include, without limitation, those that have decreased exonuclease activity, increased fidelity, increased stability or increased affinity for nucleoside analogs. Exemplary variants as well as other polymerases that are useful in a method of the invention include, without limitation, bacteriophage phi29 DNA polymerase (U.S. Pat. Nos. 5,198,543 and 5,001,050), exo(−)Bca DNA polymerase (Walker and Linn, *Clinical Chemistry* 42:1604-1608 (1996)), phage M2 DNA polymerase (Matsumoto et al., *Gene* 84:247 (I 989)), phage phiPRD 1 DNA polymerase (Jung et al., *Proc. Natl. Acad. Sci. USA* 84:8287 (1987)), exo(−)VENT™ DNA polymerase (Kong et al., *J. Biol. Chem.* 268.1965-1975 (1993)), T5 DNA polymerase (Chatterjee et al., *Gene* 97:13-19 (1991)), and PRD1 DNA polymerase (Zhu et al., *Biochim. Biophys. Acta.* 1219:267-276 (1994)).

A further polymerase variant that is useful in a method of the invention is a modified polymerase that, when compared to its wild type unmodified version, has a reduced or eliminated ability to add non-template directed nucleotides to the 3' end of a nucleic acid. Exemplary variants include those that affect activity of the polymerase toward adding all types of nucleotides or one or more types of nucleotides such as pyrimidine nucleotides, purine nucleotides, A, C, T, U or G. Modifications can include chemical modification of amino acid groups in the polymerase or sequence mutations such as deletions, additions or replacements of amino acids. Examples of modified polymerases having reduced or eliminated ability to add non-template directed nucleotides to the 3' end of a nucleic acid are described, for example, in U.S. Pat. No. 6,306,588 or Yang et al., *Nucl. Acids Res.* 30:4314-4320 (2002). In a particular embodiment, such a polymerase variant can be used in an SBE or ASPE detection method described herein.

In particular embodiments of the invention, a double stranded genomic DNA that is to be amplified by a strand displacing polymerase can be reacted with a nicking agent to produce single strand breaks in the covalent structure of the genomic DNA template. The introduction of single strand breaks in a gDNA template can be used, for example, to improve amplification efficiency or reproducibility in isothermal amplification. Nicking can be used, for example, in a random primer amplification reaction or arbitrary-primed amplification reaction. A non-limiting advantage of introducing single-strand breaks in an amplification reaction is that it can be used in place of heat denaturation. Heat denaturation is deleterious to certain random-primed amplification reactions as described, for example, in Lage et al., Genome Res. 13:294-307 (2003). In this regard, locations at which a gDNA template is nicked can provide priming sites for polymerase activity. Thus, contacting a gDNA with a nicking agent can increase the number of priming sites in the gDNA template, thereby improving amplification efficiency. The number of nicks or location of nicks or both can be influenced by use of particular conditions that favor a desired nicking activity level or use of a nicking agent that is sequence specific. Thus, use of a nicking agent can improve the reproducibility of amplification.

Accordingly, the invention further provides a method of amplifying genomic DNA that includes the steps of: (a) providing isolated double stranded genomic DNA; (b) contacting the double stranded genomic DNA with a nicking agent, thereby producing nicked double stranded genomic DNA; and (c) contacting the nicked double stranded genomic DNA with a strand displacing polymerase and a plurality of primers, wherein the genomic DNA is amplified. As set forth above, the plurality of primers can be a population of random primers, for example, in a random primer amplification reaction.

A nicking agent used in a method of the invention can be any physical, chemical, or biochemical entity that cleaves a covalent bond connecting adjacent sequences in a first nucleic acid strand producing a product in which the adjacent sequences are hybridized to the same complementary strand. Exemplary nicking agents include, without limitation, single strand-nicking enzymes such as DNAse I, N.BstNBI, MutH, or geneII protein of bacteriophage f1; chemical reagents such as free radicals; or ultrasound.

A nicking agent can be contacted with a double stranded gDNA by mixing the agent and gDNA together in solution. Those skilled in the art will know or be able to determine appropriate conditions for nicking the gDNA based on that which is known in the art regarding activity of the nicking agent as available, for example, from various commercial suppliers such as Promega Corp. (Madison, Wis.), or Roche Applied Sciences (Indianapolis, Ind.). A chemical or biological nicking agent can be one that is exogenous to the genomic DNA, having come from a source that is different from the DNA. Alternatively, a nicking agent that is normally found with the genomic DNA in its native environment can be contacted with the gDNA in a method of the invention. Such an endogenous nicking agent can be activated to increase its nicking activity or it can be isolated from the genomic DNA and subsequently mixed with the gDNA, for example, at a higher concentration compared to its native environment with the gDNA. A nicking agent, whether endogenous or exogenous to a gDNA, can be isolated prior to being contacted with the gDNA in a method of the invention.

Those skilled in the art will understand that an amplified representative population of genome fragments can be provided from a freshly isolated sample or one that has been stored under appropriate conditions for preserving the integrity of the sample. Thus, a sample provided in a method of the invention can include agents that stabilize the fragments, so long as the agents do not interfere with hybridization and detection steps and other steps used in the various embodiments set forth herein. In cases where a stabilizing agent that interferes with the methods is included in a sample, the fragments can be separated from the agent using known purification and separation methods. Those skilled in the art will know or be able to readily determine appropriate conditions for storing a representative population of genome fragments based on conditions known in the art for storing nucleic acids as described, for example, in Sambrook et al., supra, (2001) and in Ausubel et al., supra, (1998).

In particular embodiments, a gDNA can be amplified by a method that utilizes random or degenerate oligonucleotide primed polymerase chain reaction (PCR) with heat denatured gDNA templates. An exemplary method is known as primer extension preamplification (PEP). This technique uses random 15-mers in combination with Taq DNA polymerase to initiate copies throughout the genome. This technique can be used to amplify genomic DNA from as little as a single cell using, for example, conditions described in Zhang et al., *Proc. Natl. Acad. Sci. USA,* 89:5847-51 (1992); Snabes et al., *Proc. Natl. Acad. Sci. USA,* 91:6181-85 (1994); or Barrett et al., *Nucleic Acids Res.,* 23:3488-92 (1995).

Another gDNA amplification method that is useful in the invention is Tagged PCR which uses a population of two-domain primers having a constant 5' region followed by a random 3' region as described, for example, in Grothues et al. *Nucleic Acids Res.* 21(5):1321-2 (1993). The first rounds of amplification are carried out to allow a multitude of initiations on heat denatured DNA based on individual hybridization from the randomly-synthesized 3' region. Due to the nature of the 3' region, the sites of initiation will be random throughout the genome. Thereafter, the unbound primers can be removed and further replication can take place using primers complementary to the constant 5' region.

A further approach that can be used to amplify gDNA in a method of the invention is degenerate oligonucleotide primed polymerase chain reaction (DOP-PCR) under conditions described, for example, by Cheung et al., *Proc. Natl. Acad. Sci. USA,* 93:14676-79 (1996) or U.S. Pat. No. 5,043,272. Low amounts of gDNA, for example, 15 pg of human gDNA, can be amplified to levels that are conveniently detected in the methods of the invention. Reaction conditions used in the methods of Cheung et al. can be selected for production of an amplified representative population of genome fragments having near complete coverage of the human genome. Furthermore modified versions of DOP-PCR, such as those described by Kittler et al. in a protocol known as LL-DOP-PCR (Long products from Low DNA quantities-DOP-PCR) can be used to amplify gDNA in accordance with the invention (Kittler et al., *Anal. Biochem.* 300:237-44 (2002)).

Primer-extension preamplification polymerase chain reaction (PEP-PCR) can also be used in a method of the invention in order to amplify gDNA. Useful conditions for amplification of gDNA using PEP-PCR include, for example, those described in Casas et al., *Biotechniques* 20:219-25 (1996).

Amplification of gDNA in a method of the invention can also be carried out on a gDNA template that has not been denatured. Accordingly, the invention can include a step of producing an amplified representative population of genome fragments from a gDNA template under isothermal conditions. Exemplary isothermal amplification methods that can be used in a method of the invention include, but are not limited to, Multiple Displacement Amplification (MDA) under conditions such as those described in Dean et al., *Proc Natl. Acad. Sci USA* 99:5261-66 (2002) or isothermal strand displacement nucleic acid amplification as described in U.S. Pat. No. 6,214,587. Other non-PCR-based methods that can be used in the invention include, for example, strand displacement amplification (SDA) which is described in Walker et al., *Molecular Methods for Virus Detection, Academic Press, Inc.,* 1995; U.S. Pat. Nos. 5,455,166, and 5,130,238, and Walker et al., *Nucl. Acids Res.* 20:1691-96 (1992) or hyperbranched strand displacement amplification which is described in Lage et al., *Genome Research* 13:294-307 (2003). Isothermal amplification methods can be used with the strand-displacing φ29 polymerase or Bst DNA polymerase large fragment, 5'->3' exo⁻ for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase.

In particular embodiments of the invention, a genomic DNA or population of amplified gDNA fragments can be in vitro transcribed into genomic RNA (gRNA) fragments. Creation of gRNA in a method of the invention offers several non-limiting advantages for detection of typable loci in primer extension assays such as DNA array-based primer extension assays. Array-based primer extension typically includes a step of hybridizing a target DNA to an immobilized probe DNA and subsequent modification or extension of the probe-target hybrid with a DNA polymerase. These assays can often be compromised by artifacts arising from unwanted formation of probe-probe hybrids, due to their physical proximity on the array surface, and subsequent ectopic extension of these probe-probe hybrids. In embodiments of the invention where gDNA is converted into gRNA, such artifacts can be avoided because DNA polymerase is replaced with reverse transcriptase (RT) which does not efficiently modify or extend probe-probe hybrids because they are DNA-DNA hybrids and reverse transcriptase is selective for hybrids having an RNA template. Furthermore, the use of gRNA and reverse transcriptase for detection of target probe hybrids minimizes ectopic extension in a direct hybridization/array-based primer extension assay. In an array-based primer extension reaction both inter-probe and intra-probe self-extension (ectopic extension) can lead to high-backgrounds. Use of RT and gRNA prevent artifacts due to ectopic extension because, although RT can easily extend a DNA probe hybridized to an RNA target, it will not efficiently extend DNA-DNA complexes.

Accordingly, the invention provides a method for detecting typable loci of a genome. The method includes the steps of (a) in vitro transcribing a population of amplified gDNA fragments, thereby obtaining genomic RNA (gRNA) fragments; (b) hybridizing the gRNA fragments with a plurality of nucleic acid probes having sequences corresponding to the typable loci; and (c) detecting typable loci of the gRNA fragments that hybridize to the probes.

Figure 8:
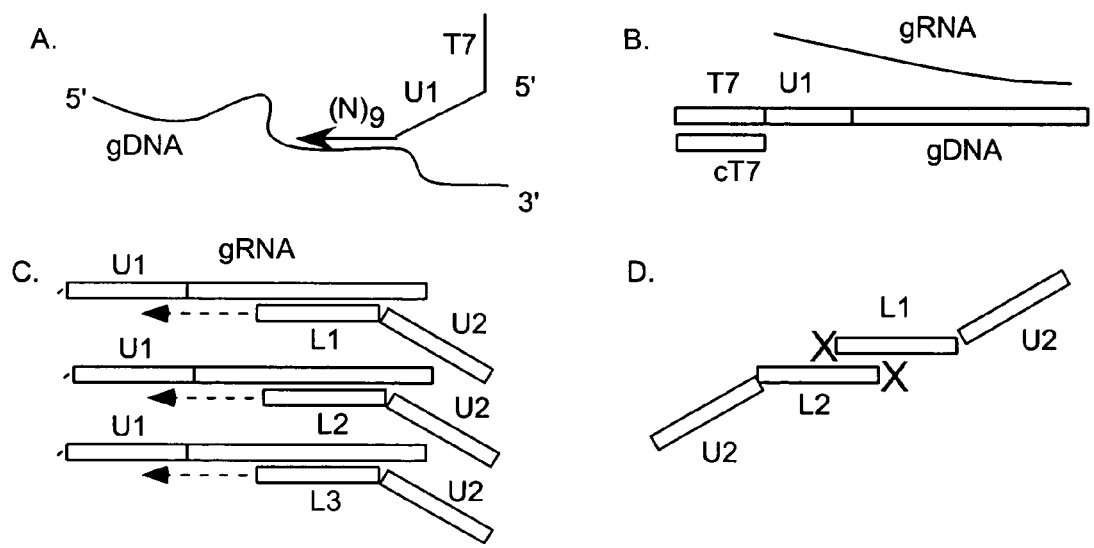
FIG. 8 shows a diagram of an exemplary method for generating genomic RNA as a target nucleic acid for amplification or detection.

A diagrammatic example of a method for amplifying gDNA to produce gRNA fragments is shown in FIG. 8. As shown in Panel 8A, gDNA can be amplified with DNA polymerase and a population of random DNA primers to produce a representative population of genome fragments prior to an in vitro transcription step. In the example shown, gDNA is Random-primed labeled (RPL) using a population of primers including a random region of 9 nucleotides and a fixed region having a universal priming sequence (U1) and a T7 promoter sequence (T7). In the example shown in FIG. 8, the random sequence is 9 nucleotides long. However, it will be understood that any of a variety of random sequence lengths can be used to suit a particular application of the invention including, for example, a random sequence that is 3, 4, 5, 6, 7, 8, 10, 11, 12, 13, 14, 15 or more nucleotides long. Furthermore, a random sequence of a primer used in a method of the invention can include interspersed positions having a fixed nucleotide or regions having a fixed sequence of two or more nucleotides, if desired.

As shown in Panel B, the representative population of T7 promoter labeled genome fragments can be in vitro transcribed to gRNA form using a T7 RNA polymerase and a complementary T7 primer (cT7). Transcription of gDNA to gRNA fragments can also be carried out with other promoters such as T3 or SP6 and their respective polymerases as set forth in further detail below.

A gRNA-based representative population of genome fragments produced by in vitro transcription can be manipulated and detected in any of a variety of ways as set forth herein. For example, the gRNA-based genome fragments produced by the methods exemplified in FIG. 8B will have U1 labeled tails. These tails can be used, for example, to isolate the gRNA fragments from gDNA and other amplification reaction components using a complementary capture sequence attached to a solid phase. Genomic RNA fragments can be detected or copied into DNA using a reverse transcriptase. The gRNA-based representative population of genome fragments can be detected directly using methods such as those set forth below or, alternatively, can be copied into DNA prior to detection. As shown in the exemplary amplification step of FIG. 8C, the population of gRNA fragments can be replicated using locus-specific primers, optionally having a second universal sequence (U2), and a reverse transcriptase. This step can be followed by amplification using universal PCR with U1 and U2 primers Thus, the gRNA fragments can be replicated to produce a locus-specific, amplified representative population of genome fragments. As set forth below in further detail, reverse transcriptase-directed replication of the gRNA with locus specific primers can provide complexity reduction and, if desired, can add a U2 universal priming site. In embodiments where the U2 sequence is present, the population of genome fragments produced by replication with locus specific primers will each have flanking U1 and U2 sequences that are useful for detecting or amplifying the population. Thus, the fully extended products can be amplified in a universal PCR reaction primed at the U1 and U2 primer sites.

Moreover, as shown in FIG. 8D, a "primer-dimer" cannot be extended in the detection step because reverse transcriptase cannot extend a DNA template very efficiently. In contrast, a DNA polymerase can extend the L1-L2 primer dimer potentially leading to detection artifacts. Thus, the use of gRNA-based representative populations of genome fragments can provide the non-limiting advantage of avoiding artifacts in some multiplex detection methods. Thus, the use of gRNA can provide the advantage of increased efficiency for multiplexed detection of large numbers of typable loci.

A nucleic acid primer used in a method of the invention to transcribe gDNA into a gRNA-based representative population of genome fragments or to reverse transcribe gRNA can have length, composition or other properties as set forth herein in regard to primers used with other polymerases and templates. Those skilled in the art will know or be able to determine appropriate properties of a nucleic acid primer for use in an in vitro transcription or reverse transcriptase step of the invention based on the guidance and teaching set forth herein and that which is known regarding reverse transcriptases or RNA polymerases as set forth below and described, for example, in Eun et al., supra (1996).

Furthermore, although the primer populations exemplified above in regard to the embodiment of FIG. 8 have a single U1 sequence and a single U2 sequence, it will be understood that a population of primers useful in the invention can include more than one constant sequence region. Thus, a plurality of random primer sub-populations, each having different constant sequence regions, can be present in a larger population used for hybridization or amplification in a method of the invention.

Any RNA polymerase that is capable of synthesizing a complementary RNA from a DNA template can be used in a method of the invention. An exemplary RNA polymerase useful in the invention is T7 RNA polymerase. Conditions that can be used in a method of the invention for in vitro transcription with T7 RNA polymerase include, without limitation, 40 mM Tris-HCl pH 8.0 (37° C.), 6 mM MgCl$_2$, 5 mM DTT, 1 mM spermidine, 50 ug/ml BSA, 40 ug/ml gDNA fragments including a phage promoter, 0.5 to 8.5 mM NTPs, and 200 to 300 units T7 RNA polymerase in 50 microliters. Another RNA polymerase that can be used in a method of the invention is SP6 RNA polymerase. Exemplary conditions for use include, without limitation, 40 mM Tris-HCl pH 8.0 (25° C.), 6 mM MgCl$_2$, 10 mM DTT, 2 mM spermidine, 50 ug/ml BSA, 50 ug/ml gDNA fragments containing an SP6 promoter, 0.5 mM of each NTP, and 10 units SP6 RNA polymerase in 50 microliters.

T3 RNA polymerase can also be used in a method of the invention for in vitro transcription, for example, under conditions including 50 mM Tris-HCl pH 7.8 (37° C.), 25 mM NaCl, 8 mM MgCl$_2$, 5 mM DTT, 2 mM spermidine, 50 ug/ml BSA, 50 ug/ml gDNA fragments containing a T3 promoter, 0.5 mM of each NTP, and T3 RNA polymerase in 50 microliters.

Any reverse transcriptase (RT) that catalyzes the synthesis of complementary DNA from an RNA template can be used in a method of the invention. Exemplary RTs that can be used in a method of the invention include, but are not limited to, those from retroviruses such as avian myoblastosis virus (AMV) RT, Moloney murine leukemia virus (MoLV) RT, HIV-1 RT, or Rouse sarcoma virus (RSV) RT. Generally, a reverse transcription reaction used in a method of the invention will include an RNA template, one or more dNTPs and a nucleic acid primer with a 3' OH group. RNAse inhibitors can be added, if desired, to inhibit degradation of the transcribed product. Particular reaction conditions can be used to suit a particular RT or a particular application of the invention.

Useful conditions for modification or elongation with AMV RT include, for example, 50 mM Tris-HCl (pH 8.3 at 42° C.), 150 mM NaCl (or 100 mM KCl), 6 to 10 mM MgCl$_2$, 1 mM DTT, 50 ug/ml BSA, 50 units RNasin, 0.5 mM Spermidine HCL, 4 mM NA-PP$_i$, 0.2 mM of each dNTP, 1-5 ug gRNA, 0.5 to 2.5 ug primer and 10 units AMV RT in 50 microliters. However it is also possible to perform the reaction at pH 8.1 at 25° C. with otherwise similar conditions. Other conditions that can be used for AMV RT activity and in particular to inhibit DNA-dependent DNA synthesis are described, for example, in Lokhava et al., *FEBS Lett.* 274: 156-158 (1990) or Lokhava et al., *Mol. Biol. (USSR)* 24:396-407 (1990).

In embodiments where MoLV RT is used, exemplary conditions for modification or elongation include, without limitation, 50 mM Tris-HCl (pH 8.1 at 25° C.), 75 mM KCl, 3 mM MgCl$_2$, 10 mM DTT, 100 ug/ml BSA, 20 units RNasin, 50 ug/ml actinomycin D, 0.5 mM of each dNTP, 5-10 ug gRNA, 0.5 to 4 ug primer and 200 units MoLV RT in 50 microliters.

An RT used in a method of the invention can also be from a non-retroviral source including, for example, DNA viruses such as hepatitis B virus or *caulimovirus*, bacteria such as *Myxococcus xanthus* or some strains of *E. coli*, yeast such as those bearing the Ty retrotransposon, fungi, invertebrates such as those bearing the copia-like element of *Drosophila*, or plants. Furthermore, if desired reverse transcription can be carried out in a method of the invention using a DNA polymerase that has RT activity such as *E. coli* DNA Pol I. However, for the reasons set forth above, it may be desired to carry out reverse transcription under conditions in which activity toward DNA templates is inhibited or substantially absent, for example, using an RT that is not capable of DNA-dependent DNA synthesis or using conditions such as a pH, ionic strength or Mg$^{2+}$ concentration that inhibit DNA-dependent DNA synthesis. Furthermore, an inhibitor of DNA-dependent DNA synthesis such as actinomycin D or pyrophosphate (Na-PP$_i$) can be added if desired.

An exemplary DNA polymerase that is capable of RT activity is Tth pol when used in the presence of Mn$^{2+}$. Exemplary conditions for reverse transcription of gRNA with Tth pol RT include, without limitation, 50 mM Tris-Cl (pH 8.8), 16 mM NH$_4$SO$_4$, 1 mM MnCl$_2$, 200 µM dNTPs, 0.25 U/µl Tth pol, 100 fmol/µl RNA template at 70° C. for 20 min.

Amplification of gDNA in a method of the invention can be carried out such that an amplified representative population of genome fragments having a desired complexity is produced. For example, an amplified representative population of genome fragments having a desired complexity can be produced by specifying the frequency or diversity of priming or fragmentation events that occur during an amplification reaction. Accordingly, the invention can be used to produce an amplified representative population of genome fragments having high or low complexity depending upon the desired use of the population of fragments. Several of the amplification conditions set forth above and in the Examples below provide high complexity representations. A method of the invention can include a complexity reduction step or can be carried out with an amplification method that produces a low complexity representation, if desired.

An exemplary method for producing a low complexity representation is linker adaptor-PCR which calls for an initial random digestion of DNA with a restriction endonuclease, ligation of the digested fragments to an adaptor oligonucleotide and PCR amplification of heat denatured adaptor derivatized fragments as described, for example, in Lucito et al., *Genome Res.* 10:1726-36 (2000). Altering the conditions of gDNA digestion in the method can be used to influence the complexity of the amplified representative population of genome fragments that is produced. In particular, a low complexity representation can be obtained using an infrequent-cutting endonuclease having, for example, a 6 base or longer recognition motif. Accordingly, a frequent cutter can be used to obtain a high complexity representation. For example, Dpn II, which recognizes the four nucleotide site GATC, and thus restricts gDNA relatively frequently, can produce a representative population of human genome fragments that that contains about 70% of the genome. In contrast, a relatively infrequent cutter can be used to produce a low complexity representation. For example, Bgl II, which recognizes the six nucleotide site AGATCT and thus restricts gDNA relatively infrequently, can be used to produce a representative population of human genome fragments that contains only approximately 2.5% of a genome. Furthermore, a gDNA can be fragmented to an average length that is smaller than the processivity of the polymerase used for amplification, thereby reducing the complexity of the amplified representative population of genome fragments that is produced.

A further method for producing a low complexity representation is the use of two or more adaptors for anchored linker adaptor PCR. In particular embodiments complexity reduction can be achieved by fragmenting a gDNA sample using at least two restriction enzymes; ligating adaptors to the resulting fragments; and selectively amplifying the fragments that were cut on one end by one restriction enzyme and on the other end by a different restriction enzyme. If one enzyme is a 6-cutter and the other is a 4-cutter, the representation will be anchored about the 6-cutter sites with an average size determined by frequency of the 4-cutter digestion (about every 256 bases). This is a useful size for PCR-based amplification. The complexity of the resulting sample can be regulated by choosing enzymes that cut with a particular frequency. Selective amplification can also be accomplished by designing one adaptor to have a 5', overhang and the second adaptor to have a 3' overhang where the overhangs have the annealing sites for amplification primers used to replicate the fragments. Exemplary conditions for the use of multiple adaptors for complexity reduction are described in US 2003/0096235 A1.

Complexity reduction can also be carried out in a locus-specific manner. Accordingly, the invention further provides a method of producing a reduced complexity, locus-specific, amplified representative population of genome fragments. The method includes the steps of (a) replicating a native genome with a plurality of random primers, thereby producing an amplified representative population of genome fragments; (b) replicating a sub-population of the amplified representative population of genome fragments with a plurality of different locus-specific primers, thereby producing a locus-specific, amplified representative population of genome fragments; and (c) isolating the sub-population, thereby producing a reduced complexity, locus-specific, amplified representative population of genome fragments.

Figure 9:
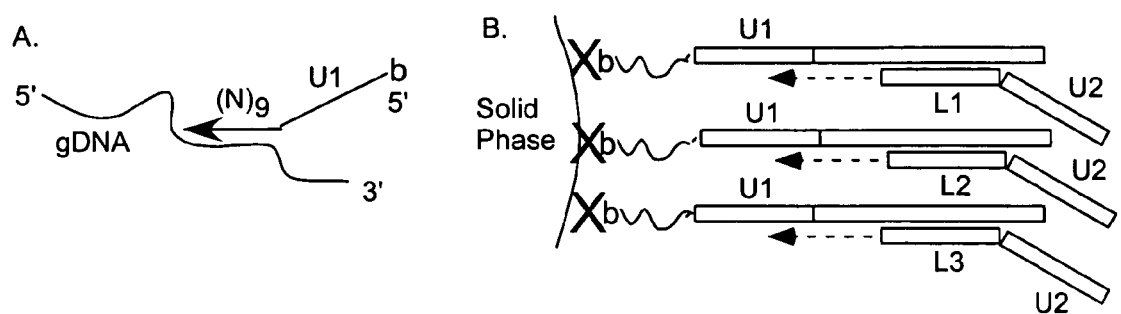
FIG. 9 shows a diagram of an exemplary method for generating a reduced complexity, locus-specific representative population of genome fragments.

An exemplary method that can be used for complexity reduction is amplification to produce gRNA fragments as shown in FIG. 8 and described above. A diagrammatic example of a method for producing a reduced complexity, locus-specific, amplified representative population of genome fragments is shown in FIG. 9. As shown in FIG. 9A a gDNA sample can be amplified by a Random-primed labeling (RPL) technique employing a population of nucleic acid primers each having a random 3' sequence for annealing to the gDNA and a 5' universal priming tail (U1 sequence). Thus, a random-primed labeling reaction can produce an amplified representative population of genome fragments flanked by a universal priming site. In the example shown in FIG. 9, the random sequence has 9 nucleotides. However, it will be understood that any of a variety of random sequence lengths or compositions can be used to suit a particular application of the invention including, for example, those set forth previously herein. In general, as the length of the random annealing portion of a population of random primers is reduced the number of potential annealing sites on a genome will be increased, thereby increasing the complexity of the amplified representation.

As shown in FIG. 9B, an amplified representative population of genome fragments can be isolated from genomic DNA, for example, by immobilization on solid phase beads. In the example of FIG. 9A immobilization of the amplified fragments can be facilitated by a biotin bound to the $N_9$-U1 primer. The biotinylated amplification product can be captured by a solid phase that is derivatized with avidin or streptavidin and, if desired, subsequently isolated from the gDNA template. Other exemplary capture moieties and their immobilized receptors that can be used in a primer for random primer amplification are set forth above. Thus, a method of amplifying gDNA can further include a step of capturing or isolating an amplified representative population of genome fragments. Exemplary substrates that can be used to capture or isolate an amplified representative population of genome fragments include, for example, those set forth below in regard to separation of single stranded nucleic acids from nucleic acid hybrids.

Those skilled in the art will recognize that amplified genome fragments can be separated from other reaction components in a method of the invention using a solid phase substrate as exemplified above. Similarly amplified genome fragments can be separated based on other properties of the fragments such as their size. Thus, filtration or chromatography methods such as size exclusion chromatography can be used to separate genome fragments from other reaction components such as probes that are not annealed.

A method of the invention can include a step of replicating a sub-population of the amplified representative population of genome fragments with a plurality of different locus-specific primers each having a 3' locus specific sequence region and a 5' constant sequence region. Continuing with the example of FIG. 9B, the immobilized random primer amplified product can be hybridized with a population of different primers having different locus-specific 3' sequences identified as L1, L2 or L3, and a 5' second universal tail (U2). At this point a washing step can be included, if desired, to remove mis-annealed and excess primers. Conditions for washing can include any that remove non-specifically bound nucleic acids while maintaining specific hybrids. Primer extension can then be used to replicate a subpopulation of the amplified representative population of genome fragments having sequences complementary to the locus-specific primers. This subpopulation will have lower complexity compared to the original gDNA and the amplified population of genome fragments that was produced with the Ng-U1 primer. Furthermore, the complexity reduction will be locus specific due to selection with the locus-specific primers in the second amplification step. The number of different locus-specific primers and length of the locus-specific sequences can be altered to increase or decrease the complexity of a representation obtained in a method of the invention.

Extension of the U2 containing primers along the full length of the captured fragments in the example shown in FIG. 9B will produce a locus-specific, amplified representative population of genome fragments labeled with the first constant region (U1) and the second constant region (U2). Thus, the fully extended products can be amplified in a universal PCR reaction primed at the U1 and U2 primer sites. Accordingly a method of the invention can include a step of replicating a reduced complexity, locus specific, amplified representative population of genome fragments with complementary primers to flanking first and second constant regions. Furthermore, detection of the fragments can be made based on the presence pf both U1 and U2 sequences, for example, using techniques described below in regard to detection of modified OLA probes.

Complexity reduction can also be carried out by removing particular sequences from a population of genome fragments. In one embodiment, high copy number or abundant sequences in a sample of genome fragments can be inhibited from hybridizing to detection or capture probes. For example, Cot analysis can be used in which abundant species are kinetically driven to reanneal while leaving the single copy species in a single stranded state capable of hybridization to probes. Thus in particular embodiments, a sample of genome fragments can be pre-treated with cot oligonucleotides that are complementary to particular repeated sequences, or to other sequences that are desired to be titrated out of the sample, prior to exposure of the sample to an array of probes. In another example, a sample of genome fragments can be cooled to a temperature and for short time period that are sufficient for a substantial fraction of over-represented sequences to re-anneal but insufficient for substantial re-annealing of sequences present in low copy numbers. The resulting sample will have a reduced amount of repeated sequences available for subsequent interaction with an array of probes.

Undesired fragments that form double stranded species, for example, in Cot analysis or genome fragment reannealing, can be separated from single stranded species based on different properties of single and double stranded nucleic acids. In a particular embodiment, enzymes that preferentially cleave double stranded DNA can be used. For example, DNAse I can cleave double-stranded DNA 100 to 500 fold faster than single stranded DNA under known conditions. Accordingly, undesired fragments can be removed by treatment with Cot oligonucleotides or by fragment reannealing, and treatment with DNAse I under conditions in which undesired fragments preferentially form double stranded species and get cleaved. Furthermore, other enzymes that preferentially modify, cleave or bind to double stranded species compared to single stranded species can be used to separate the species in a method of the invention such as sequence specific restriction endonucleases or Kamchatka crab duplex-specific endonuclease.

Arbitrary-primer PCR can also be used to amplify a genomic DNA in a method of the invention. Arbitrary-primer PCR can be carried out by replicating a gDNA sample with a primer under non-stringent conditions such that the primer arbitrarily anneals to various locations in the gDNA. Subsequent PCR steps can be carried out at higher stringency to amplify the fragments generated due to arbitrary priming in the previous step. The length, sequence or both of an arbitrary primer can be selected in accordance with the probability of priming at particular intervals along the gDNA. In this regard, as primer length increases, the average interval between arbitrarily primed locations will increase, assuming no change in other amplification conditions. Similarly, a primer having a sequence complementary to or similar to a repeated sequence will prime more often, yielding shorter intervals between amplified fragments than a primer that lacks sequences that are similar to repeated sequences in a genome to be amplified. Arbitrary-primer amplification can be carried out under conditions similar to those described, for example, in Bassam et al., *Australas Biotechnol.* 4:232-6 (1994). In accordance with the invention, amplification can be carried out under isothermal conditions using an arbitrary primer, low stringency annealing conditions, and a strand-displacing polymerase.

Another method that can be used to amplify a genome in the invention is inter-Alu PCR. In this method, primers are designed to anneal to Alu sequences which are repeated throughout the genome. PCR amplification with these primers will yield fragments flanked by Alu repeats. Those skilled in the art will recognize that similar methods can be carried out with primers that anneal to other repeated sequences in a genome of interest such as transcription regulatory regions, splice sites or the like. Furthermore, primers to repeated sequences can be used in isothermal amplification methods such as those set forth herein.

The complexity and degree of representation resulting from amplification with a particular set of primers can be adjusted using different primer hybridization conditions. A variety of hybridization conditions can be used in the present invention, such as high, moderate or low stringency conditions including, but not limited to those described in Sambrook et al., supra, (2001) or in Ausubel et al., supra, (1998). Stringent conditions favor specific sequence-dependent hybridization. In general, longer sequences and increased temperatures favor specific sequence-dependent hybridization. A useful guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993).

Amplification and detection steps used in the invention are generally carried out under stringency conditions which selectively allow formation of a hybridization complex in the presence of complementary sequences. Stringency can be controlled by altering a step parameter that is a thermodynamic variable, including, but not limited to, temperature, formamide concentration, salt concentration, chaotropic salt concentration, pH, organic solvent concentration, or the like. These parameters can also be used to control non-specific binding, as is generally outlined in U.S. Pat. No. 5,681,697. Thus, if desired, certain steps can be performed under relatively high stringency conditions to reduce non-specific binding.

Generally, high stringency conditions include temperatures that are about 5-10° C. lower than the thermal melting point ($T_m$) for the annealing sequences at a particular ionic strength and pH. High stringency conditions include those that permit a first nucleic acid to bind a complementary nucleic acid that has at least about 90% complementary base pairs along its length and can include, for example, sequences that are at least about 95%, 98%, 99% or 100% complementary. Stringent conditions can further include, for example, those in which the salt concentration is less than about 1.0 M sodium ion (or other salts), typically about 0.01 to 1.0 M concentration at pH 7.0 to 8.3 and the temperature is at least about 30° C. for short annealing sequences (e.g. 10 to 50 nucleotides) and at least about 60° C. for long annealing sequences (e.g. greater than 50 nucleotides). High stringency conditions can also be achieved with the addition of helix destabilizing agents such as formamide. High stringency conditions can include, for example, conditions equivalent to hybridization in 50% formamide, 5× Denhart's solution, 5× SSPE, 0.2% SDS at 42° C., followed by washing in 0.1× SSPE, and 0.1% SDS at 65° C. Nucleic acid hybrids can be further stabilized by covalent modification with one or more cross-linking agents.

Moderately stringent conditions include those that permit a first nucleic acid to bind a complementary nucleic acid that has at least about 60% complementary base pairs along its length to the first nucleic acid. Depending upon the particular conditions of moderate stringency used, a hybrid can form between sequences that have complementarity for at least about 75%, 85% or 90% of the base pairs along the length of the hybridized region. Moderately stringent conditions include, for example, conditions equivalent to hybridization in 50% formamide, 5× Denhart's solution, 5×SSPE, 0.2% SDS at 42° C., followed by washing in 0.2×SSPE, 0.2% SDS, at 65° C. 7

Low stringency hybridization includes, for example, conditions equivalent to hybridization in 10% formamide, 5× Denhart's solution, 0.6× SSPE, 0.2% SDS at 42° C., followed by washing in 1× SSPE, 0.2% SDS, at 50° C. Denhart's solution and SSPE are well known to those of skill in the art as are other suitable hybridization buffers (see, for example, Sambrook et al., supra (2001) or in Ausubel et al., supra (1998)).

In embodiments of the invention where a hybrid will be modified, for example, by a polymerase, conditions can be further chosen to suit the particular modification reaction. For example, when the modification involves replication or amplification, conditions such as those set forth above in regard to particular polymerases can be used. It will be understood that a modifying agent such as a polymerase can be added at any point during an amplification or detection step including, for example, prior to, during, or after the addition of nucleic acid components of the modification reaction.

The methods of the invention can be used to amplify a native genome in a single reaction step or in a single reaction vessel to produce an amplified representative population of genome fragments having high complexity. The ability to use a single step or reaction vessel provides a non-limiting advantage of increasing amplification efficiency compared to methods requiring multiple steps or reaction vessels. Furthermore, in particular embodiments a high complexity amplified representative population of genome fragments can be obtained under conditions that do not require pooling of products from multiple amplification reactions. Thus, the fragments in an amplified representative population of genome fragments can be obtained in parallel rather than sequentially in various embodiments of the invention. However, it is possible to use the methods in embodiments where different reaction steps are carried out in separate vessels, sequentially, or where the products of multiple reactions are pooled, for example, to suit particular applications.

Further description of exemplary methods that can be used in the invention to amplify nucleic acids, such as native genomes or fragments thereof, can be found in U.S. Pat. No. 6,355,431 and include polymerase chain reaction (PCR) amplification, random primed PCR, arbitrary primed PCR, strand displacement amplification, nucleic acid sequence based amplification and transcription mediated amplification.

Following replication of a genome or population of genome fragments, nucleic acids containing a desired modification can be separated from unmodified nucleic acids such as unreacted primers or the template. For example, it can be desirable to remove unextended or unreacted primers because unextended primers can compete with the extended or labeled primers in a variety of the detection methods that are used in the invention, thereby diminishing the signal. Accordingly, a number of different techniques can be used to facilitate the removal of unextended primers. While the discussion below is directed to amplification reactions for clarity, it will be understood that these techniques can also be used to separate modified and unmodified nucleic acids in a detection step.

Separation of nucleic acids can be mediated by selective incorporation of a label including, for example, one or more of the primary or secondary labels described previously herein. Nucleic acids having an incorporated secondary label can be separated from those lacking the label based, for example, on binding to a receptor having specificity for the label. The receptor can be attached, for example, to a solid phase substrate as set forth above in regard to the embodiment exemplified in FIG. 9. Primary labels can be used to separate nucleic acids in a sorting method such as fluorescent activated cell sorting. Similarly, nucleic acids having an incorporated secondary label can be separated from those lacking the label in a sorting method based on detection of a receptor that provides a primary label to the nucleic acid-receptor complex. Separation can also be accomplished using standard size exclusion resins such as G-50 resin, ultrafiltration such as with Amicon or Centricon columns, or ethanol-like precipitation methods.

A nucleic acid can be conveniently labeled in a method of the invention by a moiety introduced during an amplification or modification reaction via a labeled primer, labeled nucleotide precursor or both. In particular embodiments, one or more NTPs used to replicate a nucleic acid can include a secondary detectable label that can be used to separate modified primers from unmodified primers lacking the label. Secondary labels find particular use in detection techniques that include steps for separation of labeled and unlabeled probes, such as SBE, OLA or invasive cleavage. Particularly useful labels include, but are not limited to, one of a binding partner pair; chemically modifiable moieties; or nuclease inhibitors.

By way of example, a secondary label can be a hapten or antigen having affinity for an immunoglobulin, or functional fragment thereof, attached to a solid support. Labeled nucleic acids that are bound to the immunoglobulin can be separated from unlabeled nucleic acids by physical separation of the solid support and soluble fraction. In addition, avidin/biotin systems including, for example, those utilizing streptavidin, biotin mimetics or both, can be used to separate modified nucleic acids from those that are unmodified. Typically the smaller of two binding partners is attached to a nucleic acid. However, attachment of the larger partner can also be useful. For example, the addition of streptavidin to a nucleic acid increases its size and changes its physical properties, which can be exploited for separation. Accordingly, a streptavidin labeled nucleic acid can be separated from unlabeled nucleic acids in a mixture using a technique such as size exclusion chromatography, affinity chromatography, filtration or differential precipitation.

In embodiments, including attachment of a binding partner to a solid support, the solid support can be selected, for example, from those described herein with respect to detection arrays. Particularly useful substrates include, for example, magnetic beads which can be easily introduced to the nucleic acid sample and easily removed with a magnet. Other known affinity chromatography substrates can be used as well. Known methods can be used to attach a binding partner to a solid support.

Typically, a method of detecting typable loci of a genome is carried out on an amplified representative population of genome fragments obtained, for example, by a method set forth above. Alternatively, typable loci can be determined for a representative population of genome fragments derived from a genome by a method other than an amplification method. In one embodiment, a representative population of genome fragments can be obtained by fragmenting a native genome. Exemplary methods that can be used for fragmenting a genome are set forth below. Those skilled in the art will recognize that the fragmentation methods can be used as an alternative to the amplification methods described herein or, if desired in combination with an amplification technique.

An isolated native genome can be fragmented by any physical, chemical or biochemical entity that creates double strand breaks in DNA. In particular embodiments, a native genome can be digested with an endonuclease. Endonucleases useful in the methods of the invention include those that cleave at a specific recognition sequence or those that non-specifically cleave DNA such as DNaseI. Endonucleases are available in the art and can be obtained, for example, from commercial sources such as New England BioLabs (Beverley, Mass.) or Life technologies Inc. (Rockville, Md.) among others. Specific endonucleases can be used to generate polynucleotide fragments of a particular average size according to the frequency with which the enzyme is expected to cut a random sequence. For example, an endonuclease having a six nucleotide recognition sequence would be expected to produce, on average, fragments that are 4096 base pairs long. Average fragment length can be estimated by treating the DNA as a random sequence and estimating the frequency of a recognition site in the random sequence according to the relationship $4^n = s$ where n is the number of bases recognized by the endonuclease and s is the average size of the fragments produced. Incubation conditions can also be modified, as described below, to alter the enzymatic efficiency of the endonuclease, thereby altering the average size of the fragments produced. Using the example of an endonuclease having a 6 base pair recognition site, a decrease in enzymatic efficiency can produce fragments that are on average larger than 4096 base pairs long.

Non-specific endonucleases can also be used to produce genome fragments of a desired average size. Because the endonuclease reaction is bi-molecular, the rate of fragmentation can be manipulated by altering conditions such as the concentrations of the endonuclease, DNA or both. Specifically, a reduction in the concentration of either endonuclease, DNA or both can be used to reduce reaction rate resulting in increased average fragment sizes. Increasing concentrations of either endonuclease, DNA recognition sequence or both will allow for increased efficiency, approaching maximum velocity ($V_{max}$) for the particular enzyme leading to reduced average fragment sizes. Similar changes in conditions can also be applied to site-specific endonucleases because their reactions with DNA are also bi-molecular. Other reaction conditions can also affect the rate of cleavage including, for example, temperature, salt concentration and time of reaction. Methods for altering nuclease reaction rates to produce polynucleotide fragments of determined average size are described, for example, in Sambrook et al., supra, (2001) or in Ausubel et al., supra, (1998).

Other methods that can be used to produce genome fragments include, for example, treatment with chemical agents that disrupt the phosphodiester backbone of DNA such as those that cleave bonds by a free radical mechanism, UV light, mechanical disruption or the like. These and the methods set forth above can be used to produce genome fragments from a native genome, further cleave genome fragments, or cleave other nucleic acids used in the invention. Further exemplary mechanical disruption methods that can be used to produce genome fragments include sonication and shearing.

Random primer whole genome amplification typically produces higher amplification yields and increased representation when intact genomic DNA is used as template compared to fragmented templates. In applications of the invention wherein amplification of fragmented genomic DNA is desired, it is possible to ligate the fragments together to produce concatenated DNA. The concatenated DNA can then be used in a whole genome amplification method such as those set forth previously herein. Exemplary conditions that can be used in a genome fragment concatenation reaction are described, for example, in WO 03/033724 A1.

In embodiments, in which fragmentation of a target nucleic acid sample is not desired, the fragments can be modified for use in a method of the invention. For example, a genomic DNA can be modified to facilitate amplification. An exemplary modification that can facilitate amplification is concatenation of genome fragments to form extended templates that can be efficiently amplified, for example, by random primer amplification. Concatenation can be carried out for example by treating a population of genome fragments with T4 RNA ligase under conditions known in the art such as those described in McCoy et al., *Biochem.* 19:635-642 (1980). Concatenation can also be carried out using a mixture of AP endonuclease, polymerase and ligase. Damaged DNA can be repaired using appropriate enzymes such as the Restorase™ polymerase mixture available from Sigma-Aldrich (R1028). Another modification that can be used is the addition of universal tails to genome fragments. Exemplary methods of incorporating universal tails include, without limitation, treatment of fragments with terminal deoxynucleotides transferase to tail 3' ends with a mononucleotide such as dGTP. Accordingly, a poly G tail can be added as a universal tail to genome fragments. Poly C, T, U, A, or other nucleotide tails can be added as well. Universal tails can also be added by treating genome fragments with T4 RNA ligase and oligonucleotides having a random 4-mer duplex adapter and universal tail sequence under conditions in which the universal tail sequence is added to one or both ends of the genome fragments.

Example X describes methods for amplifying fragments produced by bisulfite treatment of methylated DNA. Those skilled in the art will recognize that the amplification methods described in Example X can be used for nucleic acid fragment samples of any of a variety of compositions and produced by any of a variety of mechanisms. Further examples of DNA fragments useful in the invention include, without limitation, cDNA or degraded genomic DNA, for example, from archived tissues or cells such as those that are stored formalin-fixed, formaldehyde-fixed, paraffin embedded, polymer embedded, ethanol embedded or by some combination thereof. Fragmented DNA can also be obtained from forensic samples, archeological samples, paleontological samples, mummified samples, petrified samples and other samples that have experienced decay due to an extended period of time between the death of the cell or tissue and analysis of its genomic DNA. A method of detecting typable loci of a genome can further include a step of contacting genome fragments with a plurality of nucleic acid probes having sequences corresponding to the typable loci under conditions in which probe-fragment hybrids are formed. A probe used in a method of the invention can have any of a variety of compositions or sizes, so long as it has the ability to bind to a target nucleic acid with sequence specificity. Typically, a probe used in the methods is a nucleic acid including, for example, one having a native structure or an analog thereof. Exemplary nucleic acid probes that can be used in a method of the invention include, without limitation, those set forth above in regard to primers and other nucleic acids useful in the invention. It will be further understood that other sequence specific probes can also be used in a method of the invention including, for example, peptides, proteins or other polymeric compounds.

Probes of the present invention can be complementary to typable loci or other detection positions that are indicative of the presence of the typable loci in a representative population of genome fragments. Thus, a step of detecting a typable locus of a genome fragments can include, for example, detecting the locus itself or detecting another sequence that is genetically linked or associated. This complementarity need not be perfect. For example, there can be any number of base pair mismatches within a hybridized nucleic acid complex, so long as the mismatches do not prevent formation of a sufficiently stable hybridization complex for detection under the conditions being used.

Furthermore, nucleic acid probes used in a method of the invention can include sequence regions that are not complementary to target sequences or other sequences present in a particular population of genome fragments. These non-target complementing sequence regions can include, for example, linker sequences for attaching the probes to a substrate, annealing sites for other nucleic acids such as a primer or other desired sequences. A target-complementing sequence region of a nucleic acid probe can have a length that is, for example, at least 10 nucleotides in length. Longer target-complementing regions can also be useful including, without limitation, those that are at least about 15, 20, 25, 35, 50, 70, 100, 500, 1000, or 5000 nucleotides in length or longer. As set forth above, particular embodiments of the invention provide the ability to amplify a native genome to produce a representative population of relatively small genome fragments. A non-limiting advantage of detecting typable loci of a genome on small genome fragments is that loci that are relatively close can be separated for individual detection. Accordingly, in particular embodiments, such as detection of small target sequences, a target-complementary region of a nucleic acid probe can be at most about 100, 90, 80, 70, 60, 50, 40, 35, 30, 25, 20, or 10 nucleotides in length.

Exemplary target-complementing sequences that are useful in the invention are set forth below in the context of various detection techniques. Those skilled in the art will understand that the probes need not be limited to use in the particular detection technique exemplified but rather can be used in any of a variety of different detection techniques as desired for a particular application of the invention.

A probe used in a method of the invention can further have a modification, for example, to support a particular detection method. For example, in embodiments wherein amplification or modification of a particular probe is not desired, the probe can have a structure that is resistant to modification. As specific examples, a probe can lack a 3' OH group or have a 3' cap moiety, thereby being inert to modification with a polymerase. In particular embodiments, a probe can include a detectable label including, without limitation, one or more of the primary or secondary nucleic acid labels set forth above. Alternatively, detection can be based on an intrinsic characteristic of the probe, fragment or hybrid such that labeling is not required. Examples of intrinsic characteristics that can be detected include, but are not limited to, mass, electrical conductivity, energy absorbance, fluorescence or the like.

Any of a variety of conditions can be used to hybridize probes with genome fragments including, without limitation, those set forth above in regard to primer annealing to target. In particular embodiments, the hybridization conditions can support modification or replication of the probe, genome fragment or both. However, depending upon the detection method in which the probe is applied, hybridization conditions need not support modification of a probe-fragment hybrid. Accordingly, the presence of a particular fragment can be determined based on a detectable property of the genome fragment, probe or both. Further exemplary hybridization conditions are set forth below in regard to particular detection methods.

A plurality of genome fragments that is contacted with probes in a method of the invention can represent all or part of a genome sequence. Accordingly, the complexity of the plurality of genome fragments can be equivalent to the size of the genome from which it was amplified or otherwise produced. For example, a plurality of human genome fragments that are contacted with probes can have a complexity of about 3.1 Gigabases which is roughly equivalent to the full length genome. Lower complexity representations can also be used. Again using the human genome as a non-limiting example, a plurality of genome fragments that are contacted with probes can have a complexity of at least about 2 Gigabases, which is a representation of about 60% of the human genome or a complexity of at least about 1 Gigabases, which is a representation of at least about 30% of the human genome. The complexity of a plurality of probes contacted with probes in a method of the invention can be, for example, at least about 0.1 Gigabases, 0.2 Gigabases, 0.5 Gigabases, 0.8 Gigabases, 1 Gigabases, 1.5 Gigabases, 2 Gigabases, 2.5 Gigabases, 3 Gigabases, 3.5 Gigabases, 4 Gigabases, 4.5 Gigabases, 5 Gigabases or more.

As higher complexity pluralities of genome fragments are used in a method of the invention it is typically desired to use larger amounts of DNA. Accordingly, the amount of DNA in a plurality of genome fragments that is contacted with probes in a method disclosed herein can be at least about 1 ug, 10 ug, 50 ug, 100 ug, 150 ug, 200 ug, 300 ug, 400 ug, 500 ug, 1000 ug or more (ug herein refers to a microgram). A plurality of genome fragments can be present in a fluid sample at any concentration that gives desired results such as a desired level of sequence-specific hybridization between probes and fragments or amount of loci detected. For example, the concentration of a plurality of genome fragments contacted with probes in a method of the invention can beat least about 0.1 ug/ul, 0.2 ug/ul, 0.5 ug/ul, 0.8 ug/ul, 1 ug/ul, 1.5 ug/ul, 2 ug/ul, 5 ug/ul, 10 ug/ul (ul herein refers to a microliter).

The number of probes contacted with a plurality of genome fragments can be selected based on a desired application of the methods. Exemplary probe populations and arrays that can be used include those known in the art and/or set forth herein. The number of different probes that form sequence-specific hybrids with genome fragments can be, for example, at least about 100, 500, 1000, 5000, $1\times10^4$, $5\times10^4$, $1\times10^5$, $5\times10^5$, $1\times10^6$, $5\times10^6$, or more including a number of probes in a population or array known in the art and/or set forth herein.

Following hybridization, non-hybridized nucleic acids can be separated from hybrids, if desired. Single strand nucleic acids and hybrid nucleic acids can be separated based on properties that differ for the two species including, for example, size, mass, energy absorbance, fluorescence, electrical conductivity, charge, or affinity for particular substrates. Exemplary methods that can be used to separate single strand nucleic acids and hybrid nucleic acids based on properties that differ for the two species include, but are not limited to, size exclusion chromatography, filtration through a membrane having a particular size cutoff, affinity chromatography, gel electrophoresis, capillary electrophoresis, fluorescent activated cell sorting (FACS), and the like.

In a particular embodiment, separation of single strand nucleic acids, such as probes, targets or both, from hybrid nucleic acids can be facilitated by attachment of the probe or target to a substrate. An exemplary method including separation of nucleic acids using a solid phase substrate is shown in FIG. 9 and described above. Hybrids formed on the substrate bound nucleic acid can be separated from non-hybridized nucleic acids by physical separation of the substrate from the reaction mixture. Exemplary substrates that can be used for such separation include, without limitation, particles such as magnetic beads, Sephadex™, controlled pore glass, agarose or the like; or surfaces such as glass surfaces, plastic, ceramics and the like. Nucleic acids can be attached to substrates via known linkers and ligands such as those set forth above in regard to nucleic acid secondary labels and using methods known in the art. Substrates can be physically separated from a solution by any of a variety of methods including, for example, magnetic attraction, gravity sedimentation, centrifugal sedimentation, filtration, FACS, electrical attraction or the like. Separation can also be carried out by manual movement of the substrate, for example, using the hands or a robotic device.

A method of the invention can further include a step of detecting typable loci of probe-genome fragment hybrids. Depending upon the particular application of the invention, probe-genome fragment hybrids can be detected using a direct detection technique, or alternatively an amplification-based technique. Direct detection techniques include those in which the level of nucleic acids in probe-fragment hybrids provides the detected signal. For example, in the case of a hybrid formed at a particular array location, the signal from the location arising from the captured hybrid or its component nucleic acids can be detected without amplifying the hybrid or its component nucleic acids. Alternatively, detection can include amplification of the probe or genome fragment or both to increase the level of nucleic acid that is detected. As set forth below in the context of various exemplary detection techniques, a probe nucleic acid, genome fragment or both can be labeled. Furthermore, nucleic acids in a probe-fragment hybrid can be labeled prior to, during or after hybrid formation and detection of typable loci based on detection of such labels Accordingly a method of detecting typable loci of a genome can include the steps of (a) providing an amplified representative population of genome fragments that has such typable loci, (b) contacting the genome fragments with a plurality of nucleic acid probes having sequences corresponding to the typable loci under conditions wherein probe-fragment hybrids are formed; and (c) directly detecting typable loci of the probe-fragment hybrids.

Generally, detection, whether direct or based on an amplification technique, can be achieved by methods that perceive properties that are intrinsic to nucleic acids or their associated labels. Useful properties include, for example, those that can be used to distinguish nucleic acids having typable loci from those lacking the loci. Such detected properties can be used to distinguish different nucleic acids alone or in combination with other methods such as attachment to discrete locations of a detection array. Exemplary properties upon which detection can be based include, but are not limited to, mass, electrical conductivity, energy absorbance, fluorescence or the like.

Detection of fluorescence can be carried out by irradiating a nucleic acid or its label with an excitatory wavelength of radiation and detecting radiation emitted from a fluorophore therein by methods known in the art and described for example in Lakowicz, *Principles of Fluorescence Spectroscopy,* 2nd Ed., Plenum Press New York (1999). A fluorophore can be detected based on any of a variety of fluorescence phenomena including, for example, emission wavelength, excitation wavelength, fluorescence resonance energy transfer (FRET) intensity, quenching, anisotropy or lifetime. FRET can be used to identify hybridization between a first polynucleotide attached to a donor fluorophore and a second polynucleotide attached to an acceptor fluorophore due to transfer of energy from the excited donor to the acceptor. Thus, hybridization can be detected as a shift in wavelength caused by reduction of donor emission and appearance of acceptor emission for the hybrid. In addition, fluorescence recovery after photobleaching (FRAP) can be used to identify hybridization according to the increase in fluorescence occurring at a previously photobleached array location due to binding of a fluorescently labeled target polynucleotide.

Other detection techniques that can be used to perceive or identify nucleic acids having typable loci include, for example, mass spectrometry which can be used to perceive a nucleic acid based on its mass; surface plasmon resonance which can be used to perceive a nucleic acid based on binding to a surface immobilized complementary sequence; absorbance spectroscopy which can be used to perceive a nucleic acid based on the wavelength of the energy it absorbs; calorimetry which can be used to perceive a nucleic acid based on changes in temperature of its environment due to binding to a complementary sequence; electrical conductance or impedance which can be used to perceive a nucleic acid based on changes in its, electrical properties or in the electrical properties of its environment, magnetic resonance which can be used to perceive a nucleic acid based on presence of magnetic nuclei, or other known analytic spectroscopic or chromatographic techniques.

In particular embodiments, typable loci of probe-fragment hybrids can be detected based on the presence of the probe, fragment or both in the hybrid, without subsequent modification of the hybrid species. For example, a pre-labeled fragment having a particular typable locus, can be identified based on presence of the label at a particular array location where a nucleic acid complement of the locus resides.

The invention further provides a method of detecting typable loci of a genome including the steps of (a) providing an amplified representative population of genome fragments having the typable loci; (b) contacting the genome fragments with a plurality of immobilized nucleic acid probes having sequences corresponding to the typable loci under conditions wherein immobilized probe-fragment hybrids are formed; (c) modifying the immobilized probe-fragment hybrids; and (d) detecting a probe or fragment that has been modified, thereby detecting the typable loci of the genome.

In a particular embodiment, arrayed nucleic acid probes can be modified while hybridized to genome fragments for detection. Such embodiments, include, for example, those utilizing ASPE, SBE, oligonucleotide ligation amplification (OLA), extension ligation (GOLDENGATE®), invader technology, probe cleavage or pyrosequencing as described in U.S. Pat. No. 6,355,431 B1, U.S. Ser. No. 10/177,727 and/or below. Thus, the invention can be carried out in a mode wherein an immobilized probe is modified instead of a genome fragment captured by a probe. Alternatively, detection can include modification of the genome fragments while hybridized to probes. Exemplary modifications include those that are catalyzed by an enzyme such as a polymerase. A useful modification can be incorporation of one or more nucleotides or nucleotide analogs to a primer hybridized to a template strand, wherein the primer can be either the probe or genome fragment in a probe-genome-fragment hybrid. Such a modification can include replication of all or part of a primed template. Modification leading to replication of only a part of a template probe or genome fragment will be understood to be detection without amplification of the template since the template is not replicated along its full length.

Extension assays are useful for detection of typable loci. Extension assays are generally carried out by modifying the 3' end of a first nucleic acid when hybridized to a second nucleic acid. The second nucleic acid can act as a template directing the type of modification, for example, by base pairing interactions that occur during polymerase-based extension of the first nucleic acid to incorporate one or more nucleotide. Polymerase extension assays are particularly useful, for example, due to the relative high-fidelity of polymerases and their relative ease of implementation. Extension assays can be carried out to modify nucleic acid probes that have free 3' ends, for example, when bound to a substrate such as an array. Exemplary approaches that can be used include, for example, allele-specific primer extension (ASPE), single base extension (SBE), or pyrosequencing.

Figure 2:
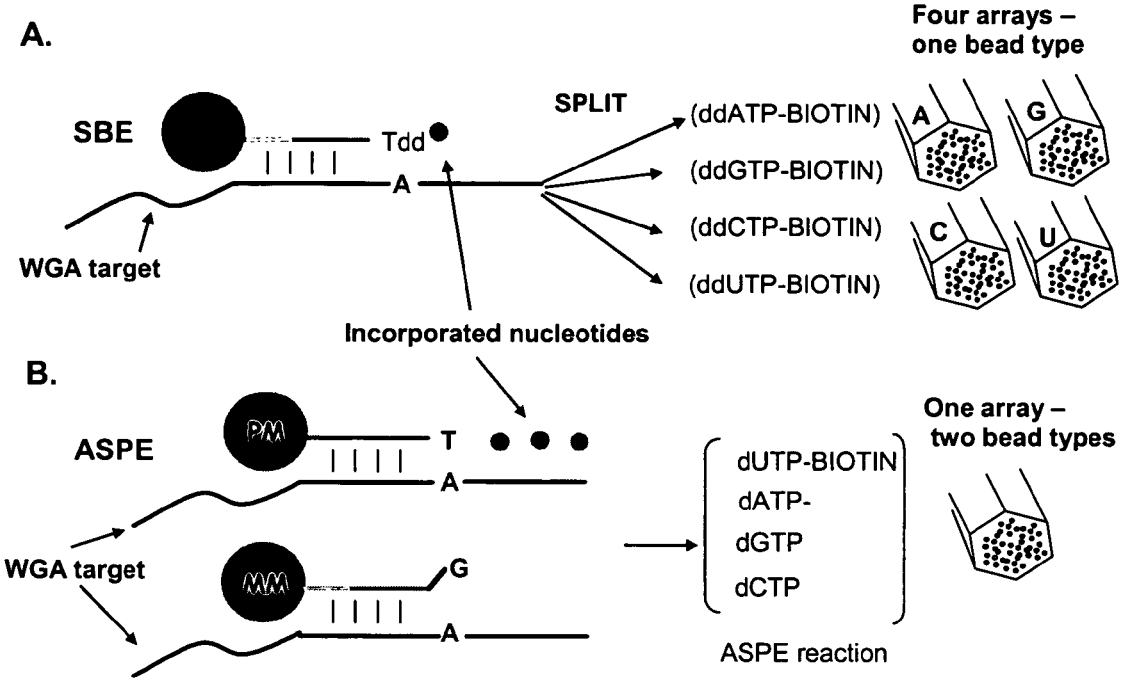
FIG. 2 shows exemplary probes useful for detection of typable loci using allele-specific primer extension (ASPE) or single base extension (SBE).

In particular embodiments, single base extension (SBE) can be used for detection of typable loci. An exemplary diagrammatic representation of SBE is shown in FIG. 2. Briefly, SBE utilizes an extension probe that hybridizes to a target genome fragment at a location that is proximal or adjacent to a detection position, the detection position being indicative of a particular typable locus. A polymerase can be used to extend the 3' end of the probe with a nucleotide analog labeled with a detection label such as those described previously herein. Based on the fidelity of the enzyme, a nucleotide is only incorporated into the extension probe if it is complementary to the detection position in the target genome fragment. If desired, the nucleotide can be derivatized such that no further extensions can occur, and thus only a single nucleotide is added. The presence of the labeled nucleotide in the extended probe can be detected, for example, at a particular location in an array and the added nucleotide identified to determine the identity of the typable locus. SBE can be carried out under known conditions such as those described in U.S. patent application Ser. No. 09/425,633. A labeled nucleotide can be detected using methods such as those set forth above or described elsewhere such as Syvanen et al., *Genomics* 8:684-692 (1990); Syvanen et al., *Human Mutation* 3:172-179 (1994); U.S. Pat. Nos. 5,846,710 and 5,888,819; Pastinen et al., *Genomics Res.* 7(6):606-614 (1997).

A nucleotide analog useful for SBE detection can include a dideoxynucleoside-triphosphate (also called deoxynucleotides or ddNTPs, i.e. ddATP, ddTTP, ddCTP and ddGTP), or other nucleotide analogs that are derivatized to be chain terminating. The use of labeled chain terminating nucleotides is useful, for example, in reactions having more than one type of dNTP present so as to prevent false positives due to extension beyond the detection position. Exemplary analogs are dideoxy-triphosphate nucleotides (ddNTPs) or acyclo terminators (Perkin Elmer, Foster City, Calif.). Generally, a set of nucleotides comprising ddATP, ddCTP, ddGTP and ddTTP can be used, at least one of which includes a label. If desired for a particular application, a set of nucleotides in which all four are labeled can be used. The labels can all be the same or, alternatively, different nucleotide types can have different labels. As will be appreciated by those in the art, any number of nucleotides or analogs thereof can be added to a primer, as long as a polymerase enzyme incorporates a particular nucleotide of interest at an interrogation position that is indicative of a typable locus.

A nucleotide used in an SBE detection method can further include, for example, a detectable label, which can be either a primary or secondary detectable label. Any of a variety of the nucleic acid labels set forth previously herein can be used in an SBE detection method. The use of secondary labels can also facilitate the removal of unextended probes in particular embodiments.

The solution for SBE can also include an extension enzyme, such as a DNA polymerase. Suitable DNA polymerases include, but are not limited to, the Klenow fragment of DNA polymerase I, SEQUENASE™ 1.0 and SEQUENASE™ 2.0 (U.S. Biochemical), T5 DNA polymerase, Phi29 DNA polymerase, Thermosequenase™ (Taq with the Tabor-Richardson mutation) and others known in the art or described herein. If the nucleotide is complementary to the base of the detection position of the target sequence, which is adjacent to the extension primer, the extension enzyme will add it to the extension primer. Thus, the extension primer is modified, i.e. extended, to form a modified primer.

In embodiments where the amount of unextended primer in the reaction greatly exceeds the resultant extended-labeled primer and the excess of unextended primer competes with the detection of the labeled primer, unextended primers can be removed. For example, unextended primers can be removed from SBE reactions that are run with small amounts of DNA target. Useful methods for removing unextended primers are set forth herein. Furthermore, single stranded probes can be preferentially removed from an array of probes, leaving double-stranded probe-target hybrids using methods set forth in further detail below such as exonuclease treatment. Such methods can provide increased assay sensitivity and selective detection, for example, by removing background arising from non-template directed probe labeling.

As will be appreciated by those in the art, the configuration of an SBE reaction can take on any of several forms. In particular embodiments, the reaction can be done in solution, and then the newly synthesized strands, with the base-specific detectable labels, can be detected. For example, they can be directly hybridized to capture probes that are complementary to the extension primers, and the presence of the label can then be detected. Such a configuration is useful, for example, when genome fragments are arrayed as capture probes. Alternatively, the SBE reaction can occur on a surface. For example, a genome fragment can be captured using a first capture probe that hybridizes to a first target domain of the fragment, and the reaction can proceed such that the probe is modified as shown in FIG. 2A.

The determination of the base at the detection position can proceed in any of several ways. In a particular embodiment, a mixed reaction can be run with two, three or four different nucleotides, each with a different label. In this embodiment, the label on the probe can be distinguished from non incorporated labels to determine which nucleotide has been incorporated into the probe. Alternatively, discrete reactions can be run each with a different labeled nucleotide. This can be done either by using a single substrate bound probe and sequential reactions, or by exposing the same reaction to multiple substrate-bound probes, the latter case being shown in FIG. 2A. For example, dATP can be added to a probe-fragment hybrid, and the generation of a signal evaluated; the dATP can be removed and dTTP added, etc. Alternatively, four arrays can be used; the first is reacted with dATP, the second with dTTP, etc., and the presence or absence of a signal evaluated in each array.

Alternatively, a ratiometric analysis can be done; for example, two labels, "A" and "B", on two substrates (e.g. two arrays) can be detected. In this embodiment, two sets of primer extension reactions are performed, each on two arrays, with each reaction containing a complete set of four chain terminating NTPs. The first reaction contains two "A" labeled nucleotides and two "B" labeled nucleotides (for example, A and C can be "A" labeled, and G and T can be "B" labeled). The second reaction also contains the two labels, but switched; for example, A and G are "A" labeled and T and C are "B" labeled. This reaction composition allows a biallelic marker to be ratiometrically scored; that is, the intensity of the two labels in two different "color" channels on a single substrate is compared, using data from a set of two hybridized arrays. For instance, if the marker is A/G, then the first reaction on the first array is used to calculate a ratiometric genotyping score; if the marker is A/C, then the second reaction on the second array is used for the calculation; if the marker is G/T, then the second array is used, etc. This concept can be applied to all possible biallelic marker combinations. In this way, scoring a genotype using a single fiber ratiometric score can allow a more robust genotyping than scoring a genotype using a comparison of absolute or normalized intensities between two different arrays.

The SBE reaction exemplified in FIG. 2, demonstrates an embodiment in which four separate reactions are carried out on four separate arrays using a single label. Further embodiments can include use of more than one type of label in combination with fewer than four probe populations or arrays. For example, SBE can be carried out in a two color mode using a single reaction and a single probe population. In this mode, all four chain terminating nucleotides can be present with two of the nucleotides bearing a first type of label and the other two bearing a second type of label. The first label can be used for A and C, whereas the second label is used for G and T (or G and U). This exemplary labeling scheme allows detection of almost 80% of naturally occurring human SNPs since the most abundant human SNPs are A/G and C/T polymorphisms. Those skilled in the art will recognize that other labeling schemes can be used if desired, for example, to conform to the abundance of polymorphisms in a particular organism or to conform to the desired types of polymorphisms to be detected in a particular application. The use of SBE with multiple label types can provide the non-limiting advantage of reducing the number of arrays and reactions required to obtain genotyping data.

Single base sequencing (SBS) is an extension assay that can be carried out as set forth above for SBE with the exception that one or more non-chain terminating nucleotides are included in the extension reaction. Thus, in accordance with the invention, one or more non-chain terminating nucleotides can be included in an SBE reaction including, for example, those set forth above.

An exemplary embodiment of SBS is to carry out two separate reactions on two separate probe populations. The two separate reactions are advantageously carried out using a single label; however, if desired more than one type of label can be used. The first reaction can include 2 different labeled nucleotides that are extendable and capable of hybridizing to 2 of the 4 naturally occurring nucleotides in the genomic DNA. The second reaction can include 2 different nucleotides, the nucleotides being labeled and capable of hybridizing to the other 2 naturally occurring nucleotides in the genomic DNA. Each of the two reactions can be devoid of the nucleotides found in the other reaction or can include chain terminating analogs of the nucleotides found in the other reaction. By way of example, the first reaction (hot AC reaction) can include dATP-biotin and dCTP-biotin. This first reaction can lack GTP, UTP and TTP. Alternatively, the first reaction can include dideoxyGTP and dideoxyUTP (or dideoxyGTP and dideoxyTTP). Continuing with the example, the second reaction (hot GU reaction) can include dGTP-biotin and dUTP-biotin (or dGTP-biotin and dTTP-biotin). This second reaction can lack CTP or ATP. Alternatively, the second reaction can include dideoxyCTP and dideoxyATP. This exemplary labeling scheme allows detection of almost 80% of naturally occurring human SNPs since the most abundant human SNPs are A/G and C/T polymorphisms.

ASPE is an extension assay that utilizes extension probes that differ in nucleotide composition at their 3' end. An exemplary diagrammatic representation of ASPE is shown in FIG. 2B. Briefly, ASPE can be carried out by hybridizing a target genome fragment to an extension probe having a 3' sequence portion that is complementary to a detection position and a 5' portion that is complementary to a sequence that is adjacent to the detection position. Template directed modification of the 3' portion of the probe, for example, by addition of a labeled nucleotide by a polymerase yields a labeled extension product, but only if the template includes the target sequence. The presence of such a labeled primer-extension product can then be detected, for example, based on its location in an array to indicate the presence of a particular typable locus.

In particular embodiments, ASPE can be carried out with multiple extension probes that have similar 5' ends such that they anneal adjacent to the same detection position in a target genome fragment but different 3' ends, such that only probes having a 3' end that complements the detection position are modified by a polymerase. As shown in FIG. 2B, a probe having a 3' terminal base that is complementary to a particular detection position is referred to as a perfect match (PM) probe for the position, whereas probes that have a 3' terminal mismatch base and are not capable of being extended in an ASPE reaction are mismatch (MM) probes for the position. The presence of the labeled nucleotide in the PM probe can be detected and the 3' sequence of the probe determined to identify a particular typable locus. An ASPE reaction can include 1, 2, or 3 different MM probes, for example, at discrete array locations, the number being chosen depending upon the diversity occurring at the particular locus being assayed. For example, two probes can be used to determine which of 2 alleles for a particular locus are present in a sample, whereas three different probes can be used to distinguish the alleles of a 3-allele locus.

In particular embodiments, an ASPE reaction can include a nucleotide analog that is derivatized to be chain terminating. Thus, a PM probe in a probe-fragment hybrid can be modified to incorporate a single nucleotide analog without further extension. Exemplary chain terminating nucleotide analogs include, without limitation, those set forth above in regard to the SBE reaction. Furthermore, one or more nucleotides used in an ASPE reaction whether or not they are chain terminating can include a detection label such as those described previously herein. For example, an ASPE reaction can include a single biotin labeled dNTP as exemplified in Example III. If desired, more than one nucleotide in an ASPE reaction can be labeled. For example reaction conditions such as those described in Example II can be modified to include biotinylated dCTP as well as biotinylated dGTP and biotinylated dTTP. An ASPE reaction can be carried out in the presence of all four nucleotides A, C, T, and G or in the presence of a subset of these nucleotides including, for example, a subset that lacks substantial amounts of one or more of A, C, T or G.

Pyrosequencing is an extension assay that can be used to add one or more nucleotides to a detection position(s); it is similar to SBE except that identification of typable loci is based on detection of a reaction product, pyrophosphate (PPi), produced during the addition of a dNTP to an extended probe, rather than on a label attached to the nucleotide. One molecule of PPi is produced per dNTP added to the extension primer. That is, by running sequential reactions with each of the nucleotides, and monitoring the reaction products, the identity of the added base is determined. Pyrosequencing can be used in the invention using conditions such as those described in US 2002/0001801.

In particular embodiments, modification of immobilized probe-fragment hybrids can include cleavage or degradation of hybrids having one or more mismatched base pair. As with other modifications set forth herein, conditions can be employed that result in selective modification of hybrids having one or more mismatch compared to perfectly matched hybrids. For example, in an ASPE-based detection method, mismatch probe-fragment hybrids can be selectively cleaved or degraded compared to perfect match probe-fragment hybrids. For example, a hybrid can be contacted with an agent that is capable of recognizing a base pair mismatch and modifying the mismatched hybrid such as by bond cleavage. Exemplary agents include enzymes that recognize and cleave hybrids having mismatched base pairs such as a DNA glycosylase, Cel I, T4 endonuclease VII, T7 endonuclease I, mung bean endonuclease or Mut-y or others such as those described in Bradley et al., *Nucl. Acids Res.* 32:2632-2641 (2004). Cleavage products produced from mismatched hybrids can be removed, for example, by washing.

Accordingly, a method of the invention can include modifying immobilized probe-fragment hybrids using ASPE along with cleavage of mismatch probe-fragment hybrids. An advantage of using both modification steps in combination is that specificity can be increased compared to use of only one of the steps. For example, in cases wherein ASPE detection is used a first level of specificity is obtained due to differentiation of match and mismatch primers by the extending polymerase. In cases where unwanted mismatch primer extension occurs, cleavage of mismatched hybrids can act to prevent artifact signal due to mismatch probes, thereby increasing assay specificity and sensitivity. Similarly, specificity and sensitivity can be increased by removing artifact signal arising due to mismatch hybrids formed in other detection methods set forth herein such as ligation based assays. Mismatch hybrids can be removed from solution phase or solid phase immobilized hybrids in accordance with the methods disclosed herein.

In a particular embodiment, an ASPE reaction can be carried out under conditions in which extension of perfect match probe-fragment hybrids is driven to completion and substantial amounts of mismatch probe-fragment hybrids are also extended. For example, in the case of a locus having an A and B allele, the perfect match probe can be designed against the homozygous allele A forming a perfect hybrid with an AA individual and the mismatch probe can be designed against the homozygous allele B, forming a perfect hybrid with a BB individual. Accordingly, the role of the perfect match and mismatch probe can be reversed depending on the sample under observation. The product of a mismatch extension will have one mismatch base pair in the extended product and the perfect match will not contain a mismatch. Specific removal of the signal generated by the mismatch probe, while leaving the signal from the perfect match extension intact can add a second discrimination step to create a larger distinction between the perfect match and mismatch, creating a more specific genotyping assay compared to detection based solely on polymerase-based modification of perfect match probes.

If desired, an immobilized probe that is not part of a probe-fragment hybrid can be selectively modified compared to a probe-fragment hybrid. Selective modification of non-hybridized probes can be used to increase assay specificity and sensitivity, for example, by removing probes that are labeled in a template independent manner during the course of a polymerase extension assay. A particularly useful selective modification is degradation or cleavage of single stranded probes that are present in a population or array of probes following contact with target fragments under hybridization conditions. Exemplary enzymes that degrade single stranded nucleic acids include, without limitation, Exonuclease 1 or lambda Exonuclease.

In embodiments utilizing probes with reactive hydroxyls at their 3' ends and polymerase extension, a useful exonuclease is one that preferentially digests single stranded DNA in the 3' to 5' detection. Thus, double stranded probe-target hybrids that form under particular assay conditions are preferentially protected from degradation as is the 3' overhang of the target that serves as a template for polymerase extension of the probe. However, single stranded probes not hybridized to target under the assay conditions are preferentially degraded. Furthermore, such exonuclease treatment can preferentially degrade single stranded regions of genome fragments or other nucleic acids in cases where the fragments or nucleic acids are retained by an array due to interaction with non-probe interacting portions of target nucleic acids. Thus, exonuclease treatment can prevent artifacts that may arise due to a bridged network of 2 or more nucleic acids bound to a probe. Digestion with exonuclease is typically carried out after a probe extension step.

In some embodiments, detection of typable loci can include amplification of genome-fragment targets following formation of probe-fragment hybrids, resulting in a significant increase in the number of target molecules. Target amplification-based detection techniques can include, for example, the polymerase chain reaction (PCR), strand displacement amplification (SDA), or nucleic acid sequence based amplification (NASBA). Alternatively, rather than amplify the target, alternate techniques can use the target as a template to replicate a hybridized probe, allowing a small number of target molecules to result in a large number of signaling probes, that then can be detected. Probe amplification-based strategies include, for example, the ligase chain reaction (LCR), cycling probe technology (CPT), invasive cleavage techniques such as Invader™ technology, Q-Beta replicase (QβR) technology or sandwich assays. Such techniques can be carried out, for example, under conditions described in U.S. Ser. No. 60/161,148, 09/553,993 and 090/556,463; and U.S. Pat. No. 6,355,431 B1, or as set forth below. These techniques are exemplified below, in the context of genome fragments used as target nucleic acids that are hybridized to arrayed nucleic acid probes. It will be understood that in such embodiments genome fragments can be arrayed as probes and hybridized to synthetic nucleic acid targets.

Detection with oligonucleotide ligation amplification (OLA) involves the template-dependent ligation of two smaller probes into a single long probe, using a genome-fragment target sequence as the template. In a particular embodiment, a single-stranded target sequence includes a first target domain and a second target domain, which are adjacent and contiguous. A first OLA probe and a second OLA probe can be hybridized to complementary sequences of the respective target domains. The two OLA probes are then covalently attached to each other to form a modified probe. In embodiments where the probes hybridize directly adjacent to each other, covalent linkage can occur via a ligase. In one embodiment one of the ligation probes may be attached to a surface such as an array or a particle. In another embodiment both ligation probes may be attached to a surface such as an array or a particle.

Alternatively, an extension ligation (GOLDENGATE®) assay can be used wherein hybridized probes are non-contiguous and one or more nucleotides are added along with one or more agents that join the probes via the added nucleotides. Exemplary agents include, for example, polymerases and ligases. If desired, hybrids between modified probes and targets can be denatured, and the process repeated for amplification leading to generation of a pool of ligated probes. As above, these extension-ligation probes can be but need not be attached to a surface such as an array or a particle. Further conditions for extension ligation assay that are useful in the invention are described, for example, in U.S. Pat. No. 6,355,431 B1 and U.S. application Ser. No. 10/177,727.

OLA is referred to as the ligation chain reaction (LCR) when double-stranded genome fragment targets are used. In LCR, the target sequence can be denatured, and two sets of probes added: one set as outlined above for one strand of the target, and a separate set (i.e. third and fourth primer probe nucleic acids) for the other strand of the target. Conditions can be used in which the first and second probes hybridize to the target and are modified to form an extended probe. Following denaturation of the target-modified probe hybrid, the modified probe can be used as a template, in addition to the second target sequence, for the attachment of the third and fourth probes. Similarly, the ligated third and fourth probes can serve as a template for the attachment of the first and second probes, in addition to the first target strand. In this way, an exponential, rather than just a linear, amplification can occur when the process of denaturation and ligation is repeated.

The modified OLA probe product can be detected in any of a variety of ways. In a particular embodiment, a template-directed probe modification reaction can be carried out in solution and the modified probe hybridized to a capture probe in an array. A capture probe is generally complementary to at least a portion of the modified OLA probe. In an exemplary embodiment, the first OLA probe can include a detectable label and the second OLA probe can be substantially complementary to the capture probe. A non-limiting advantage of this embodiment is that artifacts due to the presence of labeled probes that are not modified in the assay are minimized because the unmodified probes do not include the complementary sequence that is hybridized by the capture probe. An OLA detection technique can also include a step of removing unmodified labeled probes from a reaction mixture prior to contacting the reaction mixture with a capture probe as described for example in U.S. Pat. No. 6,355,431 B1.

Alternatively, a genome fragment target can be immobilized on a solid-phase surface and a reaction to modify hybridized OLA probes performed on the solid phase surface. Unmodified probes can be removed by washing under appropriate stringency. The modified probes can then be eluted from the genome fragment target using denaturing conditions, such as, 0.1 N NaOH, and detected as described herein. Other conditions in which a genome fragment can be detected when used as a target sequence in an OLA technique include, for example, those described in U.S. Pat. Nos. 6,355,431 B1, 5,185,243, 5,679,524 and 5,573,907; EP 0 320 308 B1; EP 0 336 731 B1; EP 0 439 182 B1; WO 90/01069; WO 89/12696; WO 97/31256; and WO 89/09835, and U.S. Ser. Nos. 60/078,102 and 60/073,011.

Typable loci can be detected in a method of the invention using rolling circle amplification (RCA). In a first embodiment, a single probe can be hybridized to a genome fragment target such that the probe is circularized while hybridized to the target. Each terminus of the probe hybridizes adjacently on the target nucleic acid and addition of a polymerase results in extension of the circular probe. However, since the probe has no terminus, the polymerase continues to extend the probe repeatedly. This results in amplification of the circular probe. Following RCA the amplified circular probe can be detected. This can be accomplished in a variety of ways; for example, the primer can be labeled or the polymerase can incorporate labeled nucleotides and labeled product detected by a capture probe in a detection array. Rolling-circle amplification can be carried out under conditions such as those generally described in Baner et al. (1998) *Nuc. Acids Res.* 26:5073-5078; Barany, F. (1991) *Proc. Natl. Acad. Sci. USA* 88:189-193; and Lizardi et al. (1998) *Nat Genet.* 19:225-232.

Furthermore, rolling circle probes used in the invention can have structural features that render them unable to be replicated when not annealed to a target. For example, one or both of the termini that anneal to the target can have a sequence that forms an intramolecular stem structure, such as a hairpin structure. The stem structure can be made of a sequence that allows the open circle probe to be circularized when hybridized to a legitimate target sequence but results in inactivation of uncircularized open circle probes. This inactivation reduces or eliminates the ability of the open circle probe to prime synthesis of a modified probe in a detection assay or to serve as a template for rolling circle amplification. Exemplary probes capable of forming intramolecular stem structures and methods for their use which can be used in the invention are described in U.S. Pat. No. 6,573,051.

In another embodiment, detection can include OLA followed by RCA. In this embodiment, an immobilized primer can be contacted with a genome fragment target. Complementary sequences will hybridize with each other resulting in an immobilized duplex. A second primer can also be contacted with the target nucleic acid. The second primer hybridizes to the target nucleic acid adjacent to the first primer. An OLA reaction can be carried out to attach the first and second primer as a modified primer product, for example, as described above. The genome fragment can then be removed and the immobilized modified primer product, hybridized with an RCA probe that is complementary to the modified primer product but not the unmodified immobilized primer. An RCA reaction can then be performed.

In a particular embodiment, a padlock probe can be used both for OLA and as the circular template for RCA. Each terminus of the padlock probe can contain a sequence complementary to a genome fragment target. More specifically, the first end of the padlock probe can be substantially complementary to a first target domain, and the second end of the RCA probe can be substantially complementary to a second target domain, adjacent to the first domain. Hybridization of the padlock probe to the genome fragment target results in the formation of a hybridization complex. Ligation of the discrete ends of a single oligonucleotide results in the formation of a modified hybridization complex containing a circular probe that acts as an RCA template complex. Addition of a polymerase to the RCA template complex can allow formation of an amplified product nucleic acid. Following RCA, the amplified product nucleic acid can be detected, for example, by hybridization to an array either directly or indirectly and an associated label detected.

A padlock probe used in the invention can further include other characteristics such as an adaptor sequence, restriction site for cleaving concatamers, a label sequence, or a priming site for priming the RCA reaction as described, for example, in U.S. Pat. No. 6,355,431 B1. This same patent also describes padlock probe methods that can be used to detect typable loci of genome fragment targets in a method of the invention.

A variation of LCR that can be used to detect typable loci in a method of the invention utilizes chemical ligation under conditions such as those described in U.S. Pat. Nos. 5,616,464 and 5,767,259. In this embodiment, similar to enzymatic modification, a pair of probes can be utilized, wherein the first probe is substantially complementary to a first domain of a target genome fragment and the second probe is substantially complementary to an adjacent second domain of the target. Each probe can include a portion that acts as a "side chain" that forms one half of a non-covalent stem structure between the probes rather than binding the target sequence. Particular embodiments utilize substantially complementary nucleic acids as the side chains. Thus, upon hybridization of the probes to the target sequence, the side chains of the probes are brought into spatial proximity. At least one of the side chains can include an activatable cross-linking agent, generally covalently attached to the side chain, that upon activation, results in a chemical cross-link or chemical ligation with the adjacent probe. The activatable group can include any moiety that will allow cross-linking of the side chains, and include groups activated chemically, photonically or thermally, such as photoactivatable groups. In some embodiments a single activatable group on one of the side chains is enough to result in cross-linking via interaction to a functional group on the other side chain; in alternate embodiments, activatable groups can be included on each side chain. One or both of the probes can be labeled Once a hybridization complex is formed, and the cross-linking agent has been activated such that the probes have been covalently attached to each other, the reaction can be subjected to conditions to allow for the disassocation of the hybridization complex, thus freeing up the target to serve as a template for the next ligation or cross-linking. In this way, signal amplification can occur, and the cross-linked products can be detected, for example, by hybridization to an array either directly or indirectly and an associated label detected.

In particular embodiments, amplification-based detection can be achieved using invasive cleavage technology. Using such an approach, a genome fragment target can be hybridized to two distinct probes. The two probes are an invader probe, which is substantially complementary to a first portion of the genome fragment target, and a signal probe, which has a 3' end substantially complementary to a sequence having a detection position and a 5' non-complementary end which can form a single-stranded tail. The tail can include a detection sequence and typically also contains at least one detectable label. However, since a detection sequence in a signal probe can function as a target sequence for a capture probe, sandwich configurations utilizing label probes can be used as described herein and the signal probe need not include a detectable label.

Hybridization of the invader and signal probes near or adjacent to one another on a genome fragment target can form any of several structures useful for detection of the probe-fragment hybrid. For example, a forked cleavage structure can form, thereby providing a substrate for a nuclease which cleaves the detection sequence from the signal probe. The site of cleavage is controlled by the distance or overlap between the 3' end of the invader probe and the downstream fork of the signal probe. Therefore, neither oligonucleotide is cleaved when misaligned or when unattached to a genome fragment target.

In particular embodiments, a thermostable nuclease that recognizes the forked cleavage structure and catalyzes release of the tail can be used, thereby allowing thermal cycling of the cleavage reaction and amplified, if desired. Exemplary nucleases that can be used include, without limitation, those derived from *Thermus aquaticus, Thermus flavus,* or *Thermus thermophilus*; those described in U.S. Pat. Nos. 5,719,028 and 5,843,669, or Flap endonucleases (FENs) as described, for example, in U.S. Pat. No. 5,843,669 and Lyamichev et al., *Nature Biotechnology* 17:292-297 (1999).

If desired, the 3' portion of a cleaved signal probe can be extracted, for example, by binding to a solid-phase capture tag such as, bead bound streptavidin, or by crosslinking through a capture tag to produce aggregates. The 5' detection sequence of a signal probe, can be detected using methods set forth below such as hybridization to a probe on an array. Invasive cleavage technology can further be used in the invention using conditions and detection methods described, for example, in U.S. Pat. Nos. 6,355,431; 5,846,717; 5,614,402; 5,719,028; 5,541,311; or 5,843,669.

A further amplification-based detection technique that can be used to detect typable loci is cycling probe technology (CPT). A CPT probe can include two probe sequences separated by a scissile linkage. The CPT probe is substantially complementary to a genome fragment target sequence and thus will hybridize to it to form a probe-fragment hybrid. The CPT probe can be hybridized to a genome fragment target in a method of the invention. Typically the temperature and probe sequence are selected such that the primary probe will bind and shorter cleaved portions of the primary probe will dissociate. Depending upon the particular application, CPT can be done in solution, or either the target or scissile probe can be attached to a solid support. A probe-fragment hybrid formed in the methods can be subjected to cleavage conditions which cause the scissile linkage to be selectively cleaved, without cleaving the target sequence, thereby separating the two probe sequences. The two probe sequences can then be disassociated from the target. In particular embodiments, excess probe can be used and the reaction allowed to be repeated any number of times such that the effective amount of cleaved probe is amplified.

Any linkage within a CPT probe that can be selectively cleaved when the probe is part of a hybridization complex, that is, when a double-stranded complex is formed can be used as a scissile linkage. Any of a variety of scissile linkages can be used in the invention including, for example, RNA which can be cleaved when in a DNA:RNA hybrid by various double-stranded nucleases such as ribonucleases. Such nucleases will selectively nick or excise RNA nucleosides from a RNA:DNA hybridization complex rather than DNA in such a hybrid or single stranded DNA. Further examples of scissile linkages and cleaving agents that can be used in the invention are described in U.S. Pat. No. 6,355,431 B1 and references cited therein.

Upon completion of a CPT cleavage reaction, the uncleaved scissile probes can be removed or neutralized prior to detection of cleaved probes to avoid false positive signals, if desired. This can be done in any of a variety of ways including, for example, attachment of the probes to a solid support prior to cleavage such that following the CPT reaction, cleaved probes that have been released into solution can be physically separated from uncleaved probes remaining on the support. Uncleaved and cleaved probes can also be separated based on differences in length, capture of a particular binding label or sequence using, for example, methods described in U.S. Pat. No. 6,355,431.

Cleaved probes produced by a CPT reaction can be detected using methods such as hybridization to an array or other methods set forth herein. For example, a cleaved probe can be bound to a capture probe, either directly or indirectly, and an associated label detected. CPT technology can be carried out under conditions described, for example, in U.S. Pat. Nos. 5,011,769; 5,403,711; 5,660,988; and 4,876,187, and PCT published applications WO 95/05480; WO 95/1416, and WO 95/00667, and U.S. Ser. No. 09/014,304.

In particular embodiments, CPT with a probe containing a scissile linkage can be used to detect mismatches, is generally described in U.S. Pat. No. 5,660,988, and WO 95/14106. In such embodiments, the sequence of the scissile linkage can be placed at a position within a longer sequence that corresponds to a particular sequence to be detected, i.e. the area of a putative mismatch. In some embodiments of mismatch detection, the rate of generation of released fragments is such that the methods provide, essentially, a yes/no result, whereby the detection of virtually any released fragment indicates the presence of a desired typable locus. Alternatively or additionally, the final amount of cleaved fragments can be quantified to indicate the presence or absence of a typable locus.

Typable loci of probe-fragment hybrids can also be detected in a method of the invention using a sandwich assay. A sandwich assay is an amplification-based technique in which multiple probes, typically labeled, are bound to a single genome fragment target. In an exemplary embodiment a genome fragment target can be bound to a solid substrate via a complementary capture probe. Typically, a unique capture probe will be present for each typable locus sequence to be detected. In the case of a bead array, each bead can have one of the unique capture probes. If desired, capture extender probes can be used, that allow a universal surface to have a single type of capture probe that can be used to detect multiple target sequences. Capture extender probes include a first portion that will hybridize to all or part of the capture probe, and a second portion that will hybridize to a first portion of the target sequence to be detected. Accordingly customized soluble probes can be generated, which as will be appreciated by those in the art can simplify and reduce costs in many applications of the invention. In particular embodiments, two capture extender probes can be used. This can provide, a non-limiting advantage of stabilizing assay complexes, for example, when a target sequence to be detected is large, or when large amplifier probes (particularly branched or dendrimer amplifier probes) are used.

Once a genome fragment target has been bound to a solid substrate, such as a bead, via a capture probe, an amplifier probe can be hybridized to the fragment to form a probe-fragment hybrid. Exemplary amplifier probes that can be used in a method of the invention and conditions for their use in sandwich assays are described in U.S. Pat. No. 6,355,431. Briefly, an amplifier probe is a nucleic acid having at least one probe sequence, and at least one amplification sequence. A first probe sequence of an amplifier probe can be used, either directly or indirectly, to hybridize to a genome fragment target sequence. An amplification sequence of an amplifier probe can be any of a variety of sequences that are used, either directly or indirectly, to bind to a first portion of a label probe. Typically an amplifier probe will include a plurality of amplification sequences. The amplification sequences can be linked to each other in a variety of ways including, for example, covalently linked directly to each other, or to intervening sequences or chemical moieties.

Label probes comprising detectable labels can hybridize to genome fragments thereby forming probe-fragment hybrids and the labels can be detected to determine the presence of typable loci. The amplification sequences of the amplifier probe can be used, either directly or indirectly, to bind to a label probe to allow detection. Detection of the amplification reactions of the invention, including the direct detection of amplification products and indirect detection utilizing label probes (i.e. sandwich assays), can be done by detecting assay complexes having labels. Exemplary methods for using a sandwich assay and associated nucleic acids that can be used in the present invention are further described in U.S. Ser. No. 60/073,011 and in U.S. Pat. Nos. 6,355,431; 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246 and 5,681,697.

Depending upon a particular application of the methods of the invention, the detection techniques set forth above can be used to detect primary genome fragment targets or to detect targets in an amplified representative population of genome fragments.

In particular embodiments, it can be desirable to remove unextended or unreacted nucleic acids from a reaction mixture prior to detection since unextended or unreacted primers can often compete with the modified probes during detection, thereby diminishing the signal. The concentration of the unmodified probes relative to modified probes can often be relatively high, for example in embodiments where a large excess of probe is used. Accordingly, a number of different techniques can be used to facilitate the removal of unextended primers. Exemplary methods that can be used to remove unextended primers include, for example, those described in U.S. Pat. No. 6,355,431.

As set forth above, the invention can be used to detect one or more typable loci. In particular, the invention is well suited to detection of a plurality of typable loci because the methods allow individual loci to be distinguished within large and complex pluralities. Individual typable loci can be distinguished in the invention based on separation of the loci into individual genome fragments, formation of probe-fragment hybrids and detection of physically separated probe-fragment hybrids. Physical separation of probe-fragment hybrids can be achieved in the invention by binding the hybrids or their components to one or more substrates. In particular embodiments, a probe-fragment hybrid can be distinguished from other probes and fragments in a plurality based on the physical location of the hybrid on the surface of a substrate such as an array. A probe-fragment hybrid can also be bound to a particle. Particles can be discretely detected based on their location and distinguished from other probes and fragments according to discrete detection of the particle on a surface such as a bead array or in a fluid sample such as a fluid stream in a flow cytometer. Exemplary formats for distinguishing probe-fragment hybrids for detection of individual typable loci are set forth in further detail below.

Detection of typable loci in an amplified representative population of genome fragments can employ arrays. In embodiments where relatively large numbers of loci are to be detected, arrays are preferably high density arrays. Exemplary microarrays that can be used in the invention include, without limitation, those described in Butte, *Nature Reviews Drug Discov.* 1:951-60 (2002) or U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897. Further examples of array formats that are useful in the invention are described in U.S. Pat. No. 6,355,431 B1, US 2002/0102578 and PCT Publication No. WO 00/63437. Exemplary formats that can be used in the invention to distinguish beads in a fluid sample using microfluidic devices are described, for example, in U.S. Pat. No. 6,524,793. Commercially available fluid formats for distinguishing beads include, for example, those used in xMAP™ technologies from Luminex or MPSS™ methods from Lynx Therapeutics. Various techniques and technologies may be used for synthesizing arrays of biological materials on or in a substrate or support to form microarrays. For example, Affymetrix® GeneChip® arrays can be synthesized in accordance with techniques sometimes referred to as VLSIPS™ (Very Large Scale Immobilized Polymer Synthesis) technologies. Some aspects of VLSIPS™ and other microarray and polymer (including protein) array manufacturing methods and techniques have been described in U.S. Ser. No. 09/536,841, International Publication No. WO 00/58516; U.S. Pat. Nos. 5,143,854, 5,242,974, 5,252,743, 5,324,633, 5,445,934, 5,744,305, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846, 6,022,963, 6,083,697, 6,291,183, 6,309,831 and 6,428,752; and in PCT Applications Nos. PCT/US99/00730 (International Publication No. WO 99/36760) and PCT/US01/04285.

Using VLSIPS™, a GeneChip array can be manufactured by reacting the hydroxylated surface of a 5-inch square quartz wafer with silane. Linkers can then be attached to the silane molecules. The distance between these silane molecules determines the probes' packing density, allowing arrays to hold over 500,000 probe locations, or features, within a mere 1.28 square centimeters. Millions of identical DNA molecules can be synthesized at each feature using a photolithographic process in which masks, carrying 18 to 20 square micron windows that correspond to the dimensions of individual features, are placed over the coated wafer. When ultraviolet light is shone over the mask in the first step of synthesis, the exposed linkers become deprotected and are available for nucleotide coupling. Once the desired features have been activated, a solution containing a single type of deoxynucleotide with a removable protection group can be flushed over the wafer's surface. The nucleotide attaches to the activated linkers, initiating the synthesis process. A capping step can be used to truncate unreacted linkers (or polynucleotides in subsequent step). In the next synthesis step, another mask can be placed over the wafer to allow the next round of deprotection and coupling. The process is repeated until the probes reach their full length, usually 25 nucleotides. However, probes having other lengths such as those set forth elsewhere herein can also be attached at each feature. Once the synthesis is complete, the wafers can be deprotected, diced, and the resulting individual arrays can be packaged in flowcell cartridges.

A spotted array can also be used in a method of the invention. An exemplary spotted array is a CodeLink™ Array available from Amersham Biosciences. CodeLink™ Activated Slides are coated with a long-chain, hydrophilic polymer containing amine-reactive groups. This polymer is covalently crosslinked to itself and to the surface of the slide. Probe attachment can be accomplished through covalent interaction between the amine-modified 5' end of the oligonucleotide probe and the amine reactive groups present in the polymer. Probes can be attached at discrete locations using spotting pens. Useful pens are stainless steel capillary pens that are individually spring-loaded. Pen load volumes can be less than about 200 nL with a delivery volume of about 0.1 nL or less. Such pens can be used to create features having a spot diameter of, for example, about 140-160 µm. In a preferred embodiment, nucleic acid probes at each spotted feature can be 30 nucleotides long. However, probes having other lengths such as those set forth elsewhere herein can also be attached at each spot.

An array that is useful in the invention can also be manufactured using inkjet printing methods such as SurePrint™ Technology available from Agilent Technologies. Such methods can be used to synthesize oligonucleotide probes in situ or to attach pre-synthesized probes having moieties that are reactive with a substrate surface. A printed microarray can contain 22,575 features on a surface having standard slide dimensions (about 1 inch by 3 inches). Typically, the printed probes are 25 or 60 nucleotides in length. However, probes having other lengths such as those set forth elsewhere herein can also be printed at each location.

For several of the embodiments described herein nucleic acid probes are attached to substrates such that they have a free 3' end for modification by enzymes or other agents. Those skilled in the art will recognize that methods exemplified above in regard to synthesis of nucleic acids in the 3' to 5' direction can be modified to produce nucleic acids having free 3' ends. For example, synthetic methods known in the art for synthesizing nucleic acids in the 5' to 3' direction and having 5' attachments to solid supports can be used in an inkjet printing or photolithographic method. Furthermore, in situ inversion of substrate attached nucleic acids can be carried out such that 3' substrate-attached nucleic acids become attach to the substrate at their 5' end and detached at their 3' end. In situ inversion can be carried out according to methods known in the art such as those described in Kwiatkowski et al., *Nucl. Acids Res.* 27:4710-4714 (1999).

An exemplary high density array is an array of arrays or a composite array having a plurality of individual arrays that is configured to allow processing of multiple samples. Such arrays allow multiplex detection of typable loci. Exemplary composite arrays that can be used in the invention, for example, in multiplex detection formats are described in U.S. Pat. No. 6,429,027 and US 2002/0102578. In particular embodiments, each individual array can be present within each well of a microtiter plate. Thus, depending on the size of the microtiter plate and the size of the individual array, very high numbers of assays can be run simultaneously; for example, using individual arrays of 2,000 and a 96 well microtiter plate, 192,000 assays can be performed in parallel; the same number of arrays in each well of a 384 microtiter plate yields 768,000 simultaneous assays, and in a 1536 microtiter plate gives 3,072,000 assays.

In particular embodiments, nucleic acids useful in detecting typable loci of a genome can be attached to particles that are arrayed or otherwise spatially distinguished. Exemplary particles include microspheres or beads. However, particles used in the invention need not be spherical. Rather particles having other shapes including, but not limited to, disks, plates, chips, slivers or irregular shapes can be used. In addition, particles used in the invention can be porous, thus increasing the surface area available for attachment or assay of probe-fragment hybrids. Particle sizes can range, for example, from nanometers such as about 100 nm beads, to millimeters, such as about 1 mm beads, with particles of intermediate size such as at most about 0.2 micron, 0.5 micron, 5 micron or 200 microns being useful. The composition of the beads can vary depending, for example, on the application of the invention or the method of synthesis. Suitable bead compositions include, but are not limited to, those used in peptide, nucleic acid and organic moiety synthesis, such as plastics, ceramics, glass, polystyrene, methylstyrene, acrylic polymers, paramagnetic materials, thoria sol, carbon graphite, titanium dioxide, latex or cross-linked dextrans such as Sepharose™, cellulose, nylon, cross-linked micelles or Teflon™. Useful particles are described, for example, in *Microsphere Detection Guide* from Bangs Laboratories, Fishers Ind.

Several embodiments of array-based detection in the invention are exemplified below for beads or microspheres. Those skilled in the art will recognize that particles of other shapes and sizes, such as those set forth above, can be used in place of beads or microspheres exemplified for these embodiments.

Each particle used for detection of typable loci in a population of genome fragments can include an associated capture probe. However, if desired, one or more particles can be included in an array or population of particles that do not contain a capture probe. A capture probe can be any molecule or material that directly or indirectly binds a nucleic acid having a target sequence such as a typable locus. A capture probe can be, for example, a nucleic acid that has a sequence that hybridizes to a complementary nucleic acid or another molecule that binds to a nucleic acid in a sequence-specific fashion.

In a particular embodiment, each bead or other array location can have a single type of capture probe. However, a plurality of probes can be attached to each bead if desired. For example, a bead or other array location can have two or more probes that anneal to different portions of the same genome fragment. The probes can anneal to adjacent locations or at locations that are separated from each other on the captured target nucleic acid. Use of this multiple probe capture embodiment can increase specificity of detection compared to the use of only one of the probes. Thus, in cases where smaller probes are desired a multiple probe strategy can be employed to provide specificity comparable to embodiments where longer probes are utilized. Similarly, a subpopulation of more than one microsphere containing a particular capture probe can be used to detect typable loci of a genome in the invention. Thus, redundancy can be built into the assay system by the use of subpopulations of microspheres for particular probes.

In some embodiments, polymer probes such as nucleic acids or peptides can be synthesized by sequential addition of monomer units directly on a solid support used in an array such as a bead or slide surface. Methods known in the art for synthesis of a variety of different chemical compounds on solid supports can be used in the invention, such as methods for solid phase synthesis of peptides, organic moieties, and nucleic acids. Alternatively probes can be synthesized first, and then covalently attached to a solid support. Probes can be attached to functional groups on a solid support. Functionalized solid supports can be produced by methods known in the art and, if desired, obtained from any of several commercial suppliers for beads and other supports having surface chemistries that facilitate the attachment of a desired functionality by a user. Exemplary surface chemistries that are useful in the invention include, but are not limited to, amino groups such as aliphatic and aromatic amines, carboxylic acids, aldehydes, amides, chloromethyl groups, hydrazide, hydroxyl groups, sulfonates or sulfates. If desired, a probe can be attached to a solid support via a chemical linker. Such a linker can have characteristics that provide, for example, stable attachment, reversible attachment, sufficient flexibility to allow desired interaction with a genome fragment having a typable locus to be detected, or to avoid undesirable binding reactions. Further exemplary methods that can be used in the invention to attach polymer probes to a solid support are described in Pease et al., *Proc. Natl. Acad. Sci. USA* 91(11):5022-5026 (1994); Khrapko et al., *Mol Biol (Mosk) (USSR)* 25:718-730 (1991); Stimpson et al., *Proc. Natl. Acad. Sci. USA* 92:6379-6383 (1995) or Guo et al., *Nucleic Acids Res.* 22:5456-5465 (1994).

Generally, an array of arrays can be configured in any of several ways. In a particular embodiment, as is more fully described below, a one component system can be used. That is, a first substrate having a plurality of assay locations, such as a microtiter plate, can be configured such that each assay location contains an individual array. Thus, the assay location and the array location can be the same. For example, the plastic material of a microtiter plate can be formed to contain a plurality of bead wells in the bottom of each of the assay wells. Beads containing the capture probes of the invention can then be loaded into the bead wells in each assay location as is more fully described below.

Alternatively, a two component system can be used. In this embodiment, individual arrays can be formed on a second substrate, which then can be fitted or dipped into the first microtiter plate substrate. A particular embodiment utilizes fiber optic bundles as individual arrays, generally with bead wells etched into one surface of each individual fiber, such that the beads containing the capture probes are loaded onto the end of the fiber optic bundle. The composite array thus includes a number of individual arrays that are configured to fit within the wells of a microtiter plate.

Accordingly, the present invention provides a composite array having at least a first substrate with a surface having a plurality of assay locations. Any of a variety of arrays having a plurality of candidate agents in an array format can be used in the invention. The size of an array used in the invention can vary depending on the probe composition and desired use of the array. Arrays containing from about 2 different probes to many millions can be made, with very large fiber optic arrays being possible. Generally, an array can have from two to as many as a billion or more array locations per square cm. An array location can be, for example, an area on a surface to which a probe or population of similar probes are attached or a particle. In the case of a particle, its array location can be a fixed coordinate on a substrate to which it is attached or associated, or a relative coordinate compared to locations of one or more other reference particles in a fluid sample such as a stream passing through a flow cytometer. Very high density arrays are useful in the invention including, for example, those having from about 10,000,000 array locations/cm$^2$ to about 2,000,000,000 array locations/cm$^2$ or from about 100,000,000 array locations/cm$^2$ to about 1,000,000,000 array locations/Cm$^2$. High density arrays can also be used including, for example, those in the range from about 100,000 array locations/cm$^2$ to about 10,000,000 array locations/cm$^2$ or about 1,000,000 array locations/cm$^2$ to about 5,000,000 array locations/cm$^2$. Moderate density arrays useful in the invention can range from about 10,000 array locations/cm$^2$ to about 100,000 array locations/cm$^2$, or from about 20,000 array locations/cm$^2$ to about 50,000 array locations/cm$^2$. Low density arrays are generally less than 10,000 particles/cm$^2$ with from about 1,000 array locations/cm$^2$ to about 5,000 array locations/cm$^2$ being useful in particular embodiments. Very low density arrays having less than 1,000 array locations/cm$^2$, from about 10 array locations/cm$^2$ to about 1000 array locations/cm$^2$, or from about 100 array locations/cm$^2$ to about 500 array locations/cm$^2$ are also useful in some applications. The methods of the invention need not be performed in array format, for example, in embodiments in which one or a small number of loci are to be detected. If desired, arrays having multiple substrates can be used, including, for example substrates having different or identical compositions. Thus for example, large arrays can include a plurality of smaller substrates.

For some applications the number of individual arrays is set by the size of the microtiter plate used; thus, 96 well, 384 well and 1536 well microtiter plates utilize composite arrays comprising 96, 384 and 1536 individual arrays. As will be appreciated by those in the art, each microtiter well need not contain an individual array. It should be noted that composite arrays can include individual arrays that are identical, similar or different. For example, a composite array having 96 similar arrays can be used in applications where it is desired to determine the presence or absence of the same 2,000 typable loci for 96 different samples. Alternatively, a composite array having 96 different arrays, each with 2,000 different probes, can be used in applications where it is desired to determine the presence or absence of 192,000 typable loci for a single sample. Alternative combinations, where rows, columns or other portions of a microtiter formatted array are the same can be used, for example, in cases where redundancy is desired. As will be appreciated by those in the art, there are a variety of ways to configure the system. In addition, the random nature of the arrays can mean that the same population of beads can be added to two different surfaces, resulting in substantially similar but perhaps not identical arrays.

A substrate used in an array of the invention can be made from any material that can be modified to contain discrete individual sites and is amenable to at least one detection method. In embodiments where arrays of particles are used a material that is capable of attaching or associating with one or more type of particles can be used. Useful substrates include, but are not limited to, glass; modified glass; functionalized glass; plastics such as acrylics, polystyrene and copolymers of styrene and other materials, polypropylene, polyethylene, polybutylene, polyurethanes, Teflon, or the like; polysaccharides; nylon; nitrocellulose; resins; silica; silica-based materials such as silicon or modified silicon; carbon; metal; inorganic glass; optical fiber bundles, or any of a variety of other polymers. Useful substrates include those that allow optical detection, for example, by being translucent to energy of a desired detection wavelength and/or do not themselves appreciably fluoresce in a desired detection wavelength.

Generally a substrate used for an array of the invention has a flat or planar surface. However, other configurations of substrates can be used as well. For example, three dimensional configurations can be used by embedding an array, such as a bead array in a porous material, such as a block of plastic, that allows sample access to the array locations and use of a confocal microscope for detection. Similarly, assay locations can be placed on the inside surface of a tube, for flow-through sample analysis. Exemplary substrates that are useful in the invention include, but are not limited to, optical fiber bundles, or flat planar substrates such as glass, polystyrene or other plastics and acrylics.

The surface of a substrate can include a plurality of individual array locations that are physically separated from each other. For example, physical separation can be due to the presence of assay wells, such as in a microtiter plate. Other barriers that can be used to physically separate array locations include, for example, hydrophobic regions that will deter flow of aqueous solvents or hydrophilic regions that will deter flow of apolar or hydrophobic solvents.

Array locations that are physically separated from each other form assay locations. An assay location can include an array of probes and provide a vessel for holding a fluid such that the fluid contacts the probes. For example, a fluid containing genome fragments can be contacted with probes under hybridization conditions set forth herein or known in the art. Similarly, a wash fluid or fluid containing other reagents or analytes described herein can be contacted with an array of probes when placed in an assay location. An assay location can be enclosed, if desired. Exemplary enclosures include, without limitation, a cassette, enclosed well, or a slide surface enclosed by a gasket or membrane or both. Further exemplary enclosures that are useful in the invention are described in WO 02/00336, US Pat. App. Pub. 02/0102578 or the references cited previously herein in regard to different types of arrays.

An assay location can also be the interior of a flow cell. An array of probes can be placed at an interior surface of the flow cell and a fluid introduced by flowing into the cell. A flow cell useful in the invention can be a capillary gap flow cell. A capillary gap flow cell has a sufficiently narrow interior dimension and openings such that a fluid can be retained in the cell by capillary action and subsequently displaced by positive pressure exerted at an opening by a second fluid. Positive pressure can be provided, for example, by gravity flow. An exemplary capillary flow cell that is useful in the invention is one formed between the surface of a slide-based array such as a BeadChip array (Illumina, Inc., San Diego Calif.) and a Coverplate (ThermoShandon, Inc., Pittsburgh, Pa.). Another useful capillary gap flow cell is that used in the GenePaint™ flow through system available from Tecan (Maennedorf, Switzerland). Accordingly, the invention provides a method of enzymatic modification of nucleic acids, such as substrate attached probes, in a capillary gap flow cell. Those skilled in the art will recognize that a capillary flow cell can be formed with any of a variety of arrays known in the art to achieve similar fluid flow capabilities.

The sites can be a pattern such as a regular design or configuration, or the sites can be in a non-patterned distribution. A non-limiting advantage of a regular pattern of sites is that the sites can be conveniently addressed in an X-Y coordinate plane. A pattern in this sense includes a repeating unit cell, such as one that allows a high density of beads on a substrate.

In a particular embodiment, an array substrate can be an optical fiber bundle or array, as is generally described in U.S. Ser. No. 08/944,850, U.S. Pat. No. 6,200,737; WO9840726, and WO9850782. Also useful in the invention is a preformed unitary fiber optic array having discrete individual fiber optic strands that are co-axially disposed and joined along their lengths. A distinguishing feature of a preformed unitary fiber optic array compared to other fiber optic formats is that the fibers are not individually physically manipulable; that is, one strand generally cannot be physically separated at any point along its length from another fiber strand.

The sites of an array of the invention need not be discrete sites. For example, it is possible to use a uniform surface of adhesive or chemical functionalities, for example, that allows the attachment of particles at any position. That is, the surface of an array substrate can be modified to allow attachment or association of microspheres at individual sites, whether or not those sites are contiguous or non-contiguous with other sites. Thus, the surface of a substrate can be modified to form discrete sites such that only a single bead is associated with the site or, alternatively, the surface can be modified such that beads end up randomly populating sites in various numbers.

In a particular embodiment, the surface of the substrate can be modified to contain wells, or depressions in the surface of the substrate. This can be done using a variety of techniques, including, but not limited to, photolithography, stamping techniques, molding techniques or microetching techniques. As will be appreciated by those in the art, the technique used will depend on the composition and shape of the substrate. When the substrate for a composite array is a microtiter plate, a molding technique can be utilized to form bead wells in the bottom of the assay wells.

In a particular embodiment, physical alterations can be made in a surface of a substrate to produce array locations. For example, when the substrate is a fiber optic bundle, the surface of the substrate can be a terminal end of the fiber bundle, as is generally described in U.S. Pat. Nos. 6,023,540 and 6,327,410. In this embodiment, wells can be made in a terminal or distal end of a fiber optic bundle having several individual fibers. In this embodiment, the cores of the individual fibers can be etched, with respect to the cladding, such that small wells or depressions are formed at one end of the fibers. The depth of the wells can be altered using different etching conditions to accommodate particles of a particular size or shape. Generally in this embodiment, the microspheres are non-covalently associated in the wells, although the wells can additionally be chemically functionalized for covalent binding of particles. As set forth below in further detail, cross-linking agents can be used, or a physical barrier can be used such as a film or membrane over the particles.

In a particular embodiment, the surface of a substrate can be modified to contain chemically modified sites that are useful for attaching, either-covalently or non-covalently, probes or particles having attached probes. Chemically modified sites in this context include, but are not limited to, the addition of a pattern of chemical functional groups including, for example, amino groups, carboxy groups, oxo groups or thiol groups. Such groups can be used to covalently attach probes or particles that contain corresponding reactive functional groups. Other useful surface modifications include, for example, the addition of a pattern of adhesive that can be used to bind particles; the addition of a pattern of charged groups for the electrostatic attachment of probes or particles; the addition of a pattern of chemical functional groups that render the sites differentially hydrophobic or hydrophilic, such that the addition of similarly hydrophobic or hydrophilic probes or particles under suitable conditions will result in association to the sites on the basis of hydroaffinity.

Once microspheres are generated, they can be added to a substrate to form an array. Arrays can be made, for example, by adding a solution or slurry of the beads to a substrate containing attachment sites for the beads. A carrier solution for the beads can be a pH buffer, aqueous solvent, organic solvent, or mixture. Following, exposure of a bead slurry to a substrate, the solvent can be evaporated, and excess beads removed. In embodiments wherein non-covalent methods are used to associate beads to an array substrate, beads can be loaded onto the substrate by exposing the substrate to a solution of particles and then applying energy, for example, by agitating or vibrating the mixture. However, static loading can also be used if desired. Methods for loading beads and other particles onto array substrates that can be used in the invention are described, for example, in U.S. Pat. No. 6,355,431. Bead loading can be carried out prior to modification of probes in a detection method set forth herein. Alternatively, bead loading can be carried out after modification of bead immobilized probes that are hybridized with genome fragments in a method of the invention.

In some embodiments, for example when chemical attachment is done, probes or particles with associated probes can be attached to a substrate in a non-random or ordered process. For example, using photoactivatible attachment linkers or photoactivatible adhesives or masks, selected sites on an array substrate can be sequentially activated for attachment, such that defined populations of probes or particles are laid down at defined positions when exposed to the activated array substrate.

Alternatively, probes or particles with associated probes can be randomly deposited on a substrate and their positions in the array determined by a decoding step. This can be done before, during or after the use of the array to detect typable loci using methods such as those set forth herein. In embodiments where the placement of probes is random, a coding or decoding system can be used to localize and/or identify the probes at each location in the array. This can be done in any of a variety of ways, as is described, for example, in U.S. Pat. No. 6,355,431.

In embodiments where particles are used, unique optical signatures can be incorporated into the particles and can be used to identify the chemical functionality or nucleic acid associated with the particle. Exemplary optical signatures include, without limitation, dyes, usually chromophores or fluorophores, entrapped or attached to the beads. Different types of dyes, different ratios of mixtures of dyes, or different concentrations of dyes, or a combination of these differences can be used as optical signatures in the invention. Further examples of particles and other supports having detectable signatures that can be used in the invention are described in Cunin et al., *Nature Materials* 1:39-41 (2002); U.S. Pat. Nos. 6,023,540 or 6,327,410; or WO9840726. In accordance with this embodiment, the synthesis of the nucleic acids can be divorced from their placement on an array. Thus, capture probes can be synthesized on beads, and then the beads can be randomly distributed on a patterned surface. Since the beads are first coded with an optical signature, this means that the array can later be decoded. Thus, after an array is made, a correlation of the location of an individual array location on the array with its probe identity can be made. This means that the array locations can be randomly distributed on the array, a fast and inexpensive process in many applications of the invention as compared to either in situ synthesis or spotting techniques that are generally outlined in U.S. Ser. Nos. 98/05, 025, 99/14,387, 08/818,199 or 09/151,877. However, if desired, arrays made by in situ synthesis or spotting techniques can be used in the invention.

It should be noted that not all sites of an array need to include a probe or particle. Thus, an array can have one or more array locations on the substrate that are empty. In some embodiments, an array substrate can include one or more sites that contain more than one bead or probe.

As will be appreciated by those in the art, a random array need not necessarily be decoded. In this embodiment, beads or probes can be attached to an array substrate, and a detection assay performed. Array locations that have a positive signal for presence of a probe-fragment hybrid with a particular typable locus can be marked or otherwise identified to distinguish or separate them from other array locations. For example, in applications where beads are labeled with a fluorescent dye, array locations for positive or negative beads can be marked by photobleaching. Further exemplary marks include, but are not limited to, non-fluorescent precursors that are converted to fluorescent form by light activation or photocrosslinking groups which can derivatize a probe or particle with a label or substrate upon irradiation with light of an appropriate wavelength.

In a particular embodiment, several levels of redundancy can be built into an array used in the invention. Building redundancy into an array can give several non-limiting advantages, including the ability to make quantitative estimates of confidence about the data and substantial increases in sensitivity. As will be appreciated by those in the art, there are at least two types of redundancy that can be built into an array: the use of multiple identical probes or the use of multiple probes directed to the same target, but having different chemical functionalities. For example, for the detection of nucleic acids, sensor redundancy utilizes a plurality of sensor elements such as beads having identical binding ligands such as probes. Target redundancy utilizes sensor elements with different probes to the same target: one probe can span the first 25 bases of a target, a second probe can span the second 25 bases of the target, etc. By building in either or both of these types of redundancy into an array a variety of statistical mathematical analyses can be done for analysis of large data sets. Other methods for decoding with redundant sensor elements and target elements that can be used in the invention are described, for example, in U.S. Pat. No. 6,355,431.

Typable loci of probe-fragment hybrids can be detected on an array using the methods set forth previously herein. In a particular embodiment, probe redundancy can be used. In this embodiment, a plurality of probes having identical sequences is present in an array. Thus, a plurality of subpopulations each having a plurality of beads with identical probes can be present in the array. By using several identical probes for a given array, the optical signal from each array location can be combined and analyzed using statistical methods. Thus, redundancy can significantly increase the confidence of the data where desired.

As will be appreciated by those in the art, the number of identical probes in a sub-population will vary with the application and use of a particular array. In general, anywhere from 2 to thousand of identical array locations can be used, including, for example, about 5, 10, 20, 50 or 100 identical probes or particles.

Once obtained, signals indicative of probe-fragment hybrids from a plurality of array locations can be manipulated and analyzed in a variety of ways, including baseline adjustment, averaging, standard deviation analysis, distribution and cluster analysis, confidence interval analysis, mean testing, or the like. Further description of the data manipulations is set forth below and in many cases is exemplified for probe-fragment hybrids detected on a bead array. Those skilled in the art will recognize that similar manipulations can be carried out for other populations of probe-fragment hybrids including, for example, those in which other array locations are treated similarly to the beads in the examples below.

Optionally, a plurality of signals detected from an array or other mixture of probe-fragment hybrids can be baseline adjusted. In an exemplary procedure, optical signals can be adjusted to start at a value of 0.0 by subtracting the integer 1.0 from all data points. Doing this allows the baseline-loop data to remain at zero even when summed together and random response signal noise is canceled out. When the sample is a fluid, the fluid pulse-loop temporal region, however, frequently exhibits a characteristic change in response, either positive, negative or neutral, prior to the sample pulse and often requires a baseline adjustment to overcome noise associated with drift in the first few data points due to charge buildup in the CCD camera. If no drift is present, typically the baseline from the first data point for each bead can be subtracted from all the response data for the same bead type. If drift is observed, the average baseline from the first ten data points for each bead can be subtracted from all the response data for the same bead type. By applying this baseline adjustment, when multiple array location responses are added together they can be amplified while the baseline remains at zero. Since all array locations respond at the same time to the sample (e.g. the sample pulse), they all see the pulse at the exact same time and there is no registering or adjusting needed for overlaying their responses. In addition, other types of baseline adjustment that are known in the art can be performed, depending on the requirements and output of the system used.

Any of a variety of possible statistical analyses can be run to generate known statistical parameters. Analyses based on redundancy are known and generally described in texts such as Freund and Walpole, *Mathematical Statistics*, Prentice Hall Inc., New Jersey (1980).

If desired, signal summing can be done by adding the intensity values of all responses at a particular time point. In a particular embodiment, signals can be summed at several timepoints, thereby generating a temporal response comprised of the sum of all bead responses. These values can be baseline-adjusted or raw. Signal summing can be performed in real time or during post-data acquisition data reduction and analysis. In one embodiment, signal summing can be performed with a commercial spreadsheet program (Excel, Microsoft, Redmond, Wash.) after optical response data is collected. Further exemplary signal summing methods that can be used in the invention are described in U.S. Pat. No. 6,355,431.

In a particular embodiment, statistical analyses can be done to evaluate whether a particular data point has statistical validity within a subpopulation by using techniques including, but not limited to, distribution or cluster analysis. This can be done to statistically discard outliers that can otherwise skew the result and increase the signal-to-noise ratio of any particular experiment. Useful methods for determining whether data points have statistical validity are described, for example, in U.S. Pat. No. 6,355,431 and include, but are not limited to, the use of confidence intervals, mean testing, or distribution analysis.

A particular embodiment utilizes a plurality of nucleic acid probes that are directed to a single typable locus but differ in their actual sequence. For example, a single target genome fragment can have two or more array locations each having a different probe. This can add a level of confidence in applications where non-specific binding interactions occur with particular sequences. Accordingly, redundant nucleic acid probes can have sequences that are overlapping, adjacent, or spatially separated.

A method of the invention can further include a step of contacting an array of nucleic acid probes with chaperone probes. Chaperone probes are nucleic acids that hybridize to a target genome fragment at a site that is proximal to the hybridization site for a probe used to detect or capture the genome fragment. Chaperone probes can be added before or during a capture step or detection step in order to favor hybridization of capture probes or detection probes to the genome fragment. Chaperone probes can favor hybridization of detection or capture probes by preventing association of the complementary strands of a genome fragment such that the appropriate template strand is available for annealing to the detection or capture probes.

Chaperone probes can have any of a variety of lengths or compositions including, for example, those set forth previously herein for other nucleic acids useful in the invention. A chaperone probe can hybridize to a target sequence immediately adjacent to an annealing site for another probe or at a site that is separated from the annealing site for the other probe. The gap between probes can be 1 or more, 2 or more, 3 or more, 5 or more, 10 or more nucleotides in length or longer. Chaperone probes can be provided in any stoichiometric concentration that is found to effectively favor annealing of another probe including, for example, a ratio of about 100 moles, 10 moles, 5 moles, 2 moles, 1 mole, 0.5 mole, or 0.1 mole of chaperone probe per mole of target genome fragment.

A method of the invention can further include a step of signal amplification in which the number of detectable labels attached to a nucleic acid is increased. In one embodiment, a signal amplification step can include providing a nucleic acid that is labeled with a ligand having affinity for a particular receptor. A first receptor having one or more sites capable of binding the ligand can be contacted with the labeled nucleic acid under conditions where a complex forms between the receptor and ligand-labeled nucleic acid. Furthermore, the receptor can be contacted with an amplification reagent that has affinity for the receptor. The amplification reagent can be, for example, the ligand, a mimetic of the ligand, or a second receptor having affinity for the first receptor. The amplification reagent can in turn be labeled with the ligand such that a multimeric complex can form between the ligand receptor and amplification reagent. The presence of the multimeric complex can then be detected, for example, by detecting the presence of a detectable label on the receptor or the amplification reagent. The components included in a signal amplification step can be added in any order so long as a detectable complex is formed. Furthermore, other binding moieties and binding partner pairs such as those set forth herein previously can be used for signal amplification.

Figure 10:
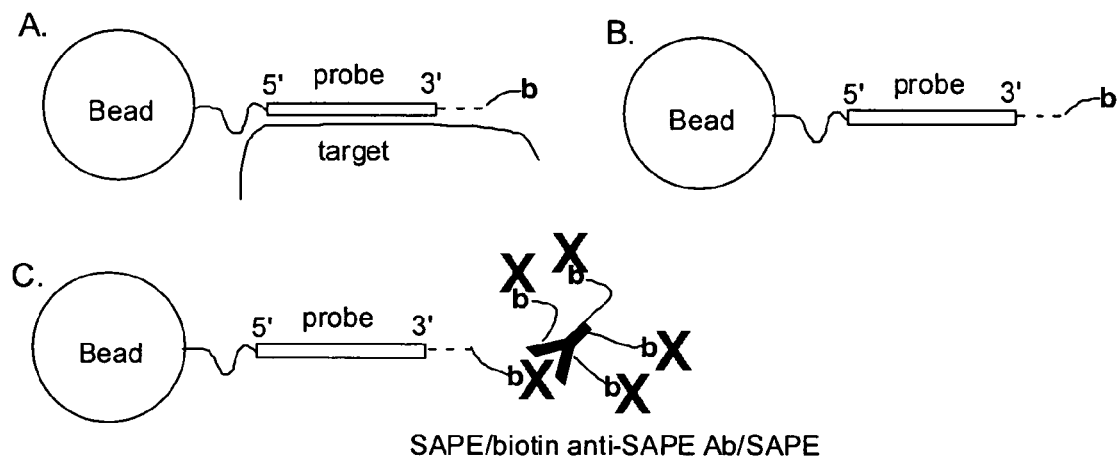
FIG. 10 shows an exemplary signal amplification scheme.

As shown in the exemplary signal amplification scheme of FIG. 10, signal amplification can be carried out using a nucleic acid labeled by streptavidin-phycoerythrin (SAPE) and a biotinylated anti-SAPE antibody. In one embodiment, a three step protocol can be employed in which arrayed probes that have been modified to incorporate biotin are first incubated with streptavidin-phycoerythrin (SAPE), followed by incubation with a biotinylated anti-streptavidin antibody, and finally incubation with SAPE again. This process creates a cascading amplification sandwich since streptavidin has multiple antibody binding sites and the antibody has multiple biotins. Those skilled in the art will recognize from the teaching herein that other receptors such as avidin, modified versions of avidin, or antibodies can be used in an amplification complex and that different labels can be used such as Cy3, Cy5 or others set forth previously herein. Further exemplary signal amplification techniques and components that can be used in the invention are described, for example, in U.S. Pat. No. 6,203,989 B1.

A method of the invention can further include a step of removing genome fragments from probe-fragment hybrids following modification of the probes and prior to detection of the modified probes. Genome fragments can be removed by denaturing fragment-probe hybrids using methods known in the art for disrupting base-pairing interactions such as exposure to low salt, organic solvents such as formamide, heat or other denaturing agents. Exemplary methods for denaturing hybrid nucleic acids that are useful in the methods are described in Sambrook et al., supra (2001) or in Ausubel et al., supra, (1998). Genome fragments can be washed away following denaturation. Alternatively, genome fragments can be present under denaturing conditions during detection.

A method of the invention can further include a step of producing a report identifying at least one typable locus that is detected. A detected typable locus can be directly identified for example, by sequence, location on a chromosome or by a recognized name of the locus. Alternatively, the report can include data obtained from a method of the invention in a format that can be subsequently analyzed to identify one or more detected loci.

Thus, the invention further provides a report of at least one result obtained by a method of the invention. A report of the invention can be in any of a variety of recognizable formats including, for example, an electronic transmission, computer readable memory, an output to a computer graphical user interface, compact disk, magnetic disk or paper. Other formats suitable for communication between humans, machines or both can be used for a report of the invention.

The invention further provides an array including a solid-phase immobilized representative population of genome fragments. A representative population of genome fragments can be produced and immobilized using methods such as those set forth herein previously. For example, a genome can be amplified using primers having a secondary label such as biotin or reactive crosslinking groups and subsequently immobilized via interaction with a solid phase receptor such as avidin or a chemical moiety reactive with the crosslinking group. A solid-phase immobilized representative population of genome fragments can have one or more of the characteristics set forth previously herein such as high, low or medium complexity.

A solid-phase immobilized representative population of genome fragments can be directly interrogated using the methods of the invention. Generally, detection assays and methods have been exemplified above with respect to immobilized probes and soluble genome fragment targets. Those skilled in the art will recognize that in embodiments wherein a representative population of genome fragments is immobilized the methods can be similarly performed, however, with the genome fragments replacing the probes in the above examples and the probes treated as targets in the above examples.

Employing a solid phase genomic DNA target can provide the advantage of a high degree of assay multiplexing by allowing any poorly hybridized or excess detection primers to be washed away before subsequent enzymatic modification of the primers, for example, in an extension or ligation technique. Applications that are adversely affected by primer-dimer formation can be improved by removing primer dimers before detection. A solid-phase target DNA format can also allow fast hybridization kinetics since the primers can be hybridized at a relatively high concentrations, for example, greater than about 100 pM.

The methods set forth herein for amplifying genomic DNA allow relatively small amounts of genomic DNA to be amplified to a large amount. Immobilization of large amounts of genomic DNA to a solid-phase can allow typable loci to be queried directly, for example, in a primer extension or ligation-based assay without the need for subsequent amplification. Elimination of amplification can lead to more robust and quantitative genotyping than is often available when pre-amplification-based detection is used.

Another advantage of using a solid phase genomic DNA target is that it can be reused. Thus, the immobilized genome target can be an archival sample that can be used repeatedly with different sets of nucleic acid probes. Furthermore, in some applications carry-over contamination can be reduced by using immobilized gDNA since the amplification occurs before the SNP specific detection reaction. It will be understood that, the steps described above for carrying out methods of the invention have been set forth in a particular order for the sake of explanation. Those skilled in the art will recognize that the steps can be carried out in any of a variety of orders so long as a desired result is achieved. For example, components of the reactions set forth above can be added simultaneously, or sequentially, in any order that are effective at producing one or more of the results described. In addition, the reactions set forth herein can include a variety of other reagents including, for example, salts, buffers, neutral proteins, albumin, detergents, or the like. Such reagents can be added to facilitate optimal hybridization and detection, reduce non-specific or background interactions, or to stabilize other reagents used. Also reagents that otherwise improve the efficiency of a method of the invention, such as protease inhibitors, nuclease inhibitors, anti-microbial agents, or the like can be used, depending on the sample preparation methods and purity of the target. Those skilled in the art will know or be able to determine appropriate reagents to achieve such results.

Several of the methods exemplified herein with respect to detection of typable loci of genomic DNA can also be applied to gene expression analysis. In particular, methods for on-array labeling of probe nucleic acids using primer extension methods can be used in the detection of RNA or cDNA. Probe-cDNA hybrids can be detected by polymerase-based primer extension methods as described herein previously. Alternatively, for array-hybridized mRNA, reverse-transcriptase-based primer extension can be employed. There are several non-limiting advantages of on-array labeling for gene expression analysis. Labeling costs can be dramatically decreased since the amounts of labeled nucleotides employed are substantially less compared to methods for labeling captured targets. Secondly, cross-hybridization can be dramatically reduced since a target must both hybridize and also contain perfect complementarity at its 3'terminus for label incorporation in a primer extension reaction. Similarly, OLA or GOLDENGATE® assays can be used for detection of hybridized cDNA or mRNA. The latter two methods typically require addition of an exogenous nucleic acid for each locus queried. However, such methods can be advantageous in applications where the use of primer extension leads to unacceptable levels of ectopic extension.

The above described on-array labeling with primer extension can also be used to monitor alternate splice sites by designing the 3' probe terminus to coincide with a splice junction of a target cDNA or mRNA. The terminus can be placed to uniquely identify all the relevant possible acceptor splice sites for a particular gene. For example, the first 45 bases can be chosen to lie entirely within the donor exon, and the last 5 3'-bases can lie in a set of possible splice acceptor exons that become spliced adjacent to the first 45 bases.

A cDNA or mRNA target can be used in place of gDNA in a method described previously herein for identifying typable loci. For example, a cDNA or mRNA target can be used in a genotyping assay. Genotyping cDNA or mRNA can allow allelic-specific expression differences to be monitored, for example, via "quantitative genotyping", or measuring the proportion of one allele vs. the other allelic at a biallelic SNP marker. Allelic expression differences can result, for example, from changes in transcription rate, transcript processing or transcript stability. Such an effect can result from a polymorphism (or mutation) in a regulatory region, promoter, splice site or splice site modifier region or other such regions. In addition, epigenomic changes in the chromatin such as methylation can also contribute to allelic expression differences. Thus, the methods can be used to detect such polymorphisms or mutations in expressed products.

A "normalized" representation can be created from a cDNA or mRNA target by any of several methods such as those based upon placing universal PCR tails on a cDNA representation (see, for example, Brady, *Yeast,* 17:211-7 (2000)) The normalization process can be used to generate a cDNA representation wherein each typable locus in the population is present at relatively the same copy number. This can aid in the quantitative genotyping process of a cDNA sample since the signal intensities from the array-based primer extension assay will be more uniform than without the normalization process.

In a further embodiment, a method of the invention can be used to characterize an mRNA or cDNA sample. An mRNA or cDNA sample can be used as a target sample in a method of the invention and a representative set of typable loci detected. The representative set of typable loci can be selected to be diagnostic or characteristics of the mRNA or cDNA sample. For example, the levels of particular typable loci can be detected in a sample and compared to reference levels for these loci, the reference levels being indicative of the extent to which the sample includes expressed sequences covering desired genes. Thus, the methods can be used to determine the quality of an mRNA or cDNA sample or its appropriateness for a particular application.

A typical array location, such as a bead, can contain a large population of relatively densely packed probe nucleic acids. Following hybridization of target nucleic acids under many conditions only a portion of probes in a detection assay will be occupied with a complementary target. Under such conditions it is possible that densely packed probes will form inter-probe structures that are susceptible to ectopic primer extension. Furthermore, as shown in FIG. 13A probes having self complementary sequences can also structures that are susceptible to ectopic primer extension. Ectopic extension refers to modification of one or both probes in an inter- or intra-probe hybrid during an extension reaction. Ectopic extension can occur irregardless of the presence of a hybridized target to the array.

Accordingly, the invention provides a method for inhibiting ectopic extension of probes in a primer extension assay. The method includes the steps of (a) contacting a plurality of probe nucleic acids with a plurality of target nucleic acids under conditions wherein probe-target hybrids are formed; (b) contacting the plurality of probe nucleic acids with an ectopic extension inhibitor under conditions wherein probe-ectopic extension inhibitor hybrids are formed; and (c) selectively modifying probes in the probe-target hybrids compared to probes in the probe-ectopic extension inhibitor hybrids.

Figure 13:
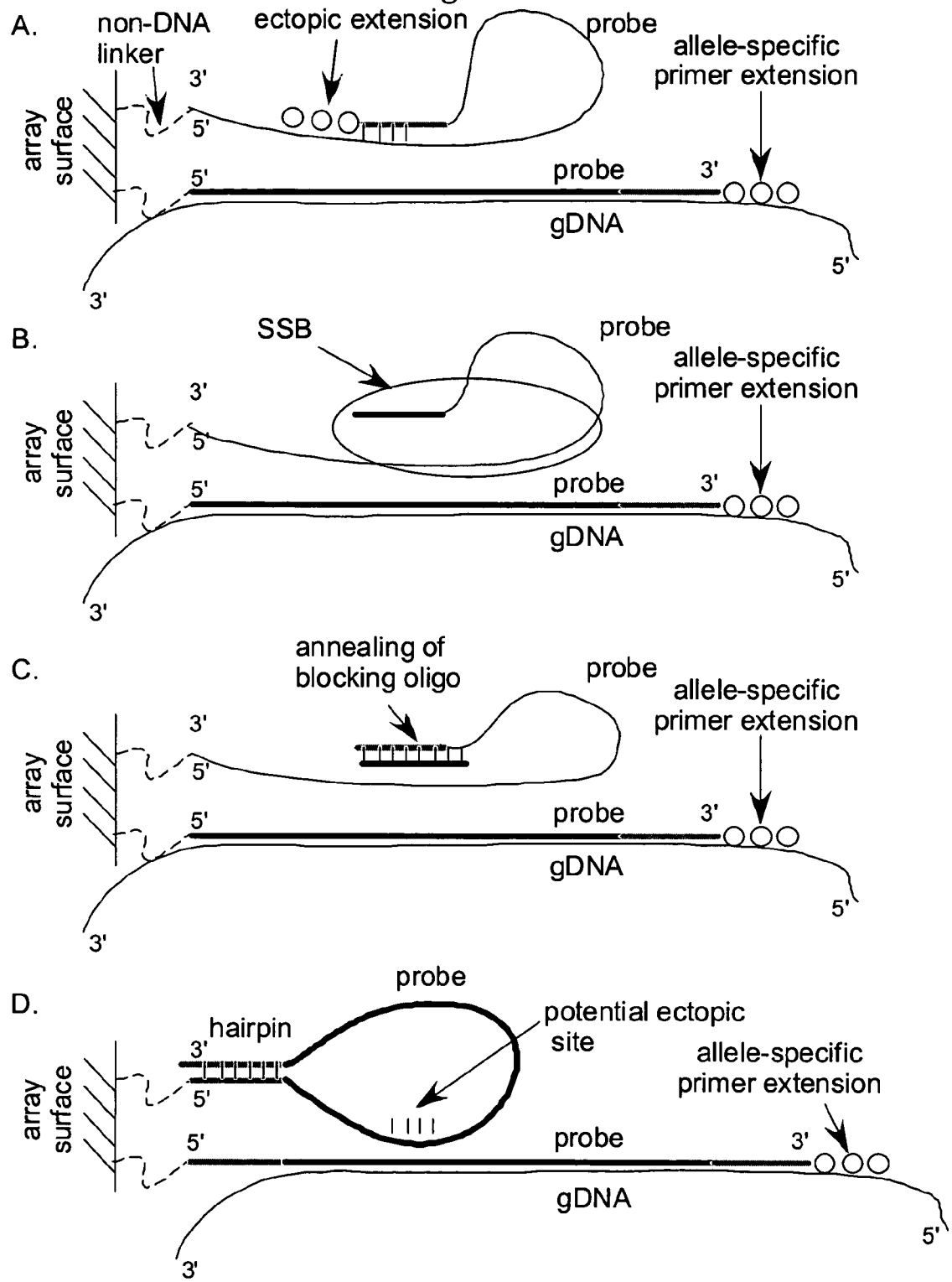
FIG. 13 shows diagrams illustrating ectopic extension (Panel A) and methods for inhibiting ectopic extension including inhibition by binding single-stranded probes to SSB (Panel B); blocking the 3' end of the probes with nucleic acids having complementary sequences (Panel C); and formation of unextendable hairpins (Panel D).

An ectopic extension inhibitor useful in the invention can be any agent that is capable of binding to a single stranded nucleic acid probe, thereby preventing hybridization of the probe to a second probe. Exemplary agents include, but are not limited to single stranded nucleic acid binding proteins (SSBs), nucleic acids such as those set forth above including nucleic acid analogs, small molecules. Such agents have the general property of preferentially binding to single-stranded nucleic acids over double-stranded nucleic acids irrespective of the nucleotide sequence. Exemplary single-stranded nucleic acid binding proteins that can be used in the invention include, but are not limited to, Eco SSB, T4 gp32, T7 SSB, N4 SSB, Ad SSB, UP1, and the like and others described, for example, in Chase et al, *Ann. Rev. Biochem.*, 55: 103-36 (1986); Coleman et al, *CRC Critical Reviews in Biochemistry*, 7(3): 247-289 (1980) and U.S. Pat. No. 5,773,257. Ectopic extension in any of the primer extension assays set forth above can be inhibited using a method of the invention. Exemplary embodiments of the methods for inhibiting ectopic extension of probes in a primer extension assay are shown in FIG. 13 and described in further detail below.

As shown in FIG. 13B, ectopic extension can be minimized by incubating a population of probes with a protein or other agent that selectively binds single stranded nucleic acids, such as SSB, T4 gene 32 or the like. The agent or protein can be added under conditions where it coats the single strand probes that have not hybridized to a target nucleic acid thereby preventing their self-annealing and subsequent extension. An agent such as a protein that binds to single stranded probes can be added to a population of probes prior to or during a primer extension reaction, for example, prior to or during an annealing step.

Ectopic expression can also be reduced using one or more blocking oligonucleotides (oligos). As shown in FIG. 13C, a blocking oligo that is complementary to the 3' end of a probe can be added under conditions where it will hybridize to probes that have not hybridized to a target nucleic acid. In applications where several probes are present, a plurality of blocking oligonucleotides designed to anneal to the 3' ends of the probes can be added. One or more blocking oligos can be added to a population of probes prior to or during a primer extension reaction, for example, prior to or during an annealing step.

As shown in FIG. 13D, a probe can be designed with complementary sequence portions capable of forming a hairpin structure that is not capable of being extended under the conditions used for the primer extension step in a primer extension assay. In the example shown in FIG. 13D, the 3' end of the probe anneals to the 5' end of the probe, and because the 5' end is not adjacent to a readable template the hairpin cannot be ectopically extended. A probe can be designed to have a first sequence region adjacent to the 3' end of the probe that is complementary to a second sequence region of the probe such that a hairpin forms with a 3' overhang that is not capable of being extended. The hairpin structure is further designed such that it does not inhibit annealing to target nucleic acids under conditions of the annealing step of a primer extension reaction. For example, two regions of a probe can have complementary sequences that do not substantially anneal at temperatures used during target hybridization, but become annealed to form a hairpin once the temperature is reduced for extension.

Although methods for reducing ectopic extension are exemplified above with respect to arrayed probes, those skilled in the art will recognize that the methods can be similarly applied to extension reactions in other formats such as solution phase reactions or beads spatially separated in fluid phase.

Under some extension assay conditions polymerases can place extra nucleotides at the end of 3' termini of a single stranded probe absent a hybridized template nucleic acid. Such an activity is also known to occur at the 3' termini of blunt ends of double stranded nucleic acids under some conditions and is referred to as a terminal extendase activity (see for example, Hu et al., *DNA and Cell Biology*, 12:763-770 (1993). Accordingly, an extension reaction used in the invention can be carried out under conditions that inhibit terminal extendase activity. For example, a polymerase can be selected that has sufficiently low levels of terminal extendase activity under the extension reaction conditions to be used or nucleotides that are preferentially incorporated by the extendase activity of a particular polymerase can be excluded from an extension reaction, or unhybridized probes can be blocked or removed from an extension reaction.

Direct hybridization detection of nucleic acid targets can suffer from decrease the assay specificity due to cross-hybridization reactions under some assay conditions. Array-based enzymatic detection of nucleic acid targets offers a powerful approach to increase specificity. In addition to the field of genotyping previously discussed, the invention can be applied to increasing specificity in detection of DNA copy number, microbial agents, gene expression, and so forth. This becomes particularly relevant as the complexity of the nucleic acid sample increases to the level of human genomic complexity. For instance, DNA copy number experiments in which labeled genomic DNA is hybridized to DNA arrays are often compromised by specificity problems. By employing direct hybridization in combination with an array-based enzymatic step such as primer extension, or others set forth previously herein, specificity can be dramatically improved. This is because cross-hybridizing targets will not be detected since labeling by the enzymatic detection step occurs due to perfect 3' complementarity.

In accordance with another embodiment of the present invention, there are provided diagnostic systems for carrying out one or more of the methods described previously herein. A diagnostic system of the invention can be provided in kit form including, if desired, a suitable packaging material. In one embodiment, for example, a diagnostic system can include a plurality of nucleic acid probes, for example, in an array format, and one or more reagents useful for detecting a gDNA fragment or other target nucleic acid hybridized to a probe of the array. Accordingly, any combination of reagents or components that is useful in a method of the invention, such as those set forth herein previously in regard to particular methods, can be included in a kit provided by the invention. For example, a kit can include one or more nucleic acid probes bound to an array and having free 3' ends along with other reagents useful for a primer extension detection reaction.

As used herein, the phrase "packaging material" refers to one or more physical structures used to house the contents of the kit, such as nucleic acid probes or primers, or the like. The packaging material can be constructed by well known methods, preferably to provide a sterile, contaminant-free environment. The packaging materials employed herein can include, for example, those customarily utilized in nucleic acid-based diagnostic systems. Exemplary packaging materials include, without limitation, glass, plastic, paper, foil, and the like, capable of holding within fixed limits a component useful in the methods of the invention such as an isolated nucleic acid, oligonucleotide, or primer.

The packaging material can include a label which indicates that the invention nucleic acids can be used for a particular method. For example, a label can indicate that the kit is useful for detecting a particular set of typable loci, thereby determining an individual's genotype. In another example, a label can indicate that the kit is useful for amplifying a particular genomic DNA sample.

Instructions for use of the packaged reagents or components are also typically included in a kit of the invention. "Instructions for use" typically include a tangible expression describing the reagent or component concentration or at least one assay method parameter, such as the relative amounts of kit components and sample to be admixed, maintenance time periods for reagent/sample admixtures, temperature, buffer conditions, and the like.

A method of the invention can include controls for determining desirable or undesirable outcome for one or more of the reagents, components, or steps disclosed herein. Comparison of results for a sample being investigated with results for controls can be performed in a method of the invention, thereby validating results, identifying steps that bear repeating or influencing interpretation of results. If the results for one or more controls are outside of a desired range of results a method of the invention can include a step of modifying a value or other data point obtained for a sample being investigated. A method of the invention can include determining results for one or more of the controls set forth below and if the results are outside of a desired range then repeating one or more steps of the method. Thus, detection of a signal from a control and modification of conditions can be carried out in an iterative fashion until a desired set of condition is obtained.

Amplification controls can be used in a method of the invention such as a method including a step of representationally amplifying a genome and/or producing genome fragments. An exemplary amplification control is an extrinsic genome spike. For example, a small amount of microbial genomic DNA can be spiked into a reaction for random primer amplification of a human genome. The amount of microbial genomic DNA added is typically sufficient to compete with potential contamination from other DNA samples but insufficient to substantially compete with amplification of the human genomic DNA sample. Detection of loci that are unique to the microbial genome compared to the human genome using, for example, a subset of probes that selectively hybridize to the microbial loci and not to human loci, can be used to determine whether a failed amplification is due to faulty RPA reaction components or poor quality human genomic DNA. More specifically, detectable levels of microbial loci resulting from the RPA reaction indicate that the human genomic DNA is poor quality and RPA reaction components are functional and, in contrast, absence of detectable levels of microbial loci indicate a failure of the reaction components.

Hybridization controls can be used in a method of the invention such as a method including a step of contacting genome fragments with a nucleic acid probes. Typically, hybridization controls are synthetic nucleic acids that are co-incubated with targets nucleic acids during a probe hybridization step. An example of a useful hybridization control is a set of stringency control probes having sequences forming a series of mismatches relative to the sequence of a stringency control target. The probe series can include a first probe having a sequence that is a perfect match with the sequence of the stringency control target, a second probe having a mismatch with the sequence of the stringency control target, a third probe having the same mismatch as the second probe and a second mismatch, a fourth probe having the same two mismatches as the third probe and a third mismatch etc. It is possible to have two or more mismatches per probe in this series. The mismatches in the series can be adjacent to each other or spaced apart from each other such that one or more matching nucleotides intervenes in the sequence. The mismatches in the series can be located near the 5' end of the probe such that all of the probes have a 3' end that matches perfectly with the stringency control target.

The number and/or identity of the stringency control probes that hybridize to the stringency control target can be correlated with the stringency of the hybridization conditions. At the highest stringency levels only the first stringency control probe in the above series (the perfect match control probe) will hybridize to the target control probe. Lower stringency conditions will result in more of the stringency control probes in the series hybridizing to the stringency control target. Thus, stringency control probes can be used to identify conditions that provide a desired stringency for hybridization for genome fragments and probes.

A further control that can be used is a concentration control. A concentration control target having a sequence that is a perfect match with the sequence of a concentration control probe can be used. Concentration control targets can be provided at different concentrations to control probes. The lower limit of detection for a particular set of assay conditions can be quantified by determining the lowest concentration of target detected. If desired, the concentration control target can have one or more mismatches to the control probe, for example, at the 3' end of the target sequence. Accordingly, stringency or specificity evaluation can also be made with concentration probes.

Probe modification controls can be used in a method of the invention such as a method including a step of modifying a probe while hybridized to a genome fragment. Examples of probe modification controls are extension controls that indicate levels of probe extension by polymerase in a method of the invention. An exemplary extension control is a hairpin probe or set of match and mismatch hairpin probes. The set can include two or more of the 16 possible combinations of matches and mismatches that arise for 4 nucleotides (for example, a GC match and at least one of GA, GT and GG). Hairpin probes are typically attached to a substrate at their 5' ends and have a palindromic sequence such that they can form a hairpin structure at their 3' ends under permissible stringency conditions. The match probe will have a hairpin terminating in a 3' base pair match, whereas the mismatch probe will terminate in a 3' mismatch. Modification of the match hairpin probe indicates that the extension assay components are functional under the conditions being employed. An advantage of using hairpin control probes is that the indication is independent of presence of target nucleic acids. Thus, for a failed extension reaction the results for the match hairpin control can be used to determine if problems arose from the target nucleic acid sample or the other extension reaction reagents. Modification of the mismatch hairpin probe can be monitored to determine if the extension reaction reagents are modifying probes in a template independent fashion. Although the hairpin control probes have been exemplified above with respect to extension reactions, those skilled in the art will recognize that they can be used in other template-dependent modification reactions such as a ligation reaction.

Another useful probe modification control is an extension efficiency control. An extension efficiency control can include a set of extension efficiency control probes that are complementary to overlapping sequences of an extension efficiency control target such that the 3' ends of the probes complement an A, C, T or G nucleotide, respectively, of a 4 nucleotide sequence. Thus, a sequence alignment of an extension efficiency control target with four such extension efficiency control probes appears as a staggered set of sequences offset at their 3' ends by one nucleotide. An extension efficiency control can be useful for determining whether or not selected extension reaction conditions are balanced with respect to incorporating all of the nucleotides being used or if one or more nucleotide is being incorporated selectively.

A method of the invention can further include evaluation of non-polymorphic controls. A non-polymorphic control is a set of perfect match and mismatch probes for a non-polymorphic sequence in a genome. The perfect match and mismatch probes are complementary to the same region of the genome with the exception that their 3' ends are either complementary or non-complementary, respectively, to the genome sequence region. One or more sets can be used, for example, having different GC contents to monitor stringency, and/or having one or more of all possible combinations of matches and mismatches. Polymorphic probes can facilitate assay optimization using single or mixed individual samples when compared to clustering data with multiple individuals.

Strip controls can be used in a method of the invention such as a method including a step of removing genome fragments from a plurality of probes. For example, a labeled strip control target can be spiked into a genome fragment sample prior to hybridization with a plurality of probes such that once the hybrids have been treated to remove genome fragments the presence or absence of the labeled target can be detected and correlated with unsatisfactory or satisfactory fragment removal, respectively. In particular embodiments, a label can be incorporated into a strip control target while hybridized to a complementary probe. For example, the 3' end of the strip control target can hybridize to the probe such that the target can be modified in a template dependent fashion. Typically, the strip control target and its complementary probe are designed such that the probe is not modified in the same step as the target. For example, the probe can have a 3' nucleotide analog that is not amenable to modification and/or the 3' end of the probe can form a mismatch with the target. Furthermore, the probe that complements the strip control target can be designed to have a sequence that will not complement any of the genome fragments to be detected in a method of the invention.

Detection controls can be used in a method of the invention such as a method including a step of detecting typable loci of probe-fragment hybrids. For example, a set of label control probes can be used that have known amounts of label associated. The label control probes can be analyzed as a titration curve to determine the sensitivity or range of detection for the label used to detect typable loci of genome fragments. The label control probes need not be the same type of molecule as the probes used for detection of genome fragments. Accordingly, label control probes can be labels attached directly or indirectly to a particular location on an array surface. In the case of on-array biotin-based detection, label control probes can be array locations having known amounts of covalently attached biotin.

Although the invention is exemplified herein with respect to an array of immobilized probes, those skilled in the art will recognize that other detection formats can be employed as well. For example, the methods set forth herein can be carried out in solution phase rather than solid phase. Accordingly, solution phase probes can replace immobilized probes in the methods set forth above. Solution phase probes can be detected according to properties such as those set forth above in regard to detection labels or detection moieties. For example, probes can have identifiable charge, mass, charge to mass ratio or other distinguishing properties. Such distinguishing properties can be detected, for example, in a chromatography system such as capillary electrophoresis, acrylamide gel, agarose gel or the like, or in a spectroscopic system such as mass spectroscopy. Thus, the invention further provides a method of detecting typable loci of a genome including the steps of (a) providing an amplified representative population of genome fragments having the typable loci; (b) contacting the genome fragments with a plurality of nucleic acid probes having sequences corresponding to the typable loci under conditions wherein probe-fragment hybrids are formed; (c) modifying the probe-fragment hybrids; and (d) detecting a probe or fragment that has been modified, thereby detecting the typable loci of the genome.

Example I

Whole Genome Amplification Using Random-Primed Amplification (RPA)

This example demonstrates production of an amplified representative population of genome fragments from a yeast genome.

Yeast genomic DNA, from *S. Cerevisiae* strain S228C, was prepared using a Qiagen Genomic DNA extraction kit and 10 ng of the genomic DNA was amplified with Klenow polymerase.

Figure 3:
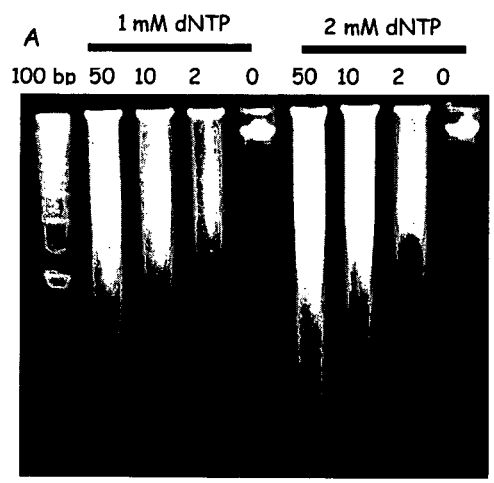
FIG. 3 shows, in Panel A, agarose gels loaded with amplification products from whole genome amplification reactions carried out under various conditions, and in Panel B, a table of yields calculated for the reactions.

Several parameters were evaluated to determine their effect on the yield of the Klenow (exo⁻) random-primed amplification reaction. Amplification reactions were carried out under similar conditions with the exception that one parameter was systematically modified. FIG. 3 shows results comparing amplification reactions carried out at different concentrations of deoxynucleotide triphosphates.

Following each reaction, the amplified DNA was purified on Montage ultrafiltration plates (Millipore), loaded onto an agarose gel and the DNA quantitated by $UV_{260}$ reading as shown in FIG. 3A. The amplification yield was determined based on the density of stain in each lane and the results are shown in the table in FIG. 3(B). As shown in the last two columns of FIG. 3B, 10 ng of yeast genome template was amplified to quantities in the range of about 6 to 80 microgram, representing about 600 to 8000 fold amplification. The average fragment size under the conditions tested was about 200-300 bp.

The results demonstrated that amplification yields were increased at higher concentrations of primer or deoxynucleotide triphosphates. Thus, reaction parameters can be systematically modified and evaluated to determine desired amplification yields.

Example II

Detection of Yeast Loci for a Yeast Whole Genome Sample Hybridized to BEADARRAYS™

This example demonstrates reproducible detection of yeast loci for a yeast whole genome sample hybridized to a BEADARRAYS™ and probed with allele-specific primer extension (ASPE).

Six hundred nanograms of random primer amplified (RPA) yeast gDNA was hybridized to a locus-specific BEADARRAY™ (Illumina). The BEADARRAY™ was composed of 96 oligonucleotide probe pairs (PM and MM, 50 bases in length) interrogating different gene-based loci distributed throughout the *S. cerevisiae* genome. The amplified yeast genomic DNA was hybridized to the BEADARRAY™ under the following conditions: Overnight hybridization at 48° C. in standard 1× hybridization buffer (1 M NaCl, 100 mM potassium-phosphate buffer (pH 7.5), 0.1% Tween 20, 20% formamide). After hybridization, arrays were washed in 1× hybridization buffer at 48° C. for 5 min. followed by a wash in 0.1× hybridization buffer at room temperature for 5 min. Finally, the array was washed for 5 min. with ASPE reaction buffer to block and equilibrate the array before the extension step. ASPS reaction buffer (10×GG Extension buffer (Illumina, Inc., San Diego, Calif.), 0.1% Tween-20, 100 ug/ml BSA, and 1 mM dithiothreitol, 10% sucrose, 500 mM betaine).

An ASPE reaction was performed directly on the array as follows. The BEADARRAY™ were dipped into 50 uls of an ASPE reaction mix containing the described ASPE reaction buffer supplemented with 3 uM dNTPs (1.5 uM dCTP), 1.5 uM biotin-11-dCTP, ~0.4 ul Klentaq (DNA Polymerase Technology, Inc, St. Louis, Mo., 63104). The BEADARRAYS™ were incubated in the ASPE reaction for 15 min. at room temperature. The BEADARRAYS™ were washed in fresh 0.2 N NaOH for 2 min., then twice in 1× hybridization buffer for 30 sec. The incorporated biotin label was detected by a sandwich assay employing streptavidin-phycoerythrin and biotinylated anti-streptavidin staining. This was done as follows: BEADARRAYS™ were blocked at room temperature for 30 min in casein block (Pierce, Rockford, Ill.). This was followed by a quick wash (1 min.) in 1× hybridization buffer, before staining for 5 min. at room temp. with streptavidin-phycoerythrin (SAPE) solution (1× hybridization buffer, 0.1% Tween 20, 1 mg/ml BSA, 3 ug/ml streptavidin-phycoerythrin (Molecular Probes, Eugene, Oreg.). After staining, the BEADARRAYS™ were quick washed with 1× Hyb. buffer before counterstaining with 10 ug/ml biotinylated anti-streptavidin antibody (Vector Labs, Burlingame, Calif.) in 1× TBS supplemented with 6 mg/ml goat serum, Casein and 0.1% Tween 20. This step was followed by a quick wash in 1× Hyb. buffer, and than a second staining with SAPE solution as described. After staining, a final wash in 1× Hyb. buffer was performed.

Figure 4:
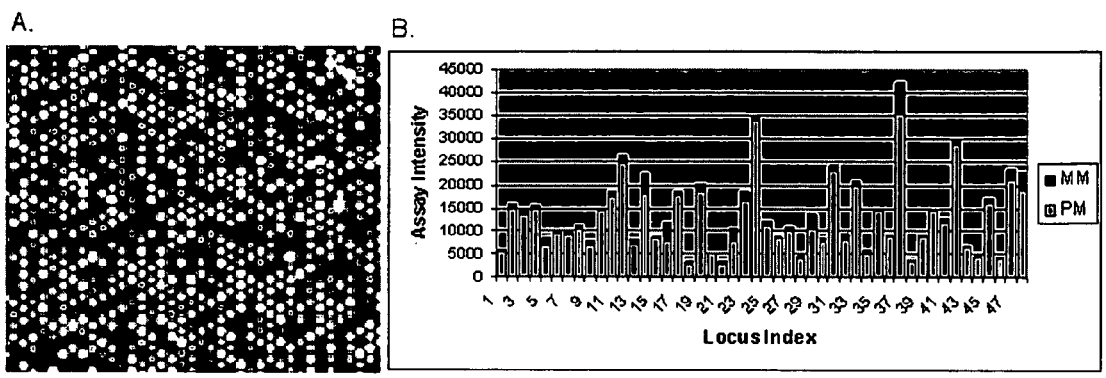
FIG. 4 shows an image of an array signal from yeast genomic DNA assayed on a BEADARRAY™ (Panel A) and a subset of perfect match (PM) and mismatch (MM) intensities for 18 loci out of 192 assayed from four different quadruplicate arrays (R5C1,R5C2,R6C1,R6C2) (Panel B). The PM probes are the first set of four intensity values and MM probes are the second set of four intensity values denoted by each probe type label on the lower axis.

The left panel of FIG. 4 shows an image of an array following hybridization with amplified whole yeast genome sample and ASPE detection. The chart in the right panel of FIG. 4 displays a subset of perfect match (PM) and mismatch (MM) intensities (48 loci out of 96). Greater than 88% of the loci had PM/MM ratios greater than 5 indicating the ability to distinguish most loci from alternate genotypes.

The ability to distinguish typable loci in genomes of higher complexity than yeast was assessed by spiking yeast genomic DNA into the genomic background of a more complex organism. Six hundred nanograms Yeast genomic DNA (12 Mb complexity) was spiked into 150 ug human genomic DNA (3000 Mb complexity) to mimic the presence of single copy loci in a genome having complexity equivalent to human. Hybridization of this spiked sample to the array showed very little difference with yeast DNA hybridized alone indicating the ability of the array to specifically capture the correct target sequences in a complex genomic background.

These results demonstrate detection of several typable loci of a yeast genome following hybridization of a whole genome sample to an array. These results further demonstrate that amplification is not necessary to detect a plurality of typable loci in a whole genome sample. Furthermore the results were reproducible showing that the method is robust.

Example III

Whole Genome Genotyping (WGG) of Human gDNA Directly Hybridized to BEADARRAYS™

This example demonstrates hybridization of a representative population of genome fragments to an array and direct detection of several typable loci of the hybridized genome fragments. This example further demonstrates detection of typable loci on an array using either of two different primer extension assays.

SBE-Based Detection

Human placental genomic DNA samples were obtained from Coriell Inst. Camden, N.J. The human placental gDNA sample (150 ug) was hybridized to a BEADARRAY™ (Illumina) having 4 separate bundles each containing the same set of 24 different non-polymorphic probes (50-mers). The BEADARRAY™ consisted of 96 probes to human non-polymorphic loci randomly distributed throughout the human genome. The probes were 50 bases long with ~50% GC content and designed to resequence adjacent A (16 probes), C (16 probes), G (16 probes), or T (16 probes) bases. DNA samples (150 ug human placental DNA) were hybridized overnight at 48° C. in standard 1× hybridization buffer (1 M NaCl, 100 mM potassium-phosphate buffer (pH 7.5), 0.1% Tween 20, 20% formamide) in a volume of 15 ul.

Four separate SBE reactions were performed directly on the array, one for each separate bundle, as follows. The "A" reaction contained biotin-labeled ddATP and unlabeled ddCTP, ddGTP, and ddTTP. The other three SBE reactions were similar except that the labeled and unlabeled designations were adjusted appropriately. The SBE reaction conditions were as follows: The BEADARRAYS™ were dipped into an SBE reaction mix at 50° C. for 1 min. Four different SBE reaction mixes were provided, an A, C, G, or T resequencing mix. For example, a 50 ul A-SBE resequencing mix contained 1 uM biotin-11-ddATP (Perkin Elmer), 1 uM ddCTP, 1 uM ddGTP, and 1 uM ddUTP, 1× Thermosequenase buffer, 0.3 U Thermosequenase, 10 ug/ml BSA, 1 mM DTT, and 0.1% Tween 20. The other three SBE mixes were similar with the appropriate labeled base included and the other bases unlabeled.

Figure 5:
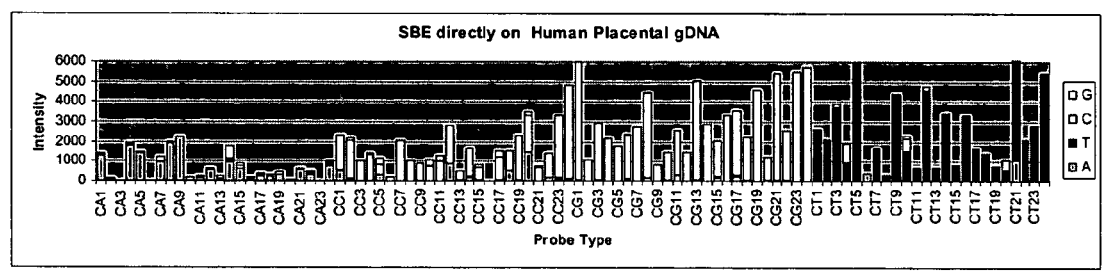
FIG. 5 shows array-based SBE genotyping performed on human gDNA directly hybridized to BEADARRAYS™.

The results of the SBE reactions are shown in FIG. 5. In FIG. 5, the set of 96 probes are divided into four groups corresponding to the four different reactions designated as CA1 through CA24 for the biotin-labeled ddATP reaction, CC1 through CC24 for the biotin-labeled ddCTP reaction, CG1 through CG24 for the biotin-labeled ddGTP reaction, and CT1 through CT24 for the biotin-labeled ddTTP reaction. As shown in FIG. 5 most probes showed excellent signal discrimination.

ASPE-Based Detection

A similarly prepared human placental gDNA sample (150 ug) was hybridized to a BEADARRAY™ containing 77 functional perfect match (PM) and mismatch (MM) probe pairs querying non-polymorphic loci. The ASPE probes were designed to non-polymorphic sites within the human genome. The probes were 50 bases in length with ~50% GC content. The perfect match (PM) probes were completely matched to genomic sequence whereas the mismatch (MM) probes contained a single base mismatch to the genomic sequence at the 3' base. The mismatch type was biased towards modeling A/G and C/T polymorphisms. The hybridization and reaction conditions were as previously described in Example II.

Figure 6:
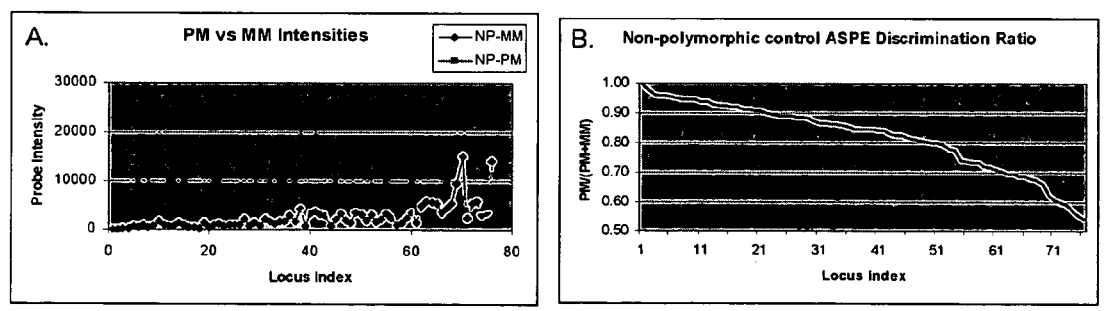
FIG. 6 shows array-based ASPE genotyping performed on human gDNA directly hybridized to a BEADARRAY™. Panel A shows raw intensity values across the 77 probe pairs and Panel B shows the discrimination ratios (PM/PM+MM) plotted for the 77 loci.

An allele-specific primer extension reaction (ASPE) was performed directly on the array surface, and the incorporated biotin label detected with streptavidin-phycoerythrin staining. The ASPE reaction was performed as follows. BEADARRAYS™ were washed twice in 1× hybridization buffer and then washed with ASPE reaction buffer (without enzyme and nucleotides) at room temperature. The ASPE reaction was carried out by dipping the BEADARRAYS™ into a 50 ul ASPE reaction mix at room temperature for 15 minutes. The ASPE mix contained the following components: 3 uM dATP, 1.5 uM dCTP, 1.5 uM biotin-11-dCTP, 3 uM dGTP, 3 uM dUTP, 1× GOLDENGATE® extension buffer (Illumina), 10% sucrose, 500 mM betaine, 1 mM DTT, 100 ug/ml BSA, 0.1% Tween 20 and 0.4 ul Klentaq (DNA Polymerase Inc., St. Louis, Mo.). FIG. 6A shows the raw intensity values across the 77 probe pairs, The PM probes (squares) exhibit much higher intensities than the MM probes across a majority of the probes effectively allowing the queried base to be distinguished. FIG. 6B shows a plot of the discrimination ratios (PM/PM+MM) for the 77 loci. These results demonstrated that about two thirds of the loci had ratios >0.8.

The results of this example demonstrate that hybridization of a representative population of genome fragments to an array and direct detection of several typable loci of the hybridized genome fragments provides sufficient locus discrimination for genotyping applications.

Example IV

Genotyping of Amplified Genomic DNA Fragments

This example demonstrates genotyping of an amplified population of genome fragments.

Figure 7:
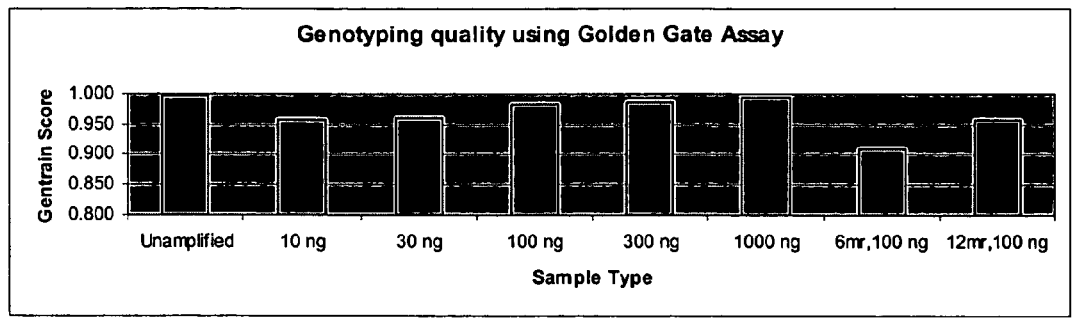
FIG. 7 shows Genotyping scores of unamplified genomic DNA compared to random primer amplified (RPA) genomic DNA using the GOLDENGATE® assay (the amount of DNA input in the RPA reaction is shown below each bar, the RPA reactions employed random 9-mer oligonucleotides, except where the use of hexanucleotides (6-mer) or dodecanucleotides (12-mer) are specified).

Human placental genomic DNA samples were obtained from Coriell Inst. Camden, N.J. The genome was amplified and biotin labeled using random primer amplification under conditions described in Example I, with the exception that the amount of template genome was varied and length of the random primer was varied as indicated in FIG. 7. The amplification output for all reactions was relatively constant at about 40 ug of amplified genome fragments per 40 ul reaction.

The amplified population of genome fragments was genotyped as follows. The genotyping was performed by Illumina's SNP genotyping services using the proprietary GOLDENGATE® assay on Illumicode arrays. The GenTrain score is a metric for how well the genotype intensities of the SNP loci cluster across a sample population. A comparison of GenTrain score to the unamplified control provides an estimate of locus amplification and bias.

The genotyping quality for unamplified DNA was compared to the amplified population of genome fragments as shown in FIG. 7. The amount of genome template used in the amplification reaction is shown below each bar. Of the amplified samples, the best GenTrain scores were obtained for the amplification reaction using 1000 ng of template genome (40x amplification). The GenTrain scores for the amplification reaction using 1000 ng of template genome were similar to that obtained for unamplified genomic DNA, indicating that the amplified product was representative of the genome. Acceptable GenTrain scores were also obtained for amplification reaction using as little as 100 ng of template genome (400x amplification).

These results demonstrate that amplified populations of genome fragments obtained in accordance with the invention are representative of the genome sequence in a genotyping assay.

Example V

Whole Genome Genotyping (WGG) of Amplified Genomic DNA Fragments

This example demonstrates whole genome genotyping of an amplified population of genome fragments by direct hybridization to a DNA array and array-based primer extension SNP scoring.

Figure 11:
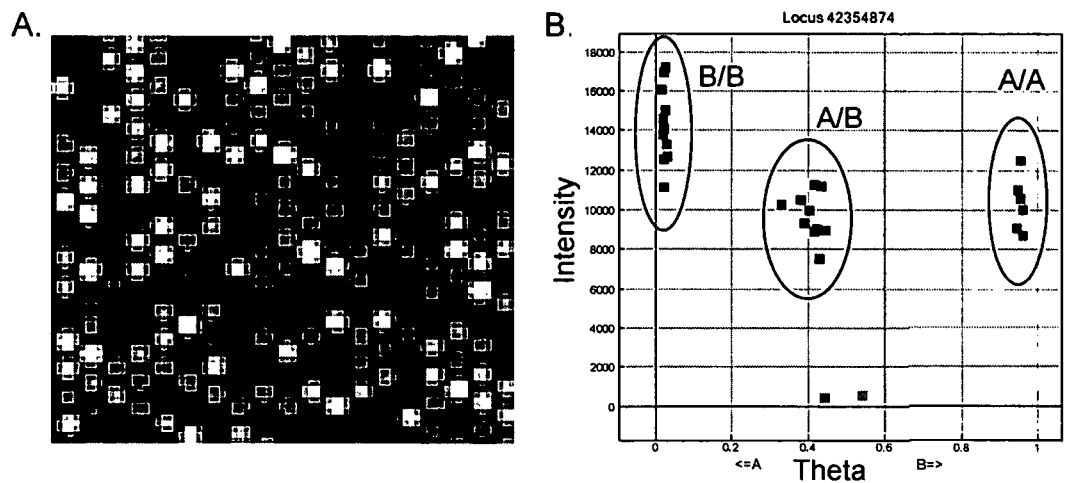
FIG. 11 shows, in Panel A, an image of a BEADARRAY™ hybridized with genomic DNA fragments and detected with ASPE, and in Panel B, a GenTrain plot in which two homozygous (BIB and A/A) clusters and one heterozygous (A/B) cluster at one locus are differentiated.

A set of 3×32 DNA samples (1 ug each) were amplified by random primer amplification to produce separate target samples having 150 ug of genomic DNA fragments. The amplified populations of fragments were hybridized to BEADARRAYS™ having 50-mer ASPE capture probes covering 192 loci. After hybridization, an ASPE reaction was performed as described in Example III. Images were collected and genotype clusters analyzed using proprietary GenTrain software (Illumina). An exemplary image of a BEADARRAY™ detected with ASPE is shown in FIG. 11A.

FIG. 11B shows a GenTrain plot of theta vs. intensity for one locus. Intensity is the total fluorescence intensity detected for a particular bead. Theta corresponds to the position of a bead's fluorescence intensity on a scatter plot of fluorescence intensity for one allele of a locus vs. fluorescence intensity for a second allele of the locus. In particular, the position of a bead's fluorescence intensity on the scatter plot corresponds to a particular x,y coordinate and theta is the angle between the x axis and a line drawn from the origin to that x,y coordinate. As shown in FIG. 11B, two homozygous (B/B and A/A) clusters and one heterozygous (A/B) cluster were clearly differentiated.

Figure 12:
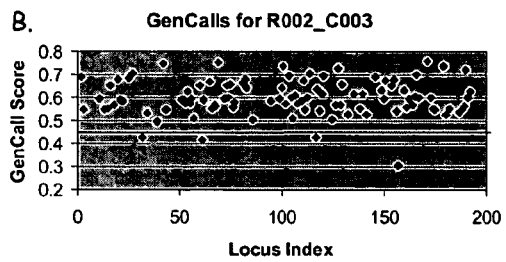
FIG. 12 shows, in Panel A, a table of genotyping accuracy statistics; in Panels B and C GenCall plots for two samples (the line at 0.45 indicates a lower threshold used to filter data to be called) and in Panels D and E, GenTrain plots for two loci (arrows indicate questionable data points that were not called as they fell below a threshold of 0.45 in GenCall plots).
Figure 12:
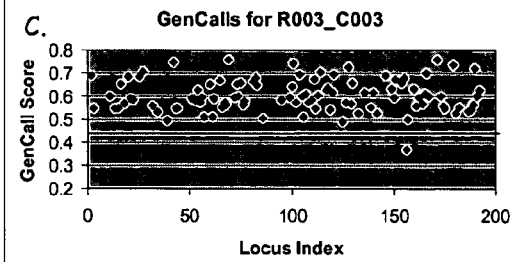
Figure 12:
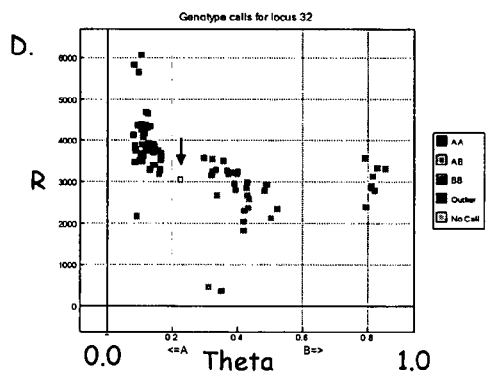
Figure 12:
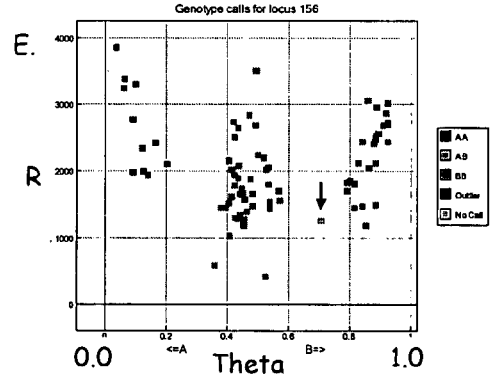

About 52% of the loci gave well resolved clusters which were termed "successful" loci and were subsequently analyzed for genotypes across all the samples. Analysis of the genotype calls (101/192 loci) across 3×16 samples for which reference genotypes were known indicated 99.95% concordance (4090/4092) with a call rate of 100% (FIG. 12, Panel A). GenCall plots showing the scores at different loci are shown in FIGS. 12B and C for two different samples. The GenCall score for an individual genotype call is a value between 0 and 1 that indicates the confidence in that call. A higher score indicates a higher confidence in the call.

Exemplary GenTrain plots for two different loci are shown in FIGS. 12C and 12D. This data shows that for the majority of samples, three clusters were clearly differentiated corresponding to homozygous (BB and A/A) and (A/B) genotypes. The two grey points are from "no target control" BEADARRAYS™.

Examination of the scatter plots in FIGS. 12D and E showed only two questionable calls out of 4092 calls, indicated by arrows in the plots. The calls were filtered by applying a threshold of 0.45 for the GenCall score, as shown by the horizontal line in FIGS. 12B and C.

Example VI

Inhibition of Ectopic Signals

This example demonstrates the use of single stranded nucleic acid binding protein (SSB) to inhibit ectopic expression in an array-based primer extension reaction.

Single stranded binding proteins such as E. coli SSB and T4 Gene 32 were tested for their ability to suppress ectopic extension in both Klenow and Klentaq array-based ASPE reactions. The conditions employed were as follows: Array-based Klenow ASPE reaction contained 80 mM Tris-Acetate (pH 6.4), 0.4 mM EDTA, 1.4 mM MgAcetate, 0.5 mM DTT, 100 ug/ml BSA, 0.1% Tween-20, 0.2 U/ul Klenow exo-polymerase, and 0.5 uM dNTPs with a 1:1 ratio of biotin-11 labeled nucleotides to "cold" nucleotides for dCTP, dGTP, and dUTP. In the experiments with SSB the concentration was 0.2 ug/20 ul rxn. Array-based Klentaq conditions are described in Example III.

Figure 14:
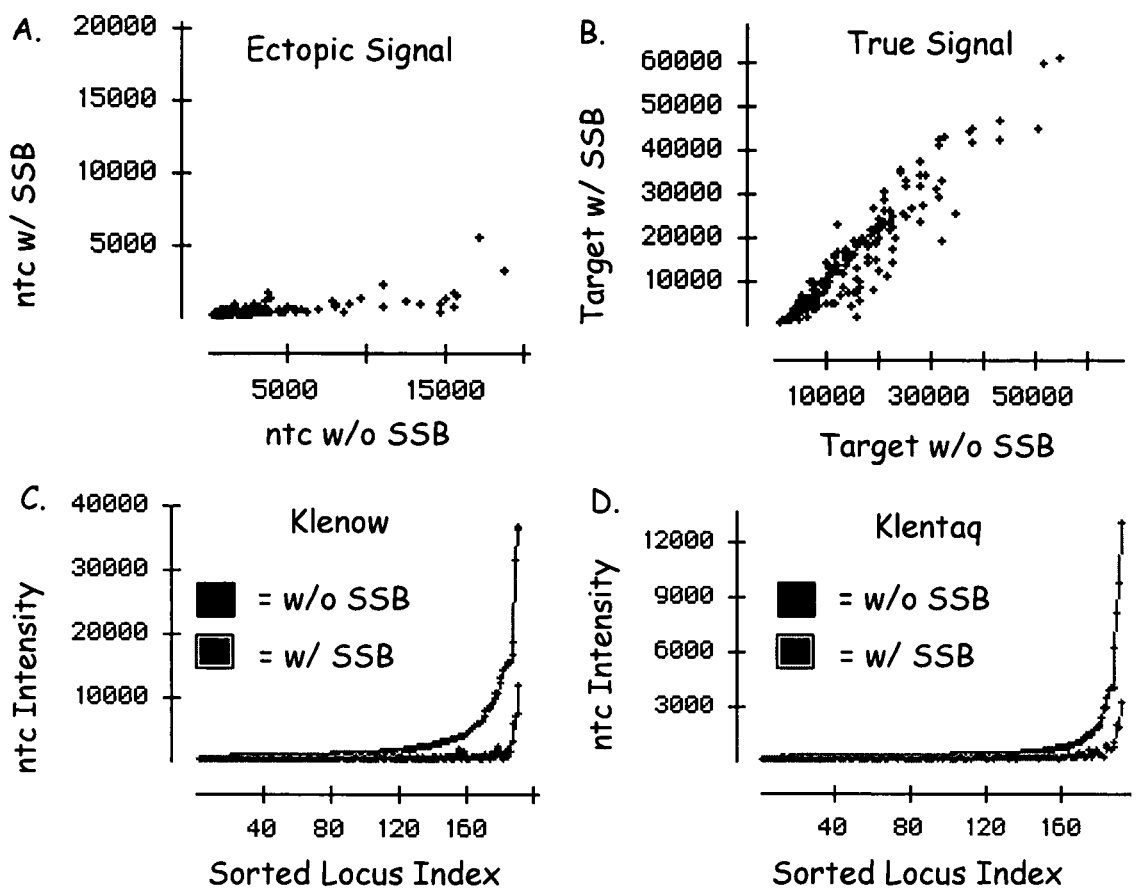
FIG. 14 shows scatter plots for Klenow-primed ASPE reactions on BEADARRAYS™ comparing assay signal in the presence and absence of single stranded binding protein (SSB). The scatter plot in panel A shows the effect of SSB on ectopic signal intensity in the absence of amplified genomic DNA, whereas the scatter plot in panel B shows the effect of SSB on signal intensity in the presence of amplified genomic DNA. Panels C and D show plots of the intensity for loci (sorted in order of increasing intensity) for either Klenow (Panel C) or Klentaq (Panel D) ASPE reactions run on BEADARRAYS™ in the absence of an amplified population of genome fragments (ntc—no target control provides a measure of "ectopic" extension).

FIG. 14A shows a scatter plot for an ASPE reactions run with Klenow polymerase on BEADARRAYS™ in the presence of SSB and absence of a target nucleic acid sample (ntc=no target control). As demonstrated by FIG. 14C, ectopic signal was greatly reduced in the presence of SSB compared to in the absence of SSB. Similar results were obtained for ASPE reactions run with Klentaq polymerase. The plots shown in FIGS. 14C and D were obtained by sorting signals from scatter plots along the X-axis according to increasing intensity. As shown in FIG. 14B, allele specific extension occurred at detectable levels for ASPE reactions carried out in the presence of a target sample containing an amplified population of genome fragments.

These results demonstrate that the inclusion of SSB in a primer extension assay suppresses ectopic extension while maintaining or improving allele-specific extension. Further studies have indicated that inclusion of SSB in an array-based ASPE reaction improved the allelic discrimination.

Example VII

Evaluation of Genome Fragment Populations Produced by Random Primer Amplification This example demonstrates that human genome fragment populations produced by random primer amplification (RPA) are representative of their genome templates, having little allelic bias and are capable of being reproducibly generated.

RPA reactions were used to produce amplified populations of genome fragments from human genomic DNA using methods described in Example V. The amplification reactions were carried out in a single tube format without the need for isolation of reaction components or products prior to incubating the reaction mixtures with probe arrays. With the exception of modifications described below, the reaction mixtures were incubated with BEADARRAYS™ as described in Example V and detection was carried out using ASPE as described in Example III.

The results shown in FIG. 15 illustrate the representation achieved in the amplification process. Duplicate RPA reactions carried out on 100 ng of human genomic DNA (Coriell Cell Repositories, Camden, N.J.) in 100 ul yielded populations of genome fragments having 1-2 ug DNA/ul. Duplicate unamplified genome samples consisted of human placental DNA (Sigma-Aldrich, Part No. D3287) that was fragmented with DNAse I to an average size of about 200 to 300 bases.

Figure 15A:
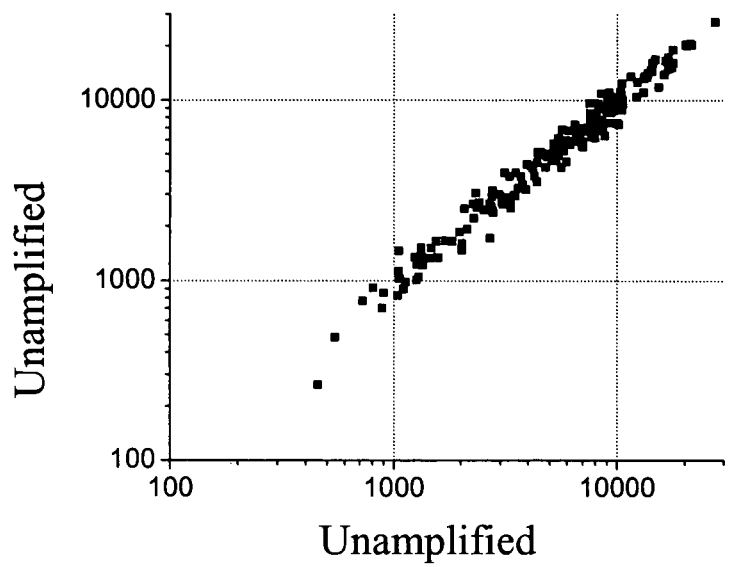
FIG. 15 shows scatter plots comparing intensity values for probes following ASPE detection of populations of genome fragments produced by random primer amplification (amplified) and/or unamplified genomic DNA (unamplified).
Figure 15B:
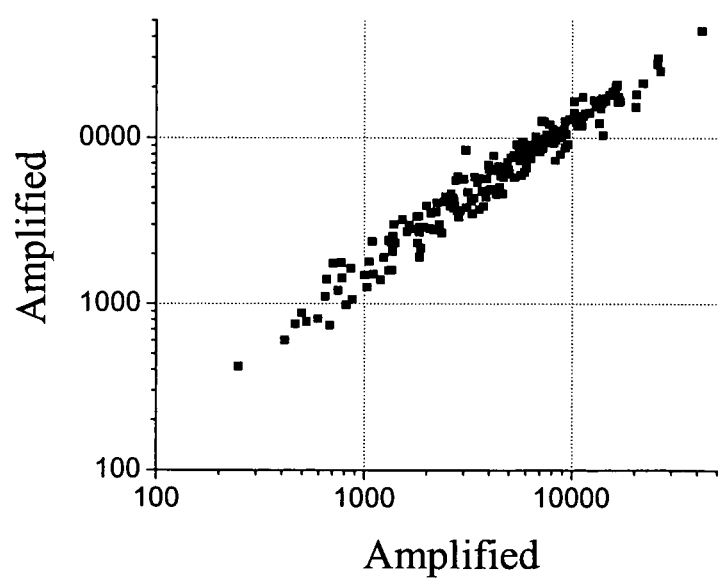
Figure 15C:
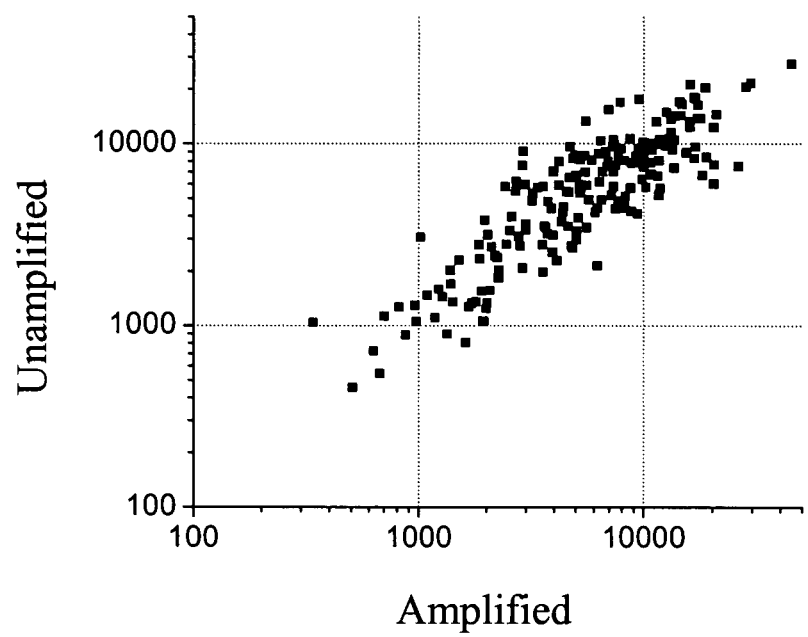

Amplified and unamplified samples were hybridized to arrays with probes designed to non-polymorphic regions of the genome. As such, all probes were perfect matches to the genome and should extend in the genotyping assay. The intensity values obtained for individual probes following hybridization to two different samples are plotted in the scatter plots of FIG. 15. As shown in FIG. 15A, a high degree of correlation occurred between duplicate unamplified samples. Similarly and as shown in FIG. 15B, strong correlation was observed between duplicate amplified samples, indicating that the amplification methods gave/highly reproducible results. The amplified vs. unamplified scatterplot of FIG. 15C, showed a more diffuse cluster compared to those observed for the duplicates and indicates that some loci were over-represented whereas others were under represented in the amplified sample.

Figure 16A:
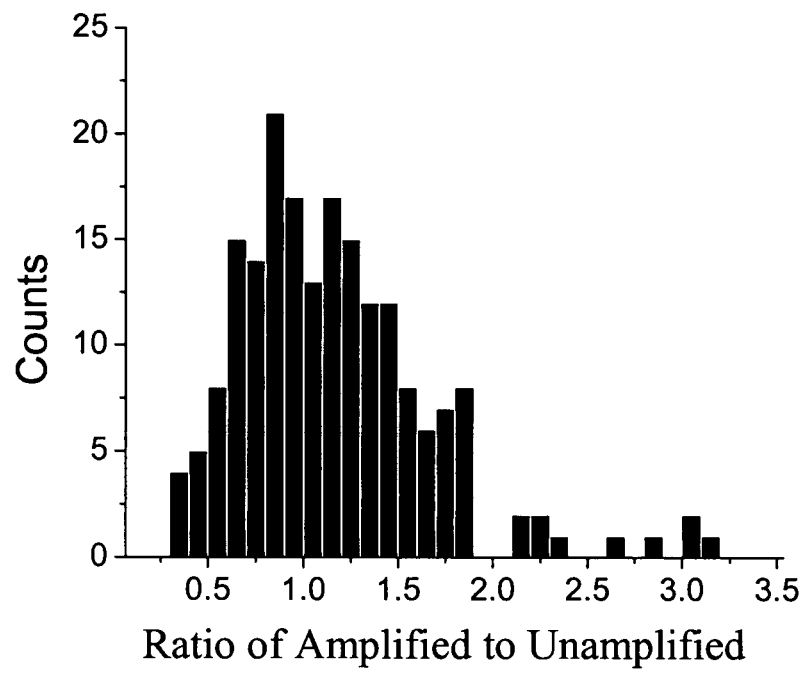
FIG. 16 shows a distribution of the number of probes (counts) having particular ratios of signal intensities for unamplifed to amplified DNA inputs (ratio of amplified:unamplified).
Figure 16B:
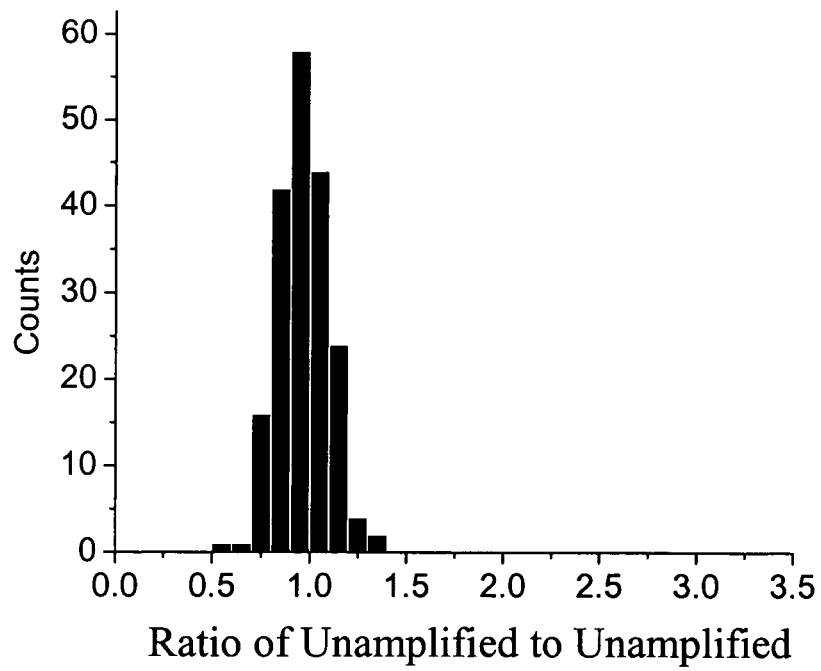

Nevertheless, the results indicated good representation. The number of probes (counts) having particular ratios of signal intensities for unamplifed to amplified DNA inputs (ratio of amplified:unamplified) is plotted in FIG. 16A. The data demonstrated that 90.1% of the detected loci had an intensity variance in the amplified population that did not exceed 0.5- to 2-fold compared to the intensity measured for unamplified genomic DNA. Thus, 90.1% of the detected loci in the amplified population were represented in no less than 0.5 fold shortage and no more than 2 fold excess compared to their relative amounts in the unamplified genome. Furthermore, 97.4% of detected loci in the amplified population were represented in no less than 0.3 fold shortage and no more than 3-fold excess compared to their relative amounts in the unamplified genome.

Figure 17:
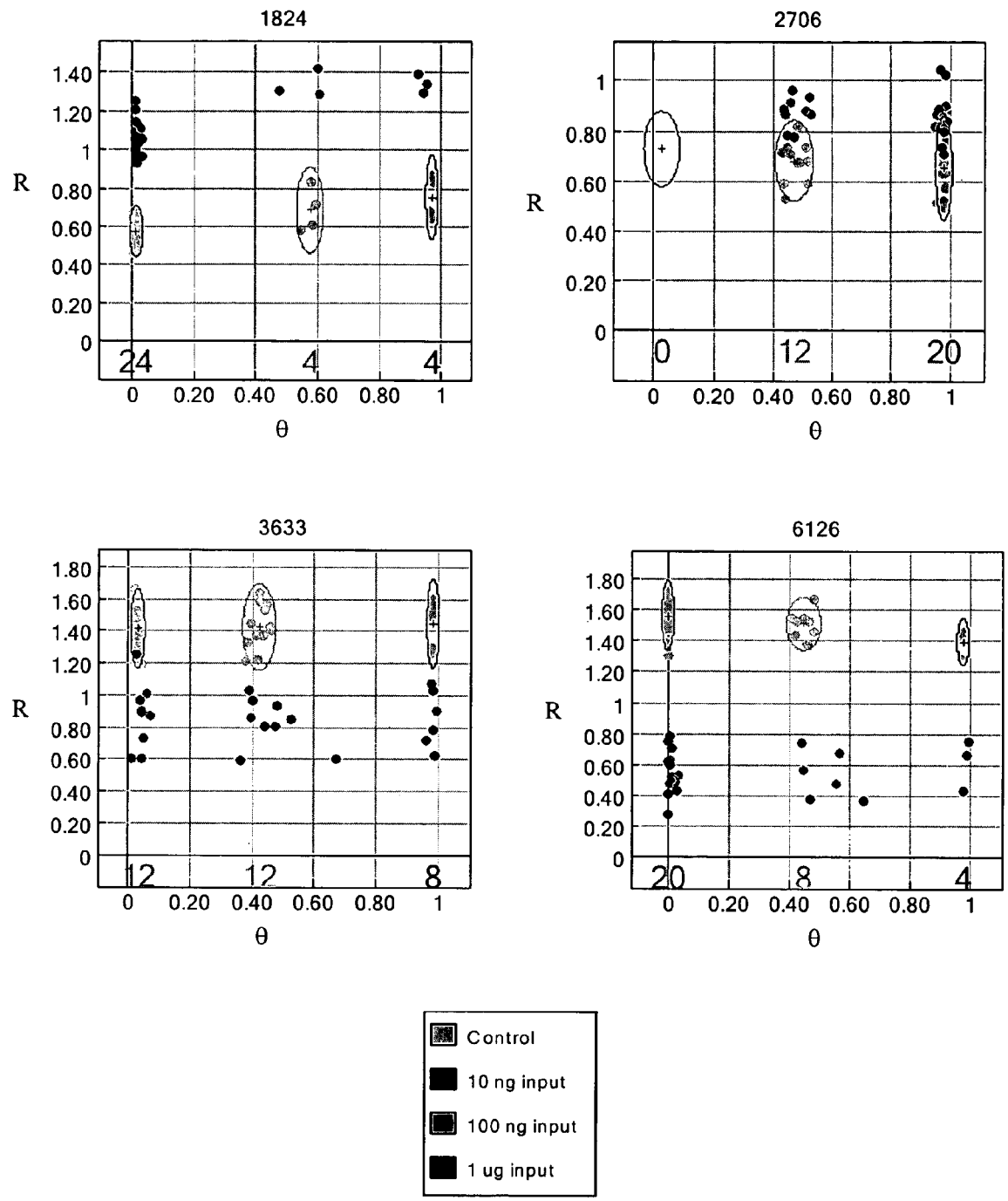
FIG. 17 shows exemplary genoplots for four loci (1824, 2706, 3633 and 6126) detected from representationally amplified populations of genome fragments using the GOLDENGATE® assay. Representationally amplified populations of genome fragments were separately produced from genomic DNA samples in the three different amounts indicated in the legend. Control data points were obtained for unamplified genomic DNA detected under the same conditions using the GOLDENGATE® assay. Clusters for control data points identified by the GenTrain algorithm are circled and the number of data points in each cluster indicated below the x-axis. For the 2706 locus the empty cluster indicates a predicted cluster location for the AA genotype based on locations of the AB and BB clusters.

The representationally amplified population of genome fragments was compared to unamplified control DNA samples in the GOLDENGATE® assay (Illumina, Inc. San Diego, Calif.). Exemplary data for four loci (1824, 2706, 3633 and 6126) is shown in the Genoplots (also called Gen-Train plots) of FIG. 17. The genoplots are polar coordinate replots of standard genotyping scatter plots. Standard genotyping scatter plots have an axis of intensity detected for a first channel (correlated with a first allele) vs, intensity detected for a second color channel (correlated with a second allele) and plot a scatterpoint for each locus according to its intensity in each channel. Genoplots are replots of each scatter point according to the distance of a line drawn from the origin to the scatter point (R) and the angle between the line and the x axis (theta). As shown in FIG. 17, scatterpoints for data generated from RPA mixtures produced from 10 ng, 100 ng or 1 ug genome inputs resulted in good clusters compared to control clusters (circled) from unamplified genomic DNA, indicating very little allelic bias.

Figure 18A:
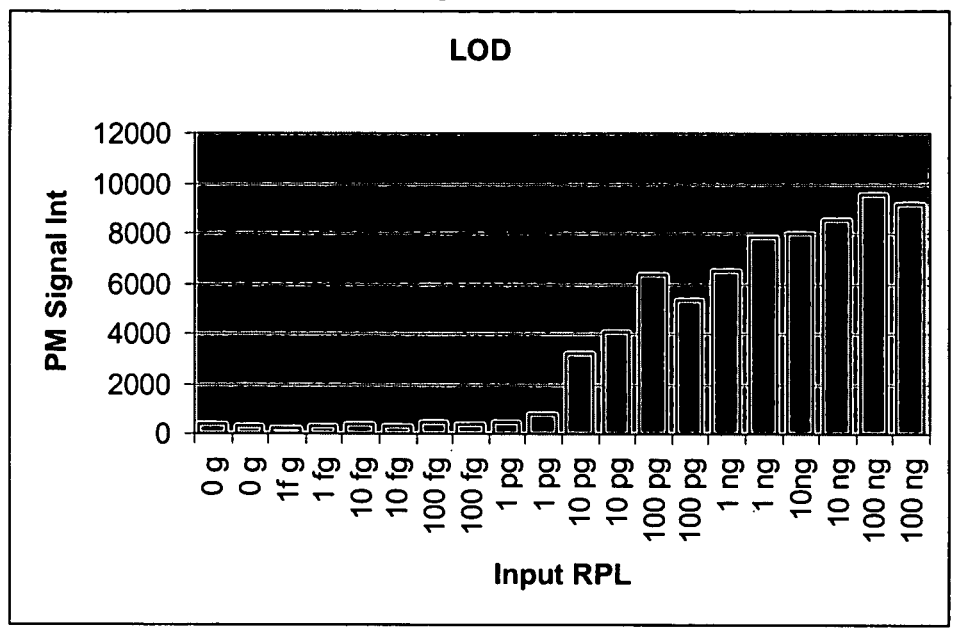
FIG. 18 shows (A) a bar graph plotting the average intensity detected for all probes on each array (LOD) following hybridization and ASPE detection of RPA reaction mixtures generated from different amounts of input genomic DNA (input) and (B) a bar graph plotting the ratio (PM signal intensity/(PM signal intensity+MM signal intensity) for all probes of an array (ratio) when used to probe RPA mixtures produced from varying amounts of input genomic DNA (input).

The limit of detection (LOD) in genotyping assays was shown to increase as increasing amounts of genomic DNA were input into RPA reactions. Separate RPA reactions were carried out (in duplicate) with various amounts of input genomic DNA. The input amounts were in the range of 1 femtogram to 100 nanograms, including the amounts plotted on the x-axis of FIG. 18A. FIG. 18A is a bar graph showing the average intensity detected for all probes on each array (LOD) following hybridization and ASPE detection of RPA reaction mixtures generated from different amounts of input genomic DNA (input). As shown in FIG. 18A amounts of input genomic DNA of 10 pg (approximately 3 copies of the human genome) or greater resulted in LOD values that were substantially increased compared to a control RPA reaction in which no input genomic DNA was used (0 g). LOD was substantially increased over background when at least 100 pg (30 genome copies), 1 ng (300 genome copies), 10 ng (3,000 genome copies) or 100 ng (30,000 genome copies) of input human genomic DNA was used for the RPA reaction as shown in FIG. 18A.

Figure 18B:
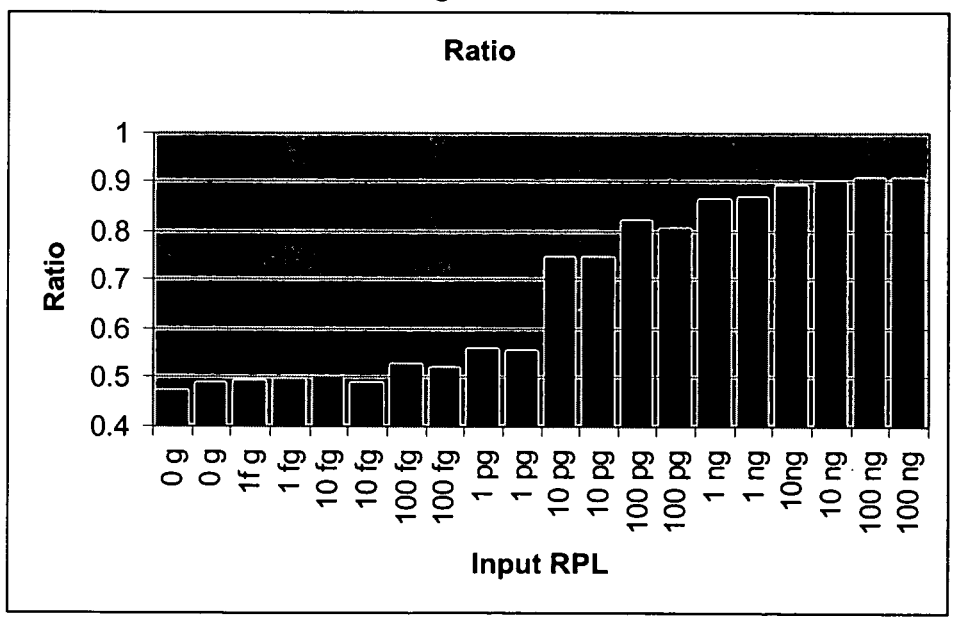

Representation was shown to improve as increasing amounts of genomic DNA were input into RPA reactions. The bar graph shown in FIG. 18B plots PM/(PM+MM) for all probes of an array (ratio) when used to probe RPA mixtures produced from varying amounts of input genomic DNA (input). Amounts of input genomic DNA of 10 pg (approximately 3 copies of the human genome) or greater resulted in a substantial improvement in representation when compared to a control RPA reaction in which no input genomic DNA (0 g) or low levels of genomic DNA (femtogram amounts) were used. Representation was further substantially improved when at least 100 pg (30 genome copies), 1 ng (300 genome copies), 10 ng (3,000 genome copies) or 100 ng (30,000 genome copies) of input human genomic DNA was used for the RPA reaction.

These results indicate that RPA can be used to produce hundreds of micrograms of an amplified population of genome fragments from quantities of genomic DNA template as low as a few picograms. The amplified populations of genome fragments produced by RPA have good representation, can be reproducibly made and have little allelic bias. Thus, the DNA produced by RPA is of sufficient quantity and quality for whole genome genotyping.

Example VIII

Whole Genome Genotyping Assay Performance

This Example demonstrates that whole genome genotyping of an amplified population of genome fragments by direct hybridization to a DNA array and array-based primer extension produces accurate, high quality SNP scoring results for human subjects.

Genomic DNA (100 ng) was obtained from 95 samples in the Centre d'Etude du Polymorphisme Humain (CEPH) in the set used for quality control of the International HapMap project (for sample information see International HapMap Consortium, Nature 426:789-796 (2003)). RPA reactions were carried out as described in Example V, resulting in reaction mixtures, containing 188 ug of DNA in 100 ul. The undiluted reaction mixtures were incubated with the BEADARRAYS™ having 50-mer probes specific for the 1500 HapMap QC set of loci (for loci information see International HapMap Consortium, Nature 426:789-796 (2003)) using methods described in Example V followed by ASPE as described in Example III. Arrays were then imaged on a charge coupled device reader as described in Gunderson et al., Genome Res. 14:870-877 (2004). SNP genotypes were called using GenCall software (Illumina Inc., San Diego, Calif.).

Figure 19A:
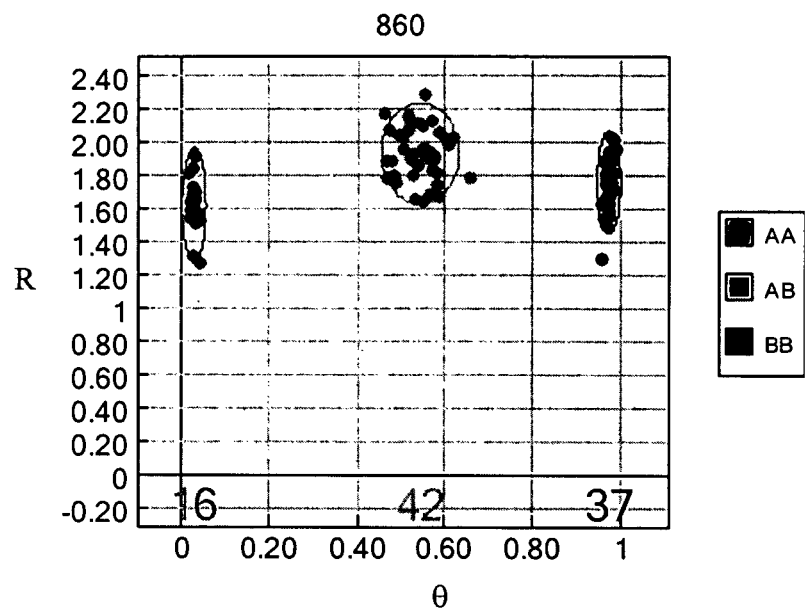
FIG. 19 shows representative Genoplots for the 860 locus (panel A) and 954 locus (Panel B) for random primer amplified human genome fragments produced from 95 CEPH human samples and detected by allele specific primer extension of probes on an array having probes specific for the 1500 HapMap QC set of loci. Panel C shows the distribution of loci according to genotype cluster separation score.
Figure 19B:
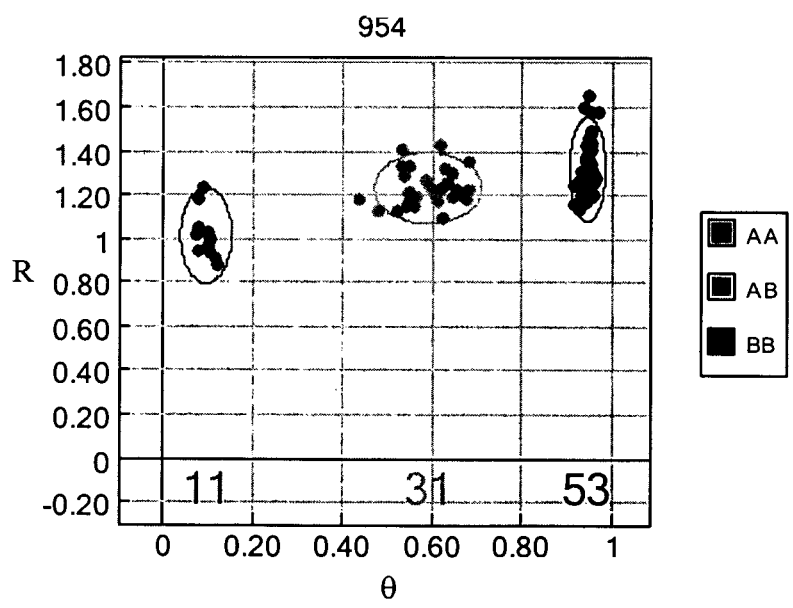
Figure 19C:
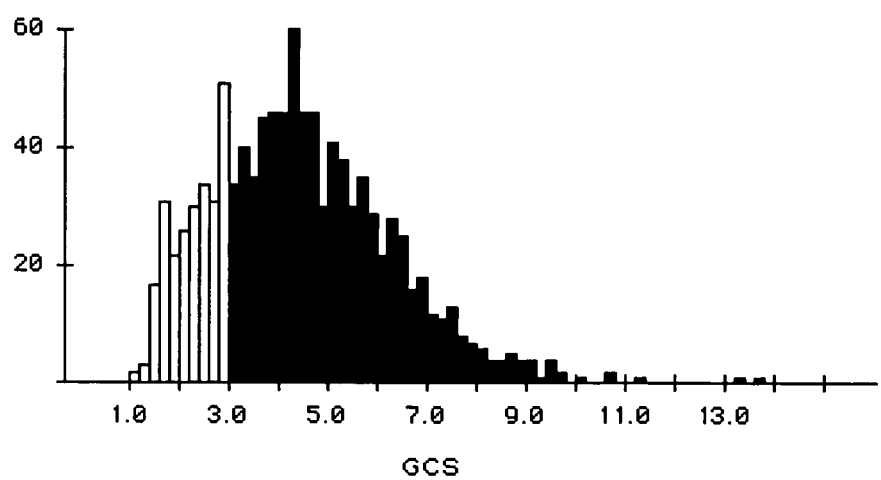

FIGS. 19A and 19B show representative Genoplots (also called GenTrain plots) for the 860 and 954 loci, respectively. Good cluster separation was obtained for the 860 and 954 loci, yielding gene cluster scores (GCS) of 7.5 and 4.4, respectively (GCS=Min[(Abs($\theta_{AB}-\theta_{AA}$)/($\sigma_{AB}+\sigma_{AA}$)), (Abs($\theta_{AB}-\theta_{BB}$)/($\sigma_{AB}+\sigma_{BB}$))], where $\theta_{AB}$ is the average $\theta$ for the AB cluster ($\theta$ is described above in regard to FIG. 11) and $\sigma_{AB}$ is the standard deviation for $\theta_{AB}$). FIG. 19C shows a distribution of loci according to genotype cluster separation score. Over 75% of loci had a GCS of 3.0 or higher (dark bars) and were, therefore, considered acceptable for genotyping.

A summary of genotyping statistics for interrogation of HapMap QC set of loci in the CEPH samples is shown in Table 1. Assay conversion rate was assessed by counting the number of loci that successfully detected a minor allele. Non-polymorphic loci and high-copy number loci were counted as assay failures in regard to developing a real SNP assay. Technically, many of the non-polymorphic loci were successful assays, but they were not counted because they did not exhibit a minor allele. The assay conversion rate compared to results from the GOLDENGATE® Assay (Illumina, Inc. San Diego, Calif.) using the same genomic DNA samples was 95%. The call rate was quite high at 99.5% and the reproducibility was greater than 99.99%.

Concordance was determined between the genotyping results obtained as described above and genotyping results obtained for the same samples and loci using the GOLDENGATE® Assay (Illumina, Inc. San Diego, Calif.). Concordance was greater than 99.9%.

TABLE 1

| Parameter | Values | Percent |
|---|---|---|
| Assay Conversion | 819/864 | 95% |
| Call Rate | 68807/68970 | 99.5% |
| Reproducibility | 8189/8190 | 99.99% |
| Concordance | 137,456/137,614 | 99.9% |

These results indicate that the whole genome genotyping assay provides high quality genotyping data, on par with the GOLDENGATE® assay which is currently being used for genotyping a large portion of the genome in the International HapMap project.

Example IX

Stripping Arrays to Remove Hybridized Target Prior to Detection

This example demonstrates removal of hybridized target from an array by stripping with 0.1 N NaOH after modification of probes by target-dependent polymerase extension.

Genomic DNA was obtained from Coriell Cell Repositories (Camden, N.J.). RPA reactions were carried out as described in Example VII. The resulting reaction mixtures were hybridized to BEADARRAYS™ and ASPE reactions performed as described in Example III. Following the ASPE reaction and prior to detection of fluorescent signal the arrays were treated with 0.1 N NaOH in water (+NaOH) or 1× hybridization buffer, lacking formamide (—NaOH). Arrays were detected as described in Example VIII.

Figure 20:
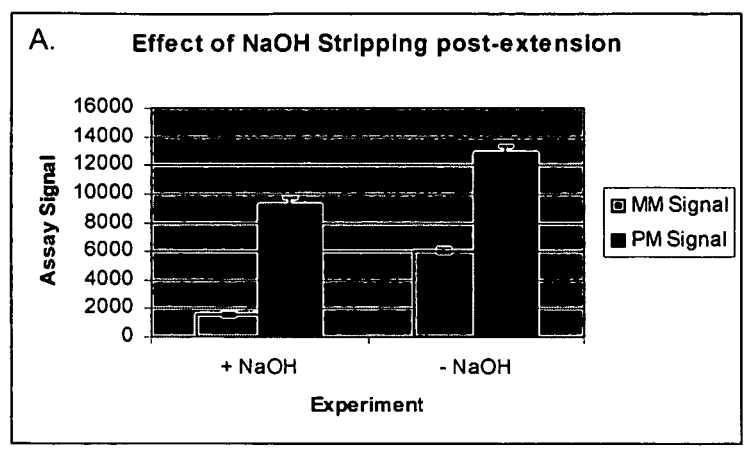
FIG. 20 shows signal intensity for perfect match (PM) and mismatch (MM) probes following allele-specific primer extension detection and treatment with or without 0.1 N NaOH.

As shown in FIG. 20, post-extension stripping of the array with NaOH reduced background signal from the mismatch probes, and resulted in a larger ratiometric difference between signal from mismatch and perfect match probes.

These results indicate that stripping arrays after probe modification although not necessary can be used to greatly improve assay specificity.

Example X

Whole Genome Amplification of Bisulfite Treated DNA

This example describes methods to whole genome amplify bisulfite-treated DNA. Typically bisulfite treatment of DNA generates substantial depurination and concomitant fragmentation of the DNA. This fragmented product is typically amplified in low yield using strand-displacing polymerases in random primer whole genome amplification approaches. Two approaches for improving amplification yield are described here. The first approach is concatenation of the fragmented sample and use of the longer concatenated products as templates for strand-displacement random primer amplification. The second approach creates a representation out of the fragmented targets by attachment of universal priming sites to the ends of the fragments.

Bisulfite treatment of genomic DNA is typically used for detecting methylation based on a reaction in which cytosine is converted to uracil, but 5-methylcytosine remains non-reactive (see, for example, Feil et al. Nucleic Acids Res, 22; 695-696 (1994); Frommer et al., Proc Natl Acad Sci USA, 89; 1827-1831 (1992)). A further reaction of DNA with bisulfite is depurination and concomitant fragmentation. The DNA fragments produced by bisulfite treatment contain a phosphate group at the 3' terminus. This phosphate group effectively blocks reaction of the 3' terminus with single nucleotides or polynucleotides using several biological enzymes.
Concatenation of Bisulfite Treated Genomic DNA The 3' phosphate group of bisulfite treated genomic DNA is removed by treatment with alkaline phosphatase or the 3' phosphatase activity of T4 DNA kinase using standard conditions recommended by the supplier. T4 DNA kinase maintains the 5' phosphate intact while removing the 3' phosphate (in the presence of ATP), resulting in a product having a 5' phosphate and 3' hydroxyl (see FIG. 21A). In contrast, alkaline phosphatase removes both the 5' and 3' phosphate, resulting in a product having both 3' and 5' hydroxyls (see FIG. 21A).

After removal of the 3' phosphate by T4 DNA kinase, the products are then incubated with T4 RNA ligase to create concatamers using conditions described in McCoy et al., supra (1980). The resulting linear and circular concatamers having various sizes are amplified by random primer amplification as described herein, for example, in Example V. This amplified product is then used for genotyping as described herein, for example, in Example VII, and provides a means for conducting genome wide methylation profiling.

Tailing of Bisulfite Treated Genomic DNA

The 3' phosphates of bisulfite treated fragments are converted into 3' hydroxyls as described above. Universal tails are added to the product using one of three different methods.

Figure 21:
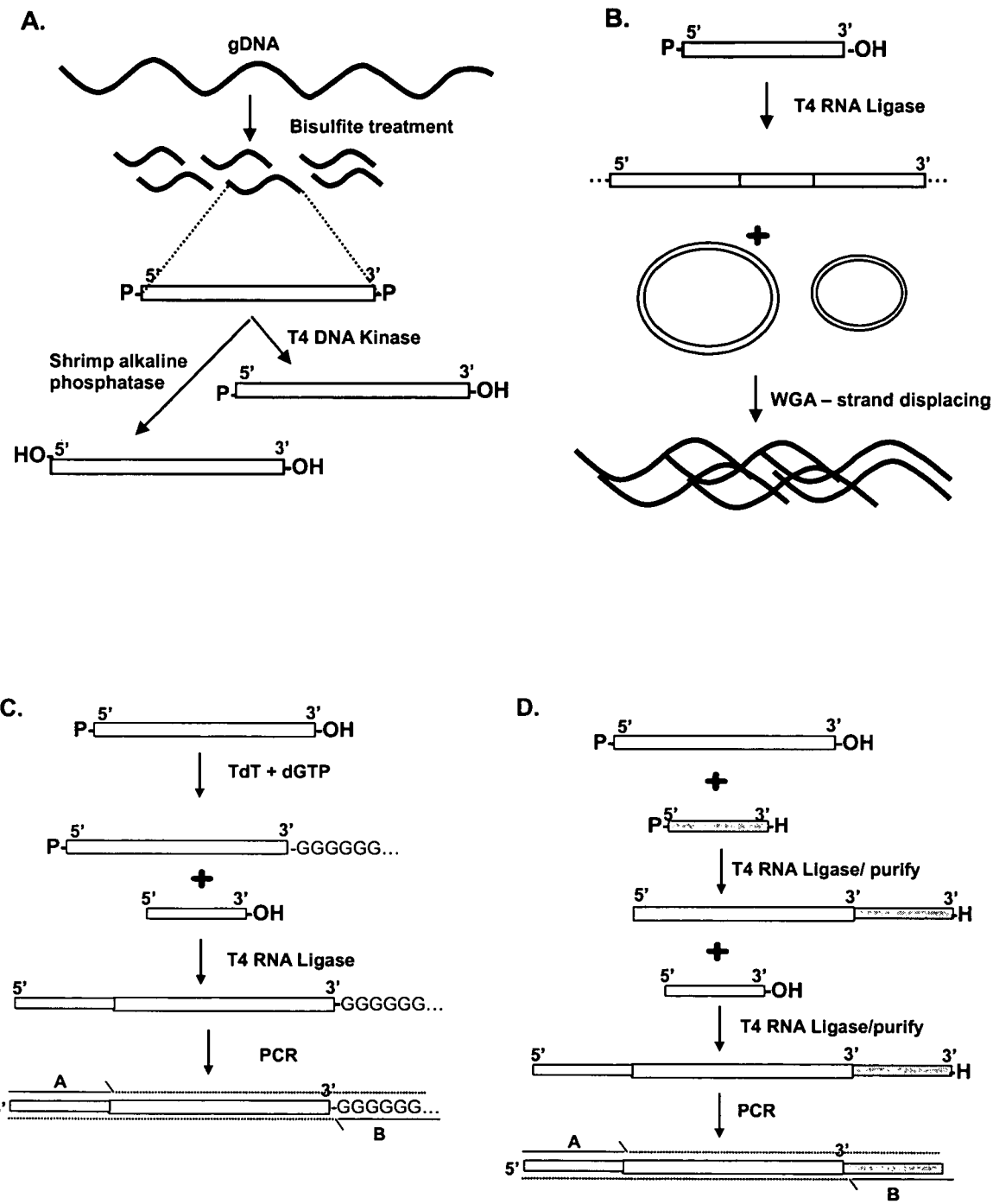
FIG. 21 shows (A) treatment of bisulfite-generated DNA fragments with alkaline phosphatase and T4 DNA kinase to generate either completely dephosphorylated or 3' dephosphorylated products, respectively; (B) treatment of 3' dephosphorylated DNA with T4 RNA ligase to produce concatenated DNA followed by amplification in a strand-displacing, whole genome, random primer amplification reaction; (C) treatment of bisulfite-generated DNA fragments with terminal deoxynucleotides transferase (TdT) and T4 RNA ligase to add universal tail sequences to the fragments followed by PCR amplification; (D) treatment of bisulfite-generated DNA fragments with T4 RNA ligase to add 5' and 3' universal tail sequence tails to the bisulfite product followed by PCR amplification.

The first method is treatment of DNA fragments with terminal deoxynucleotide transferase (TdT) and dGTP to add a polyguanylate tail to the 3' end (see FIG. 21C). A universal tail is added to the 5' end of the fragment incubation with DNA ligase and an oligonucleotide having a 3' random 4-mer duplex adapter and a 5' universal priming site sequence (FIG. 21C) using standard conditions recommended by the supplier. The resulting fragments are amplified by polymerase chain reaction using a universal primer (primer A in FIG. 21C) that complements the 5' universal priming site tail of the fragments and a polycytidylate primer (primer B in FIG. 21C) that complements the 3' polyguanylate tail of the fragments.

In the second method a 5' tail is added by T4 RNA ligase-mediated ligation of an oligonucleotide having a universal priming site using standard conditions recommended by the supplier. As shown in FIG. 21D, the reaction is carried out in two steps. In the first step, a universal priming site oligonucleotide having a 5' phosphate but lacking a 3' hydroxyl is reacted with the fragment such that a 3' tail is added to the fragment. In the second step, a universal priming site oligonucleotide having a 3' hydroxyl but lacking a 5' phosphate is reacted with the fragment such that a 5' tail is added to the fragment. The use of blocked oligonucleotides in two steps reduces unwanted side reactions due to self-ligation of the universal priming site oligonucleotides. The resulting fragments are amplified by polymerase chain reaction using a universal primer (primer A in FIG. 21D) that complements the 5' universal priming site tail of the fragments and a universal primer (primer B in FIG. 21D) that complements the 3' universal priming site of the fragments. This amplified product is then used for genotyping as described herein, for example, in Example VII, and provides a means for conducting genome wide methylation profiling.

The third method employs direct ligation of oligonucleotides having universal priming sites to both the 3' and 5' termini using T4 RNA polymerase using standard conditions recommended by the supplier. Complementary universal primers are then used to amplify the fragments by polymerase chain reaction. This amplified product is then used for genotyping as described herein, for example, in Example VII, and provides a means for conducting genome wide methylation profiling.

Throughout this application various publications, patents and patent applications have been referenced. The disclosure of these publications patents and patent applications in their entireties are hereby incorporated by reference in this application in order to more fully describe the state of the art to which this invention pertains.

The term "comprising" is intended herein to be open-ended, including not only the recited elements, but further encompassing any additional elements.

Various embodiments of the invention have been described broadly and generically herein. Each of the narrower species and subgeneric groupings falling within the generic disclosure also form the part of these inventions. This includes within the generic description of each of the inventions a proviso or negative limitation that will allow removing any subject matter from the genus, regardless or whether or not the material to be removed was specifically recited.

Although the invention has been described with reference to the examples provided above, it should be understood that various modifications can be made without departing from the invention. Accordingly, the invention is limited only by the claims.

What is claimed is:

1. A method for indicating the presence of single nucleotide polymorphisms (SNPs) of interest in typable loci of a genome, comprising the steps of:
   (a) providing an array of at least 1,000 different immobilized nucleic acid probes that are attached to a surface for flow-through sample analysis, wherein said at least 1,000 different immobilized nucleic acid probes comprise a region of at most 100 nucleotides in length that are complementary to at least 1,000 different typable loci of a genome;
   (b) contacting said array with a population of genome fragments representing 1.7 Gigabases or more of genomic sequence under conditions wherein probe-fragment hybrids are formed;
   (c) contacting said probe-fragment hybrids with a polymerase and a nucleotide analog comprising a label under conditions whereby if the typable locus of a fragment contains a SNP of interest, the hybridized probe is modified by incorporation of the nucleotide analog to obtain a labeled probe; and
   (d) detecting the labeled probe, thereby indicating the presence of said single nucleotide polymorphisms of interest at typable loci of said genome.

2. The method of claim 1, wherein said population of genome fragments is obtained by amplification under isothermal conditions and is amplified at least 10-fold.

3. The method of claim 1, wherein said population of genome fragments is obtained by denaturing said genome prior to step (b).

4. The method of claim 3, wherein said denaturing comprises heat denaturing.

5. The method of claim 1, wherein said immobilized nucleic acid probes are attached to particles.

6. The method of claim 5, wherein each of said particles is attached to a single type of nucleic acid probe.

7. The method of claim 1, wherein the surface is a flat or planar substrate upon which said immobilized nucleic acid probes are attached.

8. The method of claim 1, wherein at least 100,000 of said different nucleic acid probes hybridize with genome fragments to form probe-fragment hybrids.

9. The method of claim 1, wherein said population of genome fragments is obtained by random primer amplification.

10. The method of claim 1, wherein said population of genome fragments is obtained using a polymerase having low processivity.

11. The method of claim 1, further comprising exposing said probe-fragment hybrids to denaturing conditions after step (c), thereby removing said genome fragments.

12. The method of claim 1, wherein the label is an affinity ligand, thereby forming affinity ligand-labeled probes.

13. The method of claim 12, further comprising contacting said affinity ligand-labeled probes with a receptor and an amplification reagent, wherein said receptor has one or more sites capable of binding said ligand, and wherein said amplification reagent has affinity for said receptor, whereby multimeric complexes form between said affinity ligand-labeled probes, said receptor and said amplification reagent.

14. The method of claim 13, wherein said detecting comprises detecting said multimeric complexes.

15. The method of claim 1, wherein said probes are 25 to 60 nucleotides in length.

16. The method of claim 1, wherein the population of genome fragments represent 2.7 Gigabases or more of genomic sequence.

17. The method of claim 1, wherein the genome fragments are at most 0.6 kb in length.

18. The method of claim 1, wherein said genome fragments are concatenated DNA produced by ligating fragmented genomic DNA.

19. The method of claim 1, wherein at least 30 copies and at most 10,000 copies of said genome are representationally amplified.

20. The method of claim 1, further comprising the step of
   (b1) after step (b), contacting the plurality of nucleic acid probes with an ectopic extension inhibitor (EE1) under conditions wherein probe-EE1 hybrids are formed; whereby step (c) detects probe-fragment hybrids selectively compared to probe-EE1 hybrids.

21. The method of claim 20, wherein the EE1 is a single-stranded nucleic acid binding protein (SSB).

22. The method of claim 20, wherein the EE1 is a blocking oligonucleotide that is complementary to the 3'-end of a nucleic acid probe.

23. The method of claim 1, wherein at least one of the plurality of different nucleic acid probes comprises a first region and a second region, wherein the second region is complementary to the first region, whereby a probe that does not form a probe-fragment hybrid forms a hairpin structure that is not capable of addition of a nucleotide or nucleotide analog by a polymerase.

24. The method of claim 23, wherein the first and second regions of the nucleic acid probe do not substantially anneal at temperatures used during probe-fragment hybridization, but anneal to form hairpin structures at temperatures used during polymerase addition.

25. The method of claim 1, wherein the addition by a polymerase is a single nucleotide analog.

26. The method of claim 1, wherein the addition by a polymerase is more than one nucleotide analog.

27. The method of claim 1, wherein said immobilized nucleic acid probes are configured as an array of arrays, having a plurality of individual arrays configured to allow processing of multiple samples.

28. The method of claim 1, wherein the nucleotide analog in step (c) comprises a native nucleotide and a detection label.

29. The method of claim 1, wherein the nucleotide analog in step (c) comprises a non-native nucleotide and a detection label.

30. The method of claim 2, wherein said population of genome fragments is obtained by random primer amplification.

\* \* \* \* \*